United States Patent
Mandell et al.

(10) Patent No.: US 11,578,094 B2
(45) Date of Patent: *Feb. 14, 2023

(54) CHARGE-TAGGED NUCLEOTIDES AND METHODS OF USE THEREOF

(71) Applicants: ILLUMINA, INC., San Diego, CA (US); ILLUMINA SINGAPORE PTE. LTD., Singapore (SG)

(72) Inventors: Jeffrey Mandell, San Diego, CA (US); Silvia Gravina, San Diego, CA (US); Sergio Peisajovich, San Diego, CA (US); Kaitlin Pugliese, San Diego, CA (US); Yin Nah Teo, Singapore (SG); Xiangyuan Yang, Singapore (SG); Maria Candelaria Rogert Bacigalupo, San Diego, CA (US)

(73) Assignees: ILLUMINA, INC., San Diego, CA (US); ILLUMINA SINGAPORE PTE. LTD., Singapore (SG)

(*) Notice: Subject to any disclaimer, the term of this patent is extended or adjusted under 35 U.S.C. 154(b) by 132 days.

This patent is subject to a terminal disclaimer.

(21) Appl. No.: 17/106,963

(22) Filed: Nov. 30, 2020

(65) Prior Publication Data

US 2021/0179657 A1  Jun. 17, 2021

Related U.S. Application Data

(63) Continuation of application No. 16/627,035, filed as application No. PCT/US2019/018565 on Feb. 19, 2019, now Pat. No. 10,851,131.

(60) Provisional application No. 62/710,461, filed on Feb. 16, 2018, provisional application No. 62/710,327, filed on Feb. 16, 2018, provisional application No. 62/710,333, filed on Feb. 16, 2018, provisional application No. 62/710,362, filed on Feb. 16, 2018.

(51) Int. Cl.
*C12Q 1/68* (2018.01)
*C07H 21/00* (2006.01)
*C12Q 1/6869* (2018.01)
*C40B 70/00* (2006.01)

(52) U.S. Cl.
CPC ........... *C07H 21/00* (2013.01); *C12Q 1/6869* (2013.01); *C12Q 2521/543* (2013.01); *C12Q 2525/101* (2013.01); *C12Q 2535/122* (2013.01); *C12Q 2563/113* (2013.01); *C40B 70/00* (2013.01)

(58) Field of Classification Search
CPC .............................. C07H 21/00; C12Q 1/6869
See application file for complete search history.

(56) References Cited

U.S. PATENT DOCUMENTS

| | | | |
|---|---|---|---|
| 7,057,026 B2 | 6/2006 | Barnes et al. | |
| 7,414,116 B2 | 8/2008 | Milton et al. | |
| 7,427,673 B2 | 9/2008 | Balasubramanian et al. | |
| 8,871,921 B2 | 10/2014 | O'Halloran | |
| 10,851,131 B2* | 12/2020 | Mandell | C12Q 1/6869 |
| 2009/0186343 A1 | 7/2009 | Wang et al. | |
| 2010/0029494 A1 | 2/2010 | Cherkasov et al. | |
| 2012/0009567 A1 | 1/2012 | Fedorov et al. | |
| 2013/0078622 A1 | 3/2013 | Collins et al. | |
| 2016/0017416 A1 | 1/2016 | Boyanov et al. | |
| 2017/0314072 A1 | 11/2017 | Vijayan et al. | |
| 2018/0155773 A1 | 6/2018 | Gunderson et al. | |
| 2019/0112650 A1 | 4/2019 | Ju et al. | |
| 2020/0123193 A1 | 4/2020 | Mandell et al. | |

FOREIGN PATENT DOCUMENTS

| | | |
|---|---|---|
| WO | 1991006678 | 5/1991 |
| WO | 2007123744 | 11/2007 |
| WO | 2009145820 A2 | 3/2009 |
| WO | 2010141390 A2 | 12/2010 |
| WO | 2015148402 A1 | 10/2015 |
| WO | 2016010975 A1 | 1/2016 |
| WO | 2017024049 A1 | 2/2017 |
| WO | 2017087974 A1 | 5/2017 |
| WO | 2017184996 A1 | 10/2017 |

(Continued)

OTHER PUBLICATIONS

International Search Report and Written Opinion of the International Searching Authority for International Application No. PCT/US2019/018565 dated May 6, 2019.
Fuller, C.W., et al., "Real-time single-molecule electronic DNA sequencing by synthesis using polymer-tagged nucleotides on a nanopore array", PNAS, vol. 113, No. 19, pp. 5233-5238 (2016).
Kumar, S., et al., "PEG-Labeled Nucleotides and Nanopore Detection for Single Molecule DNA Sequencing by Synthesis", Scientific Reports, vol. 2, srep00684, 1-8 (2012).

(Continued)

*Primary Examiner* — Jezia Riley
(74) *Attorney, Agent, or Firm* — Heslin Rothenberg Farley & Mesiti P.C.

(57) ABSTRACT

Provided is a method including detecting an incorporation of a labelled nucleotide into a nascent polynucleotide strand complementary to a template polynucleotide strand by a polymerase, wherein the polymerase is tethered to a solid support conductive channel by a tether and the labelled nucleotides is a compound of Formula I:

(Continued)

20 Claims, 24 Drawing Sheets

(56) References Cited

FOREIGN PATENT DOCUMENTS

WO    2017203059 A1    11/2017
WO    2019027604 A1    2/2019

OTHER PUBLICATIONS

Ong, L.L., et al., "Programmable self-assembly of three-dimensional nanostructures from 10,000 unique components", Nature, vol. 552, pp. 72-77 (2017).

Praetorius, F., et al., "Biotechnological mass production of DNA origami", Nature, vol. 552, pp. 84-87 (2017).

Shiraishi, T., et al., "Peptide nucleic acid (PNA) cell penetrating peptide (CPP) conjugates as carriers for cellular delivery of antisense oligomers", Artificial DNA: PNA & XNA, vol. 2, Issue 3, pp. 90-99 (2011).

Tikhomirov, G., et al., "Fractal assembly of micrometre-scale DNA origami arrays with arbitrary patterns", Nature, vol. 552, pp. 67-71 (2017).

Wagenbauer, K.F., et al., "Gigadalton-scale shape-programmable DNA assemblies", Nature, vol. 552, pp. 78-83 (2017).

Zhang, F., et al., "DNA self-assembly scaled up", Nature, vol. 552, pp. 34-35 (2017).

Choi, et al., "Dissecting Single-Molecule Signal Transduction in Carbon Nanotube Circuits with Protein Engineering" Nano Letters, 625-631, 2013.

Choi, et al., "Single-Molecule Lysozyme Dynamics Monitored by an Electronic Circuit" Science vol. 335, 319-324, 2012.

Onescu, et al., "Tunnel field-effect transistors as energy-efficient electronic switches" Nature vol. 479, 329-337, 2011.

Olsen, et al., "Electronic Measurements of Single-Molecule Processing by DNA Polymerase I (Klenow Fragment)" J Am Chem Soc 135(21), 7855-7860, 2013.

Swaminathan, et al., "Sleep Slope Devices: Enabling New Architectural Paradigms" Proceedings of the 51st Annual Design Automation Conference on Design Automation Conference, 1-6, 2014.

* cited by examiner

CHARGE-TAGGED NUCLEOTIDES AND METHODS OF USE THEREOF

CROSS-REFERENCE TO RELATED APPLICATIONS

This application is a continuation of U.S. patent application Ser. No. 16/627,035, filed on Dec. 27, 2019, published as US 2020-0123193 A1 on Apr. 23, 2020, as a national stage filing under 35 U.S.C. § 371 of International Application No. PCT/US2018/027961, filed on Apr. 17, 2018, published as WO 2018195070 on Oct. 25, 2018, and claims priority to U.S. Provisional Patent Application No. 62/710,327, filed Feb. 16, 2018, and to U.S. Provisional Patent Application No. 62/710,333, filed Feb. 16, 2018, and to U.S. Provisional Patent Application No. 62/710,362, filed Feb. 16, 2018, and to U.S. Provisional Patent Application No. 62/710,461, filed Feb. 16, 2018. The entire disclosures of each of the said applications are incorporated by reference in their entireties herein.

BACKGROUND

The majority of the current sequencing platforms use "sequencing by synthesis" (SBS) technology and fluorescence based methods for detection. Alternative sequencing methods that allow for more cost effective, rapid, and convenient sequencing and nucleic acid detection are desirable as complements to SBS. Charge based sequencing is an attractive approach.

Current sequencing by synthesis (SBS) technology uses nucleotides that are modified at two positions: 1) the 3' hydroxyl (3'-OH) of deoxyribose, and 2) the 5-position of pyrimidines or 7-position of purines of nitrogeneous bases (A, T, C, G). The 3'—OH group is blocked with an azidomethyl group to create reversible nucleotide terminators. This may prevent further elongation after the addition of a single nucleotide. Each of the nitrogeneous bases is separately modified with a fluorophore to provide a fluorescence readout which identifies the single base incorporation. Subsequently, the 3'-OH blocking group and the fluorophore are removed and the cycle repeats.

The current cost of the modified nucleotides may be high due to the synthetic challenges of modifying both the 3'-OH of deoxyribose and the nitrogeneous base. There are several possible methods to reduce the cost of the modified nucleotides. One method is to move the readout label to the 5'-terminal phosphate instead of the nitrogeneous base. In one example, this removes the need for a separate cleavage step, and allows for real time detection of the incoming nucleotide. During incorporation, the pyrophosphate together with the tag is released as a by-product of the elongation process, thus a cleavable linkage is not involved.

SUMMARY

Examples provided herein include a method for detecting a nucleotide incorporated into a nascent polynucleotide strand by a polymerase and compositions for use in said method. One example provided herein is a method for detecting, with a conductive channel, a nucleotide bearing a charged tag during such incorporation, and compounds of such nucleotides with such charged tags. One example provides nucleotides having charge tags including phosphodiester groups, amino acids, dendron architecture, and other architectural structures that enhance charge density, methods for linking nucleotides to charge tags with enhanced charge density, and methods of using nucleotides having charge tags with enhanced charge density.

In one aspect, provided is a method including detecting an incorporation of a labelled nucleotide into a nascent polynucleotide strand complementary to a template polynucleotide strand by a polymerase, wherein the polymerase is tethered to a solid support conductive channel by a tether, the labelled nucleotide is a compound of Formula I

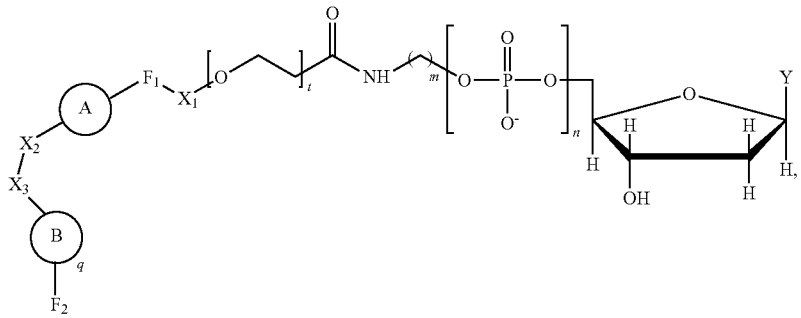

wherein n is an integer from 3 to 10, m is an integer from 1 to 10, t is an integer from 0 to 50, $X_1$ is a direct bond, a $C_1$-$C_{10}$ alkyl, a $C_1$-$C_{10}$ oxaalkyl, a $C_1$-$C_{10}$ thiaalkyl, or a $C_1$-$C_{10}$ azaalkyl, $X_2$ is $C_1$-$C_{20}$ alkyl wherein optionally one or more individual $CH_2$ residue is replaced with one or more of a peptide bond and $(-O-CH_2-CH_2-)_a$ wherein a is an integer from 1 to 24, $X_3$ is a direct bond or an oligonucleotide wherein the oligonucleotide hybridizes to an acceptor region of the tether when the label is in proximity to the conductive channel, $F_1$ is selected from a fluorophore and a direct bond and $F_2$ is absent or a fluorophore, A is

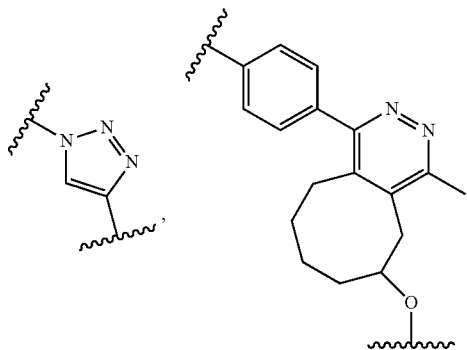

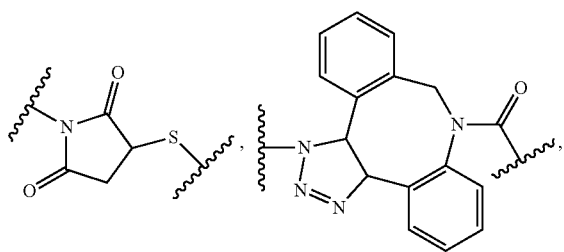

or an amide bond, and
Y is selected from

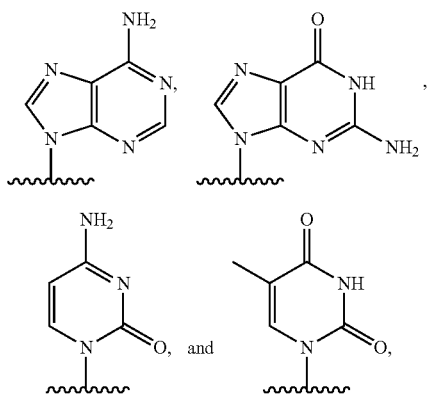

q is an integer from 1 to 100, and
B is selected from an amino acid, a nucleotide,

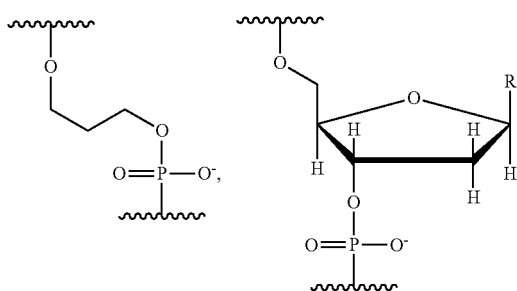

wherein R is selected from Y and hydrogen, and a dendron; and wherein q is equal to 1 when B is a dendron, and the q number of B has a charge and a charge density, and the conductive channel is to detect the labelled nucleotide during the incorporation.

In an example, the charge is between about −100e and about +100e. In another example, the charge density is between about −100e per cubic nanometer and about +100e per cubic nanometer. In yet another example, the charge is between about −200e and about +200e. In still a further example, the charge density is between about −200e per cubic nanometer and about +200e per cubic nanometer.

In a further example, the q number of B includes a polynucleotide. In yet a further example, the polynucleotide is selected from a branched polynucleotide and one or more hairpin loops. In still another example, the polynucleotide includes between two and five hairpin loops.

In another example, the q number of B includes a polypeptide. In yet another example, the polypeptide is selected from the group consisting of branched polypeptide, coiled polypeptide, and coiled-coil polypeptide. In still another example, B includes an amino acid and one or more of the q number of B includes methyllysine, dimethyllysine, or trimethyllysine.

In another example, B is a dendron of z generations including one or more constitutional repeating unit and a plurality of end units, wherein z is an integer from 1 to 6, the constitutional end units are selected from:

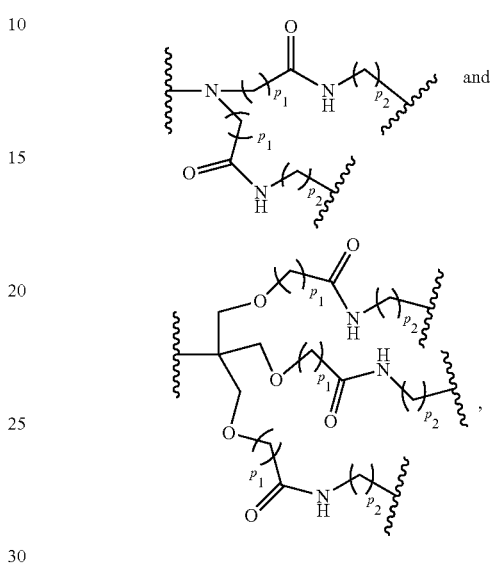

wherein
$p_1$ is an integer from 1 to 3, wherein any one or more of the $p_1$ —CH$_2$— groups is optionally replaced with from 1 to 3 —O—CH$_2$—CH$_2$— groups, $p_2$ is an integer from 1 to 3, wherein any one or more of the $p_2$ —CH$_2$— groups is optionally replaced with from 1 to 3 —O—CH$_2$—CH$_2$— groups, and the end groups are selected from carboxylic acid, sulfonic acid, phosphonic acid, sperminyl group, amino group, and quaternary ammonium group.

In yet another example, A was formed by a reaction including a linking reaction and the linking reaction is selecting from an azide-alkyne copper-assisted click reaction, a tetrazine-trans-cyclooctene ligation, an azide-dibenzocyclooctyne group copper-free click reaction, and a thiol-maleimide conjugation.

In still another example, the method further includes successively incorporating a plurality of labelled nucleotides wherein the charge of each of the plurality of labelled nucleotides differs from the charge of any other of the plurality of labelled nucleotides when the Y of the each and the Y of the any other differ from each other. In a further example, the method further includes identifying the Y of one or more labelled polynucleotide incorporated into the nascent polynucleotide strand based on the charge detected by the conductive channel.

In yet a further example, $X_2$ is (—O—CH$_2$—CH$_2$—)$_a$ wherein a is an integer from 1 to 24. In an example, a is 24. In another example, a is 12. In another example, a is 8. In still another example, a is 4.

In another aspect, provided is a method including detecting an incorporation of a labelled nucleotide into a nascent polynucleotide strand complementary to a template polynucleotide strand by a polymerase, wherein the polymerase is tethered to a solid support conductive channel by a tether, the labelled nucleotide is a compound of Formula I

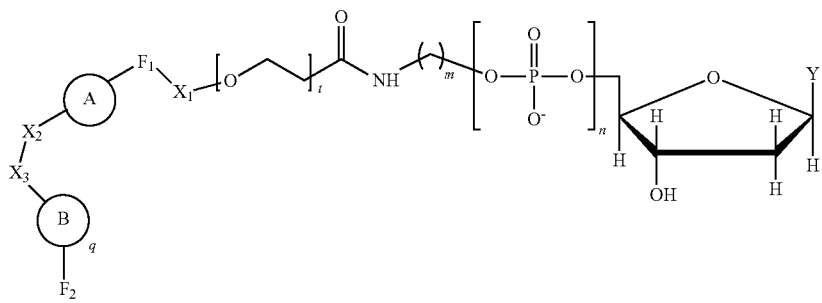

wherein n is an integer from 3 to 10, m is an integer from 1 to 10, t is an integer from 0 to 50, $X_1$ is a direct bond, a $C_1$-$C_{10}$ alkyl, a $C_1$-$C_{10}$ oxaalkyl, a $C_1$-$C_{10}$ thiaalkyl, or a $C_1$-$C_{10}$ azaalkyl, $X_2$ is $C_1$-$C_{20}$ alkyl wherein optionally one or more individual $CH_2$ residue is replaced with one or more of a peptide bond and (—O—$CH_2$—$CH_2$—)$_a$ wherein a is an integer from 1 to 24, $X_3$ is a direct bond or an oligonucleotide wherein the oligonucleotide hybridizes to an acceptor region of the tether when the label is in proximity to the conductive channel, $F_1$ is selected from a fluorophore and a direct bond and $F_2$ is absent or a fluorophore, A is

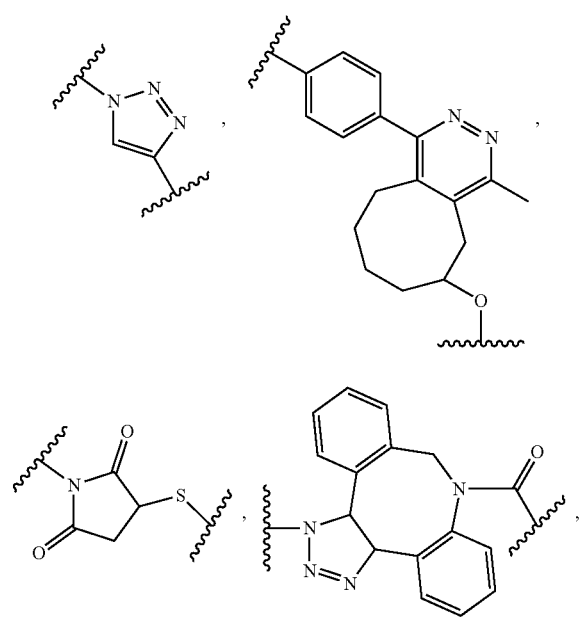

or an amide bond, and

Y is selected from

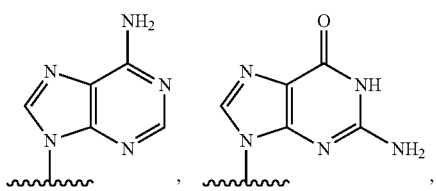

-continued

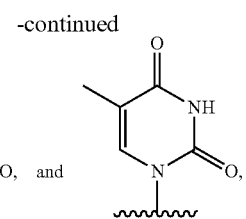

q is an integer from 1 to 100, and

B includes an amino acid, and the q number of B has a charge and a charge density, and the conductive channel is to detect the labelled nucleotide during the incorporation.

In an example, the charge is between about −100e and about +100e. In another example, the charge density is between about −100e per cubic nanometer and about +100e per cubic nanometer. In yet another example, the charge is between about −200e and about +200e. In still a further example, the charge density is between about −200e per cubic nanometer and about +200e per cubic nanometer.

In another example, the q number of B includes a polypeptide. In yet another example, the polypeptide is selected from the group consisting of branched polypeptide, coiled polypeptide, and coiled-coil polypeptide. In still another example, B includes an amino acid and one or more of the q number of B includes methyllysine, dimethyllysine, or trimethyllysine.

In yet another example, A was formed by a reaction including a linking reaction and the linking reaction is selecting from an azide-alkyne copper-assisted click reaction, a tetrazine-trans-cyclooctene ligation, an azide-dibenzocyclooctyne group copper-free click reaction, and a thiol-maleimide conjugation.

In still another example, the method further includes successively incorporating a plurality of labelled nucleotides wherein the charge of each of the plurality of labelled nucleotides differs from the charge of any other of the plurality of labelled nucleotides when the Y of the each and the Y of the any other differ from each other. In a further example, the method further includes identifying the Y of one or more labelled polynucleotide incorporated into the nascent polynucleotide strand based on the charge detected by the conductive channel.

In yet a further example, $X_2$ is (—O—$CH_2$—$CH_2$—)$_a$ wherein a is an integer from 1 to 24. In an example, a is 24. In another example, a is 12. In another example, a is 8. In still another example, a is 4.

In still another aspect, provided is a method including detecting an incorporation of a labelled nucleotide into a nascent polynucleotide strand complementary to a template polynucleotide strand by a polymerase, wherein the polymerase is tethered to a solid support conductive channel by a tether, the labelled nucleotides is a compound of Formula I

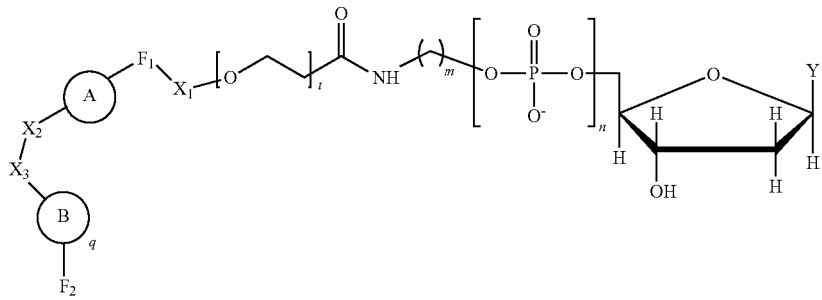

wherein n is an integer from 3 to 10, m is an integer from 1 to 10, t is an integer from 0 to 50, $X_1$ is a direct bond, a $C_1$-$C_{10}$ alkyl, a $C_1$-$C_{10}$ oxaalkyl, a $C_1$-$C_{10}$ thiaalkyl, or a $C_1$-$C_{10}$ azaalkyl, $X_2$ is $C_1$-$C_{20}$ alkyl wherein optionally one or more individual $CH_2$ residue is replaced with one or more of a peptide bond and $(-O-CH_2-CH_2-)_a$ wherein a is an integer from 1 to 24, $X_3$ is a direct bond or an oligonucleotide wherein the oligonucleotide hybridizes to an acceptor region of the tether when the label is in proximity to the conductive channel, $F_1$ is selected from a fluorophore and a direct bond and $F_2$ is absent or a fluorophore, A is

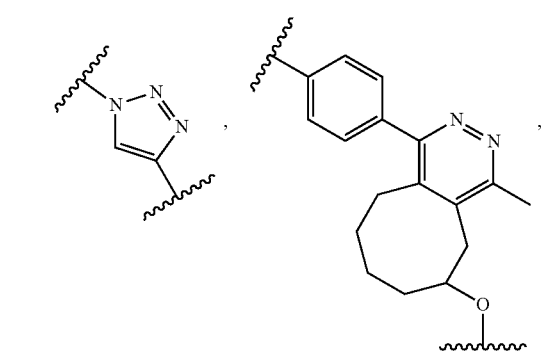

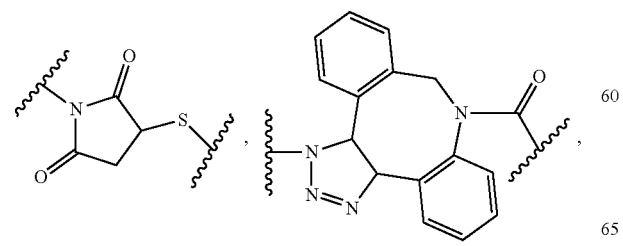

or an amide bond, and

Y is selected from

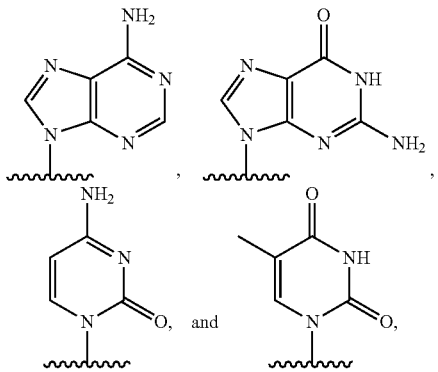

q is an integer from 1 to 100, and

B is selected from a nucleotide,

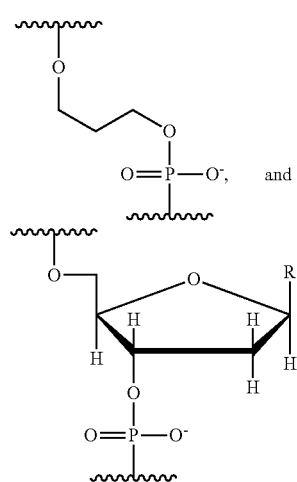

wherein R is selected from Y and hydrogen, and the conductive channel is to detect the labelled nucleotide during the incorporation.

In an example, the charge is between about −100e and about +100e. In another example, the charge density is between about −100e per cubic nanometer and about +100e per cubic nanometer. In yet another example, the charge is between about −200e and about +200e. In still a further example, the charge density is between about −200e per cubic nanometer and about +200e per cubic nanometer.

In a further example, the q number of B includes a polynucleotide. In yet a further example, the polynucleotide is selected from a branched polynucleotide and one or more hairpin loops. In still another example, the polynucleotide includes between two and five hairpin loops.

In yet another example, A was formed by a reaction including a linking reaction and the linking reaction is selecting from an azide-alkyne copper-assisted click reaction, a tetrazine-trans-cyclooctene ligation, an azide-dibenzocyclooctyne group copper-free click reaction, and a thiol-maleimide conjugation.

In still another example, the method further includes successively incorporating a plurality of labelled nucleotides wherein the charge of each of the plurality of labelled nucleotides differs from the charge of any other of the plurality of labelled nucleotides when the Y of the each and the Y of the any other differ from each other. In a further example, the method further includes identifying the Y of one or more labelled polynucleotide incorporated into the nascent polynucleotide strand based on the charge detected by the conductive channel.

In yet a further example, $X_2$ is $(-O-CH_2-CH_2-)_a$ wherein a is an integer from 1 to 24. In an example, a is 24. In another example, a is 12. In another example, a is 8. In still another example, a is 4.

In a further aspect, provided is a method including detecting an incorporation of a labelled nucleotide into a nascent polynucleotide strand complementary to a template polynucleotide strand by a polymerase, wherein the polymerase is tethered to a solid support conductive channel by a tether, the labelled nucleotide is a compound of Formula I

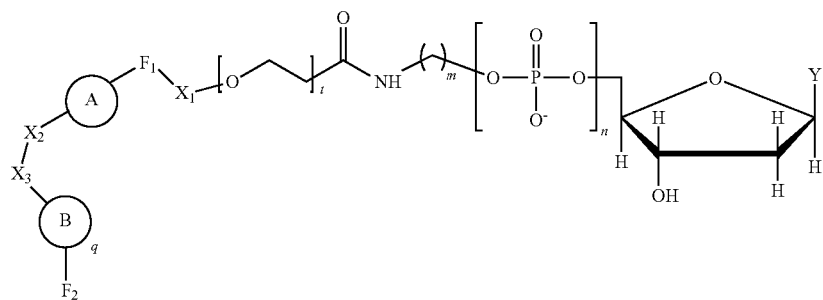

wherein n is an integer from 3 to 10, m is an integer from 1 to 10, t is an integer from 0 to 50, $X_1$ is a direct bond, a $C_1$-$C_{10}$ alkyl, a $C_1$-$C_{10}$ oxaalkyl, a $C_1$-$C_{10}$ thiaalkyl, or a $C_1$-$C_{10}$ azaalkyl, $X_2$ is $C_1$-$C_{20}$ alkyl wherein optionally one or more individual $CH_2$ residue is replaced with one or more of a peptide bond and $(-O-CH_2-CH_2-)_a$ wherein a is an integer from 1 to 24, $X_3$ is a direct bond or an oligonucleotide wherein the oligonucleotide hybridizes to an acceptor region of the tether when the label is in proximity to the conductive channel, $F_1$ is selected from a fluorophore and a direct bond and $F_2$ is absent or a fluorophore, A is

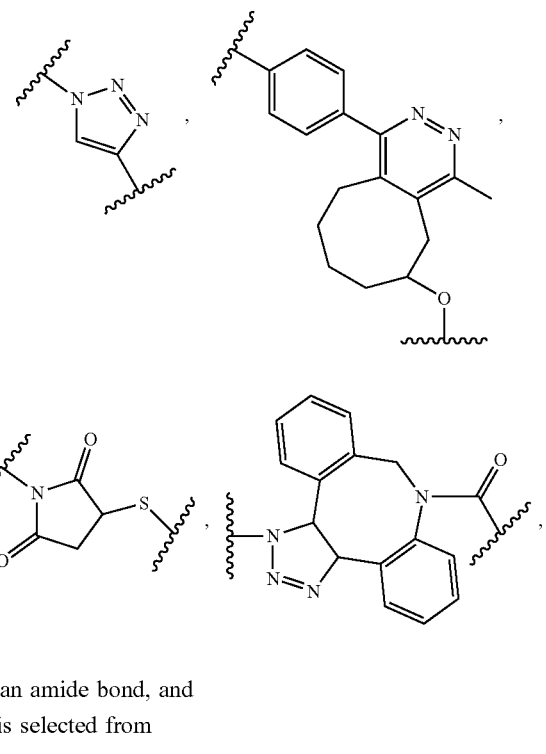

or an amide bond, and

Y is selected from

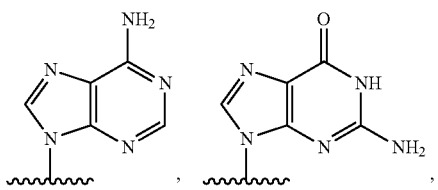

-continued

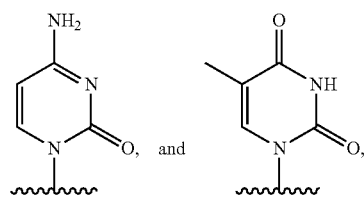

q is 1, and B includes a dendron, and B has a charge and a charge density, and the conductive channel is to detect the labelled nucleotide during the incorporation.

In an example, the charge is between about −100e and about +100e. In another example, the charge density is between about −100e per cubic nanometer and about +100e per cubic nanometer. In yet another example, the charge is between about −200e and about +200e. In still a further example, the charge density is between about −200e per cubic nanometer and about +200e per cubic nanometer.

In another example, B is a dendron of z generations including one or more constitutional repeating unit and a plurality of end units, wherein z is an integer from 1 to 6, the constitutional end units are selected from:

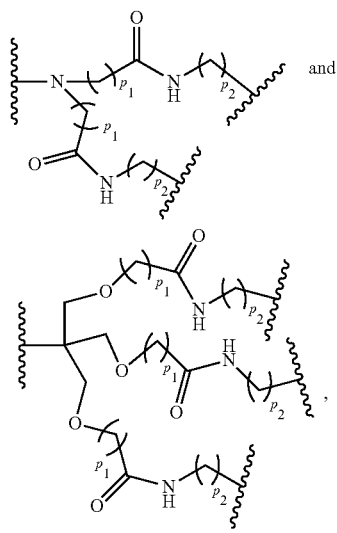

wherein
$p_1$ is an integer from 1 to 3, wherein any one or more of the $p_1$ —$CH_2$— groups is optionally replaced with from 1 to 3 —O—$CH_2$—$CH_2$— groups, $p_2$ is an integer from 1 to 3, wherein any one or more of the $p_2$ —$CH_2$— groups is optionally replaced with from 1 to 3 —O—$CH_2$—$CH_2$— groups, and the end groups are selected from carboxylic acid, sulfonic acid, phosphonic acid, sperminyl group, amino group, and quaternary ammonium group.

In yet another example, A was formed by a reaction including a linking reaction and the linking reaction is selecting from an azide-alkyne copper-assisted click reaction, a tetrazine-trans-cyclooctene ligation, an azide-dibenzocyclooctyne group copper-free click reaction, and a thiol-maleimide conjugation.

In still another example, the method further includes successively incorporating a plurality of labelled nucleotides wherein the charge of each of the plurality of labelled nucleotides differs from the charge of any other of the plurality of labelled nucleotides when the Y of the each and the Y of the any other differ from each other. In a further example, the method further includes identifying the Y of one or more labelled polynucleotide incorporated into the nascent polynucleotide strand based on the charge detected by the conductive channel.

In yet a further example, $X_2$ is (—O—$CH_2$—$CH_2$—)$_a$ wherein a is an integer from 1 to 24. In an example, a is 24. In another example, a is 12. In another example, a is 8. In still another example, a is 4.

It should be appreciated that all combinations of the foregoing concepts and additional concepts discussed in greater detail below (provided such concepts are not mutually inconsistent) are contemplated as being part of the inventive subject matter disclosed herein.

BRIEF DESCRIPTION OF THE DRAWINGS

These and other features, aspects, and advantages of the present disclosure will become better understood when the following detailed description is read with reference to the accompanying drawings, wherein:

FIG. 13A shows a stem-and-loop shaped charge tag and FIG. 13C shows a cl overleaf-shaped charge tag.

FIG. 14A shows a cruciform charge tag comprising four oligonucleotides bonded together in a Holliday structure-like configuration and single-stranded oligonucleotide overhangs. FIG. 14B shows the structure from FIG. 14A with sequences of peptide nucleic acids bound to the oligonucleotide overhands and coiled polypeptide structures extending from the ends of the peptide nucleic acid sequences. In this example, the polypeptide sequences have a positive charge.

DETAILED DESCRIPTION

Figure 1:
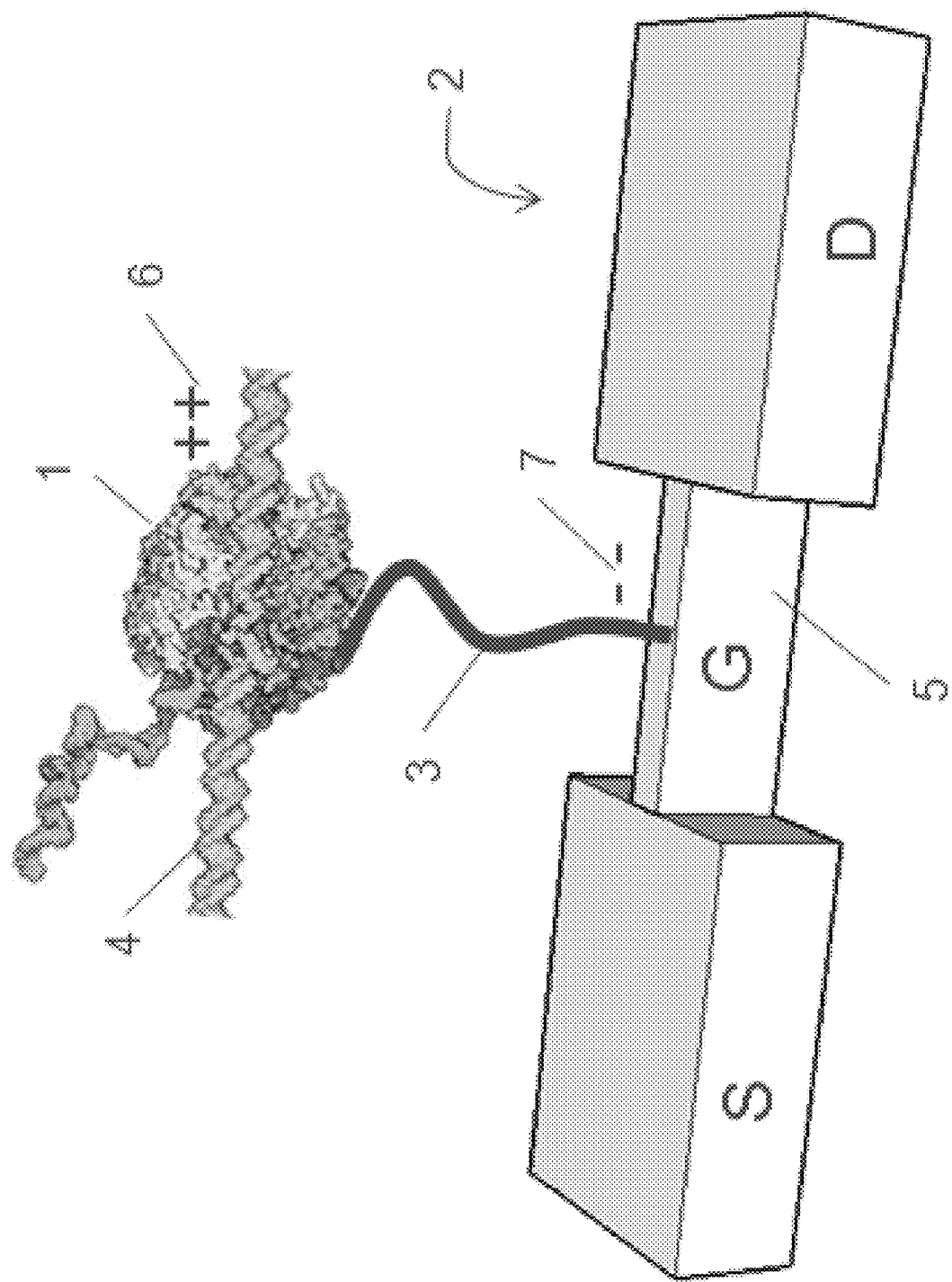
FIG. 1 shows, in one example, a polymerase attached to a conductive channel via a tether.

Examples of the present disclosure relate generally to compositions and methods for nucleotide incorporation events detected in nucleic acid sequencing procedures. There is a need for improved detection systems which provide differential recognition of nucleotides on the basis of differences in charges, such as to permit long sequencing reads in high-throughput manner. Examples set forth herein may satisfy this need and provide other advantages as well.

As disclosed herein, an, expensive and light-sensitive fluorescent label on a nucleotide with a different label for use with a different detection system. Detection of a conventional fluorescent label may involve expensive hardware such as lasers and detection optics which increases the size of a detection instrument. In addition, more powerful software is used to decode the multitude of information being generated. Importantly, as disclosed herein, expensive fluorophores are not needed. By replacing the fluorescent label with a charge label, the charge can be detected by a conductive channel which monitors the current in the system. This allows "real-time" sequencing to be performed and has the potential of achieving a faster turn-around time by reducing the cycle time of each nucleotide incorporation.

By enabling "real-time" sequencing, in one example the blocking group at the 3'-OH would not be involved. This lowers the costs of the modified nucleotides as fewer synthetic steps are involved. An additional benefit is that polymerases are better suited to incorporating nucleotides with 3' OH, that are closer to the native system, compared to a chemically modified bulky 3' protecting group.

A conductive channel for detecting a modified nucleotide including a charge may be responsive to a surrounding electric field. This field is modulated by positioning a modified nucleotide with a charge close proximity to a surface of the conductive channel. Close proximity of the charge tags to the surface may be important in some cases, such as if salt or other ions in the solution may screen a charge from detection by a conductive channel. A characteristic screening length is referred to as a Debye length, beyond which a conductive channel may be unable to detect charge.

A charge included in a modified nucleotide may be anywhere from between −200e to +200e, which may be in excess of 160 Angstroms when fully stretched linearly, whereas a Debye zone of a conductive channel may be about 1 nm. Thus, structuring of a charge-carrying modification of a nucleotide to promote detection thereof by a conductive channel would be desirable.

Terms used herein will be understood to take on their ordinary meaning unless specified otherwise. Examples of several terms used herein and their definitions are set forth below.

As used herein, the term "array" refers to a population of conductive channels or molecules that are attached to one or more solid-phase substrates such that the conductive channels or molecules can be differentiated from each other according to their relative location. An array can include different molecules that are each located at a different addressable location (e.g. at different conductive channels) on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. Molecules of the array can be nucleic acid primers, nucleic acid probes, nucleic acid templates or nucleic acid enzymes such as polymerases and exonucleases.

As used herein, the term "attached" refers to the state of two things being joined, fastened, adhered, connected or bound to each other. For example, a reaction component, such as a polymerase, can be attached to a solid phase component, such as a conductive channel, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "electrically conductive channel" is intended to mean a portion of a detection device that translates perturbations at its surface or in its surrounding electrical field into an electrical signal. The conductive channel may be an electrically conductive channel. For example, as shown in FIG. 1, an electrically conductive channel 5 can translate the arrival or departure of a reaction component (e.g., the labeled nucleotide) into an electrical signal. In the examples disclosed herein, the electrically conductive channel 5 can also translate interactions between two reaction components (the template nucleic acid and a nucleotide of the labeled nucleotide) into a detectable signal through its interaction with the redox-active charge tag of the labeled nucleotide.

The electrically conductive channel 5 may be the channel of a conductive channel 2. The conductive channel 2 may include source and drain terminals S, D and the channel 5 connecting the terminals S, D. The channel may have any suitable geometries—e.g., tube, wire, plate, etc.

As used herein, the term "conductive channel" is intended to mean a detection device that translates perturbations at its surface or in its surrounding electrical field into an electrical signal. For example, a conductive channel can translate the arrival or departure of a reaction component into an electrical signal. A conductive channel can also translate interactions between two reaction components, or conformational changes in a single reaction component, into an electrical signal. An example conductive channel is a field effect transistor (FET) such as a carbon nanotube (CNT), single-walled carbon nanotube (SWNT) based FET, silicon nanowire (SiNW) FET, graphene nanoribbon FET (and related nanoribbon FETs fabricated from 2D materials such as $MoS_2$, silicene, etc), tunnel FET (TFET), and steep subthreshold slope devices (see, for example, Swaminathan et al., *Proceedings of the 51st Annual Design Automation Conference on Design Automation Conference*, pg 1-6, ISBN: 978-1-4503-2730-5 (2014) and Ionescu et al., *Nature* 479, 329-337 (2011); each of which is incorporated by reference in its entirety). Examples of FET and SWNT conductive channels that can be used in the methods and apparatus of the present disclosure are set forth in US Pat. App. Pub. No. 2013/0078622 A1, which is incorporated herein by reference in its entirety.

The terminals S, D may be any suitable conductive material. Examples of suitable source and drain materials include cobalt, cobalt silicide, nickel, nickel silicide, aluminum, tungsten, copper, titanium, molybdenum, indium tin oxide (ITO), indium zin oxide, gold, platinum, carbon, etc.

The conductive channel 5 may include any conductive or semi-conductive material that can oxidize or reduce the redox-active charge tag. The material may comprise an organic material, an inorganic material, or both. Some examples of suitable channel materials include silicon, carbon (e.g., glassy carbon, graphene, etc.), polymers, such as conductive polymers (e.g., polypyrrole, polyaniline, polythiophene, poly(3,4-ethylenedioxythiophene) doped with poly(4-styrenesulfonate) (PEDOT-PSS), etc.), metals, biomolecules, etc.

In some examples, the conductive channel 5 may also be a nanostructure that has at least one dimension on the nanoscale (ranging from 1 nm to less than 1 µm). In one example, this dimension refers to the largest dimension. As examples, the electrically conductive channel 5 may be a semi-conducting nanostructure, a graphene nanostructure, a metallic nanostructure, and a conducting polymer nanostructure. The nanostructure may be a multi- or single-walled nanotube, a nanowire, a nanoribbon, etc.

As used herein, the term "different", when used in reference to nucleic acids, means that the nucleic acids have nucleotide sequences that are not the same as each other. Two or more different nucleic acids can have nucleotide sequences that are different along their entire length. Alternatively, two or more different nucleic acids can have nucleotide sequences that are different along a substantial portion of their length. For example, two or more different nucleic acids can have target nucleotide sequence portions that are different for the two or more molecules while also having a universal sequence portion that is the same on the two or more molecules. The term "different" can be similarly applied to other molecules, such as polymerases and nucleic acid enzymes.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "label," when used in reference to a reaction component, is intended to mean a detectable reaction component or detectable moiety of a reaction component. A useful label is a charge label (also called a charge tag) that can be detected by a conductive channel. A label can be intrinsic to a reaction component that is to be detected (e.g. a charged amino acid of a polymerase) or the label can be extrinsic to the reaction component (e.g. a non-naturally occurring modification of an amino acid). In some examples a label can include multiple moieties having separate functions. For example a label can include a linker component (such as a nucleic acid) and a charge tag component.

As used herein, the term "non-natural," when used in reference to a moiety of a molecule, is intended to refer to a moiety that is not found attached to the molecule in its natural milieu or in a biological system unperturbed by human, technical intervention. Typically, non-natural moieties are synthetic modifications of molecules that render the molecules structurally or chemically distinct from the unmodified molecule or from molecules having natural modifications. As used herein, the term "non-natural," when used in reference to an analog used for a process, is intended to mean an analog that is not found in the natural milieu where the process occurs. Typically, non-natural analogs are synthetic analogs that are structurally or chemically distinct from other types of molecules in the class to which the analog belongs.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art such as peptide nucleic acid (PNA) or locked nucleic acid (LNA). Naturally occurring nucleic acids generally have a deoxyribose sugar (e.g. found in deoxyribonucleic acid (DNA)) or a ribose sugar (e.g. found in ribonucleic acid (RNA)).

A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine, or guanine and a ribonucleic acid can have one or more bases selected from the group consisting of uracil, adenine, cytosine or guanine. Useful non-native bases that can be included in a nucleic acid are known in the art.

As used herein, the term "nucleotide" is intended to include natural nucleotides, analogs thereof, ribonucleotides, deoxyribonucleotides, dideoxyribonucleotides and other molecules known as nucleotides. The term can be used to refer to a monomeric unit that is present in a polymer, for example to identify a subunit present in a DNA or RNA strand. The term can also be used to refer to a molecule that is not necessarily present in a polymer, for example, a molecule that is capable of being incorporated into a polynucleotide in a template dependent manner by a polymerase. The term can refer to a nucleoside unit having, for example, 0, 1, 2, 3 or more phosphates on the 5' carbon. For example, tetraphosphate nucleotides, pentaphosphate nucleotides, and hexaphosphate nucleotides can be particularly useful, as can nucleotides with more than 6 phosphates, such as 7, 8, 9, 10, or more phosphates, on the 5' carbon. Example natural nucleotides include, without limitation, ATP, UTP, CTP, and GTP (collectively NTP), and ADP, UDP, CDP, and GDP (collectively NDP), or AMP, UMP, CMP, or GMP (collectively NMP), or dATP, dTTP, dCTP, and dGTP (collectively dNTP), and dADP, dTDP, dCDP, and dGDP (collectively dNDP), and dAMP, dTMP, dCMP, and dGMP (dNMP). Example nucleotides may include, without exception, any NMP, dNMP, NDP, dNDP, NTP, dNTP, and other NXP and dNXP where X represents a number from 2 to 10 (collectively NPP).

Non-natural nucleotides also referred to herein as nucleotide analogs, include those that are not present in a natural biological system or not substantially incorporated into polynucleotides by a polymerase in its natural milieu, for example, in a non-recombinant cell that expresses the polymerase. Particularly useful non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different or more when compared to the incorporation rate of a natural nucleotide. A non-natural nucleotide can be capable of being further extended after being incorporated into a polynucleotide. Examples include, nucleotide analogs having a 3' hydroxyl or nucleotide analogs having a reversible terminator moiety at the 3' position that can be removed to allow further extension of a polynucleotide that has incorporated the nucleotide analog. Examples of reversible terminator moieties that can be used are described, for example, in U.S. Pat. Nos. 7,427,673; 7,414,116; and 7,057,026 and PCT publications WO 91/06678 and WO 07/123744, each of which is incorporated herein by reference in its entirety. It will be understood that in some examples a nucleotide analog having a 3' terminator moiety or lacking a 3' hydroxyl (such as a dideoxynucleotide analog) can be used under conditions where the polynucleotide that has incorporated the nucleotide analog is not further extended. In some examples, nucleotide(s) may not include a reversible terminator moiety, or the nucleotides(s) will not include a non-reversible terminator moiety or the nucleotide(s) will not include any terminator moiety at all. Nucleotide analogs with modifications at the 5' position are also useful.

As used herein, the term "protection moiety" is intended to mean a compound or portion thereof that is attached to a reaction component to prevent the reaction component from undergoing a particular reaction. For example, a nucleic acid molecule can be bound to a nucleic acid enzyme such that the nucleic acid molecule prevents the nucleic acid enzyme from degradation or modification by a treatment that would otherwise cause degradation or modification of the enzyme. An antibody can also serve to bind a reaction component to protect the reaction component from degradation, inactivation or other reaction.

As used herein, the term "reaction component" is intended to mean a molecule that takes part in a reaction. Examples include, reactants that are consumed in a reaction, products that are created by a reaction, catalysts such as enzymes that facilitate a reaction, solvents, salts, buffers and other molecules.

As used herein, the term "repellant moiety" is intended to mean a molecule or portion thereof that will occupy a space to prevent or inhibit occupancy of another molecule at the space or to inhibit juxtaposition of another molecule near the space. A repellant moiety can act via steric exclusion, charge repulsion, hydrophobic-hydrophilic repulsion or other forces.

As used herein, the term "terminator moiety," when used in reference to a nucleotide, means a part of the nucleotide that inhibits or prevents the nucleotide from forming a covalent linkage to a second nucleotide. For example, in the case of nucleotides having a pentose moiety, a terminator moiety can prevent formation of a phosphodiester bond between the 3' oxygen of the nucleotide and the 5' phosphate of the second nucleotide. The terminator moiety can be part of a nucleotide that is a monomer unit present in a nucleic acid polymer or the terminator moiety can be a part of a free nucleotide (e.g. a nucleotide triphosphate). The terminator moiety that is part of a nucleotide can be reversible, such that the terminator moiety can be modified to render the nucleotide capable of forming a covalent linkage to a second nucleotide. In particular examples, a terminator moiety, such as a reversible terminator moiety, can be attached to the 3' position or 2' position of a pentose moiety of a nucleotide analog.

The examples set forth below and recited in the claims can be understood in view of the above definitions.

The present disclosure provides compositions useful for, among other things, nucleotide incorporation events detected in nucleic acid sequencing procedures, methods of making such compositions, and methods of using them in such procedures. The compositions and methods set forth herein are particularly useful, for example, in single molecule nucleic acid sequencing reactions, such as sequencing by synthesis. However, it will be appreciated that the compositions and methods set forth herein can be used for any other suitable detection schemes, including, but not limited to single molecule detection. Apparatuses and methods for nucleic acid sequencing in which compositions as disclosed herein may be used are disclosed in, for example, U.S. patent application Ser. No. 14/798,762, which is incorporated by reference in its entirety herein.

For example, a method of nucleic acid sequencing can include the steps of (a) providing a polymerase tethered to a solid support conductive channel; (b) providing one or more labeled nucleotides, whereby the presence of the label can be detected by the conductive channel when the label is in proximity to the conductive channel; and (c) detecting incorporation of the labeled nucleotide into a nascent strand complementary to a template nucleic acid.

In some examples of a method of nucleic acid sequencing, the polymerase is held in proximity of less than 10, 9, 8, 7, 6, 5, 4, 3, 2, or 1 nm to the conductive channel.

In some examples, a label or a portion thereof (e.g., a charge tag) may be cleaved from a nucleotide after incorporation, for example, by a polymerase.

As provided herein, the one or more labeled nucleotides may include a plurality of charge tags. For example, one or more labeled nucleotides can comprise a unique charge tag for each type of nucleotide. For example, nucleotides bearing charge tags may be used in synthesizing a strand of DNA by a polymerase according to a template sequence, which template sequence may include a string of nucleotides, including the bases adenine, thymine, guanine, and cytosine, for example. Nucleotides bearing charge tags as disclosed herein may be incorporated into a string of nucleotides complementary to the template sequence by a polymerase enzyme. As disclosed herein, as a nucleotide bearing a charge tag is so incorporated, a conductive channel may detect a charge of a given valence and magnitude specifically and differentially associated with each species of nucleotide, permitting recordation of an identity of successive nucleotides incorporated into a growing strand and thereby a sequence of nucleotides present in a template strand to which the growing strand is complementary. The charge tag can be a negative charge tag or a positive charge tag, and can have a charge anywhere from −200e to +200e, such as from −175e to +175e, or from −150e to +150e, or from −125e to +125e, or from −100e to +100e, or from −75e to +75e, or from −50e to +50e.

A conductive channel used in a method of nucleic acid sequencing can include a nanowire FET. Optionally, a conductive channel may include a carbon nanotube. A conductive channel can be part of an array of conductive channels. A detecting step can include detecting a plurality of incorporation events in succession.

Compositions, apparatus, and methods set forth herein can provide long nucleic acid sequencing reads; fast reads; high throughput capability for sequencing; and a scalable platform for sequencing. In some examples, any compromises in single read accuracy can be mitigated by performing multiple overlapping reads due to the ability of the methods and apparatus set forth herein to provide throughput in the number of reads performed in parallel.

An example conductive channel is shown in FIG. 1. Here a polymerase 1 creates a reaction site where nucleotides can be incorporated into a primed DNA template 4. The polymerase 1 is attached to a nanowire FET 2 via a tether 3. The apparatus provides single molecule sensitivity. Changes in charge distribution at the reaction site (e.g. polymerase conformation changes, nucleotide incorporation, arrival or departure of charged tags, changes in proximity of the polymerase to the conductive channel etc.) transmit to the gate and can be detected.

In particular examples, an apparatus or method of the present disclosure may use deeply scaled FinFET transistors as single-molecule conductive channels. FinFET conductive channels benefit from technology already under development by leading edge semiconductor manufacturers. Furthermore, previously published components can be used, including but not limited to (1) those used for immobilization of lysozyme on CNT to observe enzyme processivity in real time as described in Choi et al, *Science,* 335, 319 (2012), (2) those used to immobilize the Pol 1 Klenow fragment on CNT and observe DNA processivity in real time as described in Olsen et al, *J. Amer. Chem. Soc.,* 135, 7885 (2013), (3) those used to elucidate a transduction mechanism as moving charged residues due to protein allosteric motion as described in Chi et al, *NanoLett* 13, 625 (2013). The present methods can also employ the apparatus, components of the apparatus, and methods set forth in US Pat. App. Pub. No. 2013/0078622 A1. Each of the above references is incorporated herein by reference in its entirety.

Some examples of a labeled nucleotide may also include a specificity region. Thus, a labeled nucleotide may include a nucleotide, a linking molecule or linker attached to a phosphate group of the nucleotide, and a charge tag attached to the linker. A linking molecule or linker may comprise a specificity region that may hybridize to an acceptor region on a tether bound to a conductive channel. As examples, a specificity region may be any nucleotide sequence or peptide that is capable of temporarily attaching or bonding to an acceptor region on a tether. For example, a specificity region may include a sequence of nucleotides and an acceptor region may include a sequence of nucleotides such that pair bonding forms between nucleotides in a sequence of a specificity region and an acceptor region. Pair bonding in this instance refers to standard pair bonding between nucleotides, such as between a G and a C residue, or between an A and a T or U residue.

A specificity region may include a sequence of nucleotides and an acceptor region a correspondingly complimentary sequence of nucleotides. In an example, when a polymerase accepts a nucleotide for incorporation into a growing polynucleotide strand, complimentary to a template polynucleotide, a specificity region and an acceptor region may be brought into sufficient proximity to each other for pair bonding to form therebetween. Such pair bonding between a specificity region and an acceptor region may promote sufficient proximity between a charged tag and a conductive channel, promoting detection of the charge tag by the conductive channel during incorporation of the nucleotide.

In an example, a specificity region may include a nucleotide sequence including from about one nucleotide to about six nucleotides. In another example, a specificity region may further include inosine(s) flanking both sides of a nucleotide sequence. In some examples, a specificity region is included in part of a charge tag. For example, a specificity region may consist of segments or portions of a sequence of nucleotides or amino acids that are separated from each other along a linear sequence, such as by portions of a charge tag, wherein bonding to an acceptor region may induce the separate regions of the specificity region to come into proximity with each other while permitting adoption of a given three-dimensional structure by a charge tag.

In an example of a labeled nucleotide associated with a tether, specific binding affinity between a labeled nucleotide and a tether is combined with weak affinity produced by non-specific binding interactions. A labeled nucleotide may include a specificity region which is complementary to a portion of a tether. Specific binding between these regions can result from standard Watson-Crick base pairing or other non-covalent bonding. A specificity region, in this example, can also include inosines (I) flanking a nucleotide sequence. Inosines are universal bases, and thus can pair with all four native nucleotides of DNA. Additional binding interactions can result from interactions of the universal bases (e.g., inosine I) with native nucleotides on the tether. Thus, when a labeled nucleotide is bound to polymerase during incorporation, synergistic binding may occur between a specificity region of the labeled nucleotide and the acceptor region of the tether, which may greatly increase the stability of the interaction between the labeled nucleotide and the tether.

An interaction between a labeled nucleotide and polymerase, or polymerase and a tether, may cause the charge tag to come within a sensing zone of a conductive channel. Such interaction(s) may also aid in maintaining a charge tag within a sensing zone for a time sufficient for efficient and complete charge detection. Such time may be up to tens of milliseconds. Such relatively long interaction is unlike that for other labeled nucleotides present in the solution, which in theory may diffuse and briefly touch or approach the conductive channel. Such brief interaction may not be long enough for sufficient charge detection to take place, and thus in such instances, a charge tag is not detected by the conductive channel.

As disclosed herein, a charge tag may include polypeptides, oligonucleotides, oligomeric peptide nucleic acids, or any combination of two or more of the foregoing. In some examples, a charge tag may include a plurality of elements selected from amino acids, nucleotides, and linkers. Such molecules may adopt a three-dimensional structure to permit condensation of charges carried by aspects of the charge tag such that the total charge can be condensed into a smaller region. Such increased charge density may increase a charge detected by a conductive channel during incorporation of a nucleotide analog in a growing strand by a polymerase such that presence of a given species of nucleotide in such synthesis can be determined. A charge tag that adopts such a condensed conformation may minimize dispersal of its charge away from a conductive channel or over a large surface area of a conductive channel, or both. As a consequence, a conductive channel may be more likely to detect a greater amount or proportion of charge of a charge tag.

Some examples disclosed herein exploit synergistic binding of a labeled nucleotide to a polymerase, alone or in combination with a tether, in order to bring and hold a charge tag in proximity of a sensing zone of a conductive channel. Stability of a complex formed with a tether can be relatively low such that a complex does not form for labeled nucleotides that are not also bound to a polymerase (i.e., labeled nucleotides that are free in solution may not substantially bind to a tether). In other words, the off rate of such a complex can be sufficiently high that a lifetime is short. However, when a stable association is formed between a labeled nucleotide and a polymerase, a local concentration of a linking molecule may increase around a tether, thus resulting in a high on rate. In this manner, an overall association time may be greatly increased in a polymerase-associated state compared to a non-associated state. Synergistic effect of the affinities of a labeled nucleotide for a polymerase, alone or in combination with a tether, may add up to allow substantial binding affinity overall. After cleaving by a polymerase, a synergistic effect is lost and a charge tag may also dissociate from the conductive channel.

Particular examples can exploit synergistic binding of a gamma-phosphate labeled nucleotide to a polymerase and to a tether. Stability of an oligonucleotide moiety Tether, or specificity region: acceptor region, complex can be relatively low such that the complex does not form for gamma-phosphate labeled nucleotide that are not also bound to polymerase, such that gamma-phosphate labeled nucleotides that are free in solution do not substantially bind to the tether. However, a synergistic effect of affinities of a nucleotide moiety for a polymerase and a specificity region, such as an oligonucleotide moiety, for an acceptor region of a tether may add up to allow substantial binding affinity overall. In some examples, a synergistic effect can exploit a combination of specific binding affinity between a nucleotide label and tether along with weak affinity produced by non-specific binding interactions. For example, as stated above, in some examples specific binding can result from standard Watson-Crick base pairing and non-specific binding interactions can result from interactions of promiscuous bases (e.g. inosine) with native nucleotides. Thus, when a gamma-phosphate labeled nucleotide is bound to polymerase during incorporation, synergistic binding may occur which would greatly increase stability of interaction between oligonucleotide moiety and tether. After the gamma phosphate is cleaved by the polymerase, the synergistic effect may be lost and the oligonucleotide moiety will dissociate from the tether. Other types of nucleotide moiety Tether bonding, such as through non-covalent interactions between DNA, RNA, PNA, amino acids, or analogs or combinations thereof to contribute to such synergistic effect.

Figure 2:
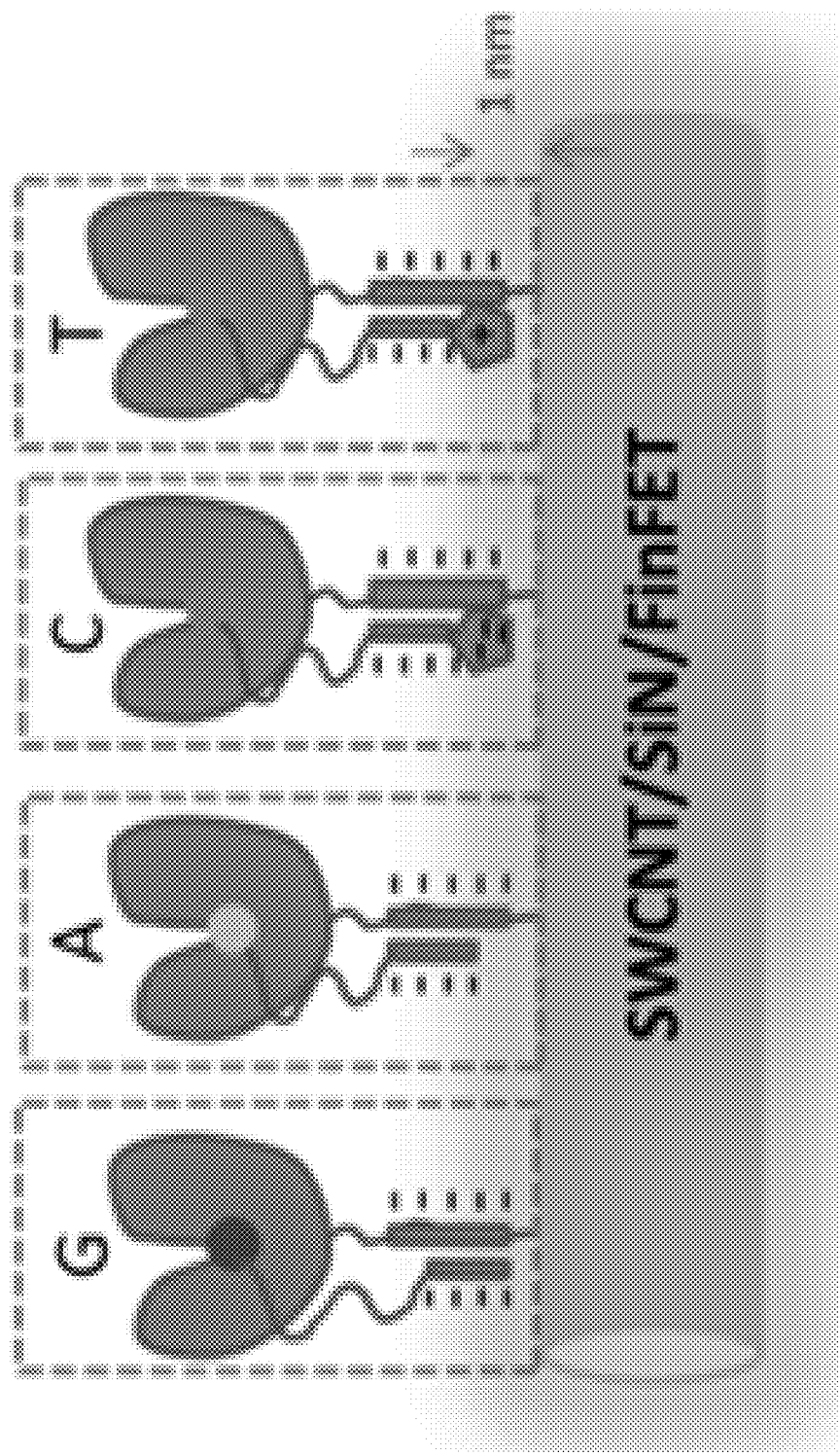
FIG. 2 shows, in one example, polymerases attached to conductive channels via nucleic acid tethers and bound to nucleotides that can be distinguished based on charge or proximity to the charge detector.

As shown in FIG. 2, a polymerase can be immobilized to a conductive channel such as a single walled carbon nanotube, silicon nanowire or FinFET. Immobilization can be via tethers that include DNA, RNA, PNA, amino acids, or analogs or combinations thereof. For convenience of demonstration FIG. 2 shows four polymerases tethered to a conductive channel, each polymerase also being bound to a different gamma-phosphate labeled nucleotide type. As shown, nucleotides may have an oligonucleotide moiety attached to the gamma-phosphate. A beta- or gamma-phosphate-labeled nucleotide that is properly matched to a template strand of a target nucleic acid may be held in place by a polymerase that may also be bound to the template long enough to temporarily hybridize an oligonucleotide moiety or other specificity region to an acceptor region of a tether (e.g. via Watson-Crick base complementarity or other non-covalent bonding). The hybridization may cause a charge tag to perturb a field around a conductive channel which may produce a detectable signal due to a change in transistor current through the conductive channel. The diagram shows a charge tag entering a field that is within 1-2 nm of the conductive channel. The properly matched beta- or gamma-phosphate-labeled nucleotide may be incorporated into a nascent strand hybridized to the template nucleic acid. This would, in turn, break the bond between the beta phosphate and the newly incorporated nucleotide. As a result, the charge tag (whether attached at the beta- or gamma-position of the nucleotide) would be free to dissociate from the tether and diffuse away from the conductive channel, thereby returning the field around the conductive channel to its unperturbed state. The appearance and disappearance of signal as the field around the conductive channel is perturbed and returned to the unperturbed state, respectively, can be correlated with incorporation of a nucleotide into the nascent strand of the target nucleic acid.

The type of nucleotide that is incorporated into the nascent strand at each position of the template strand can be determined based on unique properties of labels incorporated into each type of nucleotide. For example, four types of dNTPs can be distinguished by the position where a specificity region hybridizes to an association region of a tether, the length of the specificity region and/or the presence of a charged moiety on the label, the valence of the charge, and the magnitude of the charge. For example, a given nucleotide may have a charge of a given valence and magnitude which is not shared by other nucleotides, which have a charge with a different valence and/or magnitude. A conductive channel may be capable of detecting differences in valence and/or magnitude of a charge. During incorporation of a nucleotide with a charged tag into a nascent polynucleotide by a polymerase tethered to a conductive channel the conductive channel may detect the valence and/or magnitude of the tag of the nucleotide incorporated as the complement to a nucleotide of a template strand. When the polymerase moves on to incorporate the next species of nucleotide, in turn complementary to the next nucleotide of the template, the valence and/or magnitude of charge of such next species of nucleotide incorporated into the nascent strand may also be detected by the conductive channel. And so on as consecutive nucleotides with charge tags are incorporated into the nascent strand.

As successive charge tags are detected by the conductive channel, the differences in current flow through the conductive channel resulting from differences in charge tags may be recorded and stored such as in a computer-readable storage medium, which may be programmed so as to record a given, identified species of nucleotide for each incorporation polymerized by the polymerase as the growing nascent strand is synthesized of the basis of the valence and/or magnitude of charge detected by the conductive channel for each such incorporation.

FIG. 2 provides an example where four-state discrimination between bases G, A, C, and T is achieved using 2 charge tags and two tether hybridization positions. Specifically, dCTP is uniquely labeled with a negatively charged extrinsic moiety, dTTP is uniquely labeled with a positively charged extrinsic moiety, dATP and dGTP are distinguished from the other two nucleotide types based on absence of any extrinsic charge moiety, and dATP is distinguished from dGTP based on differential proximity of the oligonucleotide moieties to the conductive channel when they are hybridized to the tether.

Figure 3:
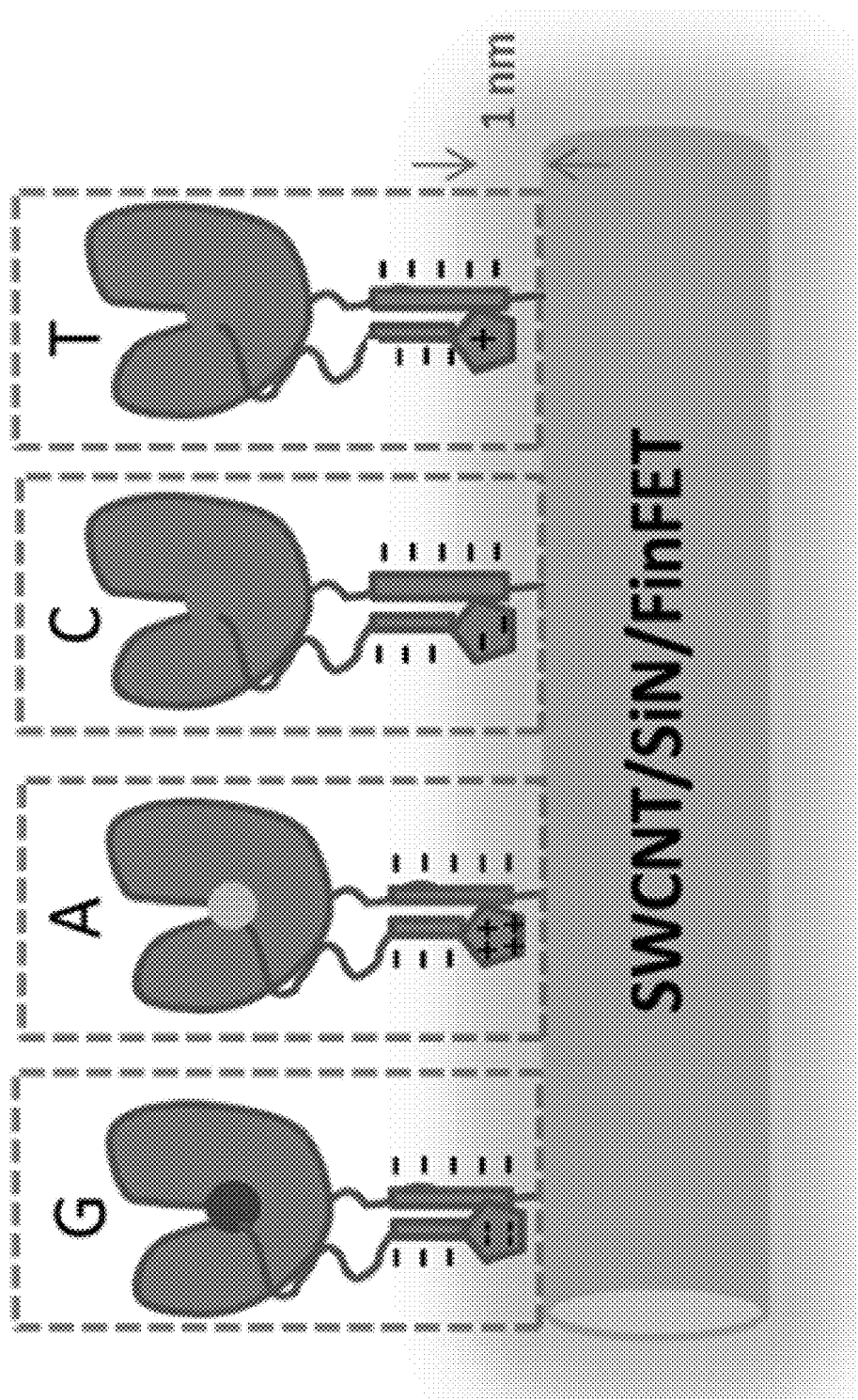
FIG. 3 shows, in one example, polymerases attached to conductive channels via nucleic acid tethers and bound to nucleotides that can be distinguished based on charge.

It will be understood that different nucleotide types can be distinguished based on any of a variety of combinations of positive charge moieties, negative charge moieties and/or tether hybridization locations. Alternatively or additionally, charge moieties used to distinguish different types of nucleotides can differ in strengths of the charges, even if the charges have the same sign. An example configuration shown in FIG. 3 provides four-state discrimination between bases G, A, C, and T based on a single tether hybridization position and four different charge moieties. Specifically, in this non-limiting example, dGTP and dCTP both contain negatively charged moieties that distinguish them from dATP and dTTP, and dGTP can be distinguished from dCTP due to charge that is distinguishably higher than the charge on dCTP. Similarly, dATP and dTTP can be distinguished from each other due to the higher positive charge on the dATP moiety compared to the dTTP moiety.

As noted previously herein, the precision of tag placement at specific hybridization positions along a tether can be enhanced through the use of a tether having ribonucleotides and a nucleotide label having 2'-O-Methyl (2'-O-Me) and 2'-Fluoro (2'F) modified RNA bases. Alternative configurations can use a tether that contains 2'-O-Me and 2'F modified ribonucleotides with label having ribonucleotides, or both the tether and label can include a mixture of native ribonucleotides and 2'-O-Me and 2'F modified ribonucleotides. Although it is possible to use a tether and/or oligonucleotide moiety that is primarily composed of RNA, it may be desirable to use a DNA-based or PNA-based or amino acid-based tether and/or oligonucleotide to avoid nuclease sensitivity that is associated with RNA. For example, a DNA-based or PNA-based tether or amino acid-based tether and/or oligonucleotide can include native ribonucleotides or non-native ribonucleotide analogs to achieve binding advantages set forth herein while reducing risk of unwanted nuclease digestion. In further examples, a tether can include one or more deoxyribonucleotides that are complementary to deoxyribonucleotides in a nucleotide label or alternatively the tether can include deoxyribonucleotides that are complementary to deoxyribonucleotides in a nucleotide label.

Figure 8:
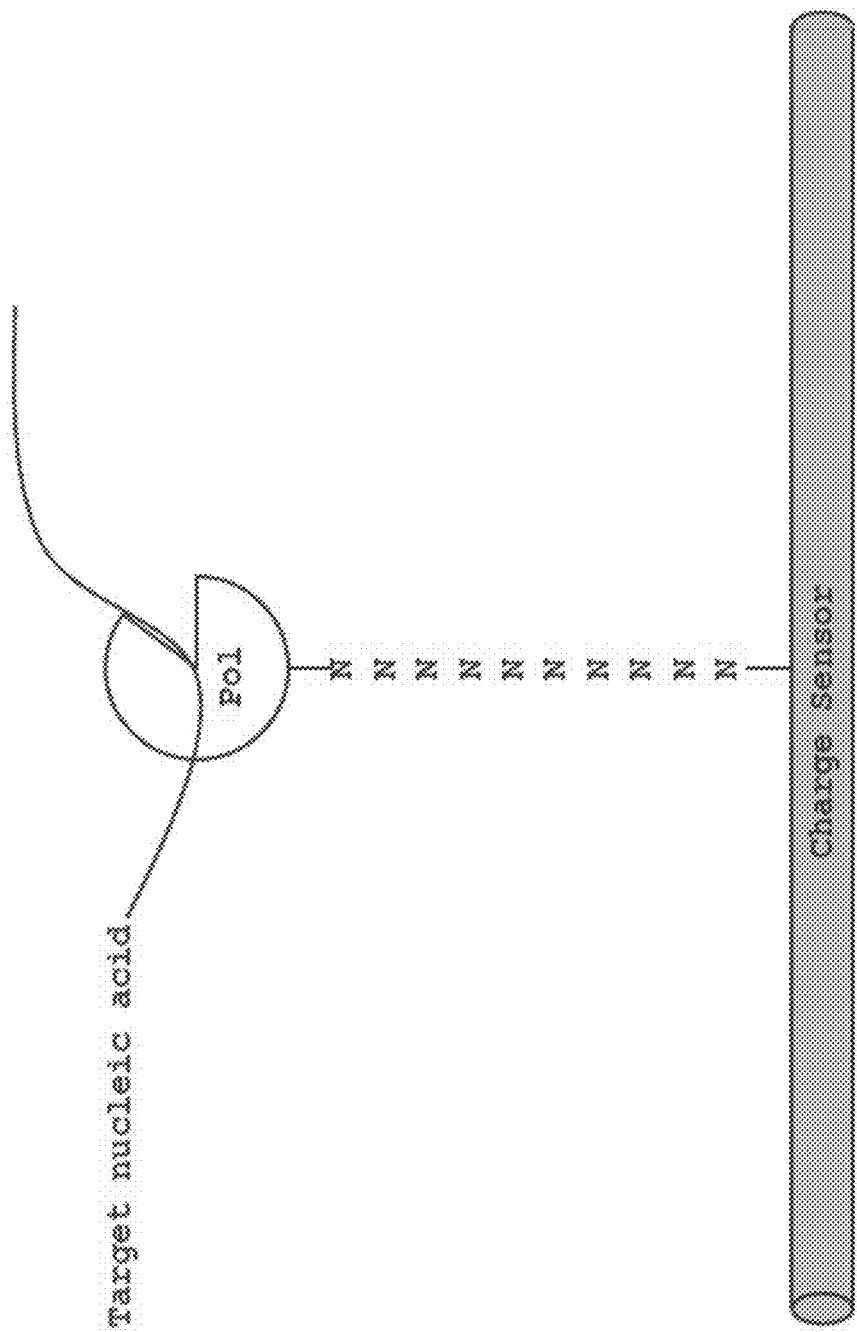
FIG. 8 shows, in one example, a conductive channel that is attached to a polymerase (Pol) via a tether having a nucleic acid sequence (generically represented as a sequence of 10 Ns). The N nucleotides are selected from universal bases and bases that are complementary to nucleotides in a linker (e.g., a specificity region) attached to a charge tag.

A tether that attaches a polymerase to a conductive channel can have different binding positions (e.g., acceptor regions) for different nucleotide sequences as set forth in several examples disclosed herein. Binding positions for two or more nucleotide sequences can overlap or they can be discrete with no overlap. For purposes of illustration, a tether sequence is depicted in FIG. 8 as a series of generic "N" nucleotides. Any of a variety of sequences can be used in accordance with rules of complementarity and desired hybridization strengths and specificities. Depending on the length of a tether, length of an acceptor region, and length of a specificity region, some, all, or no binding sites on a tether may overlap. In some aspects, the complementary bases are standard DNA bases, but any nucleotide analogs could be used (e.g., deoxyribonucleotide analogs may be used).

Figure 9:
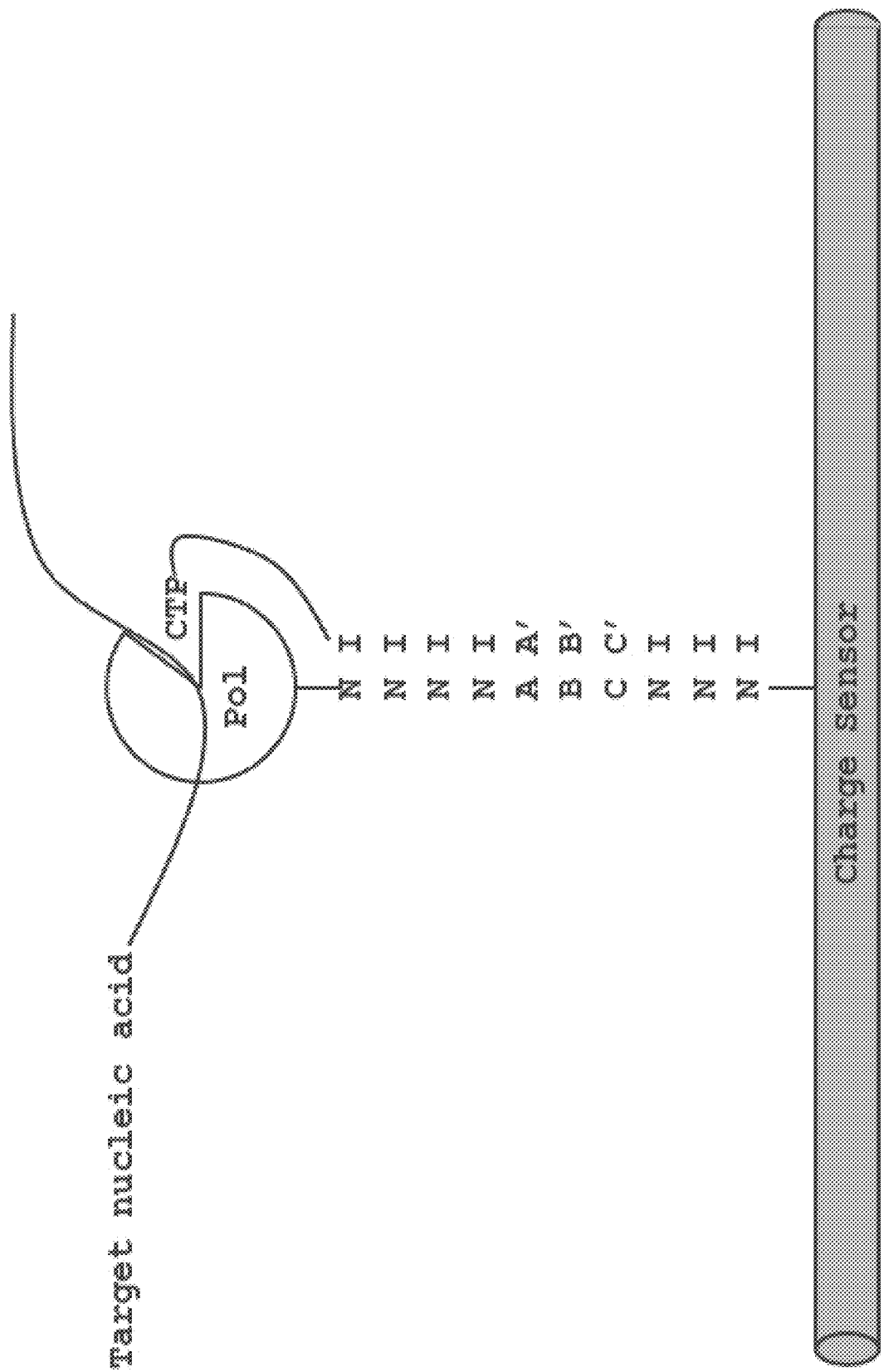
FIG. 9 shows, in one example, a conductive channel that is attached to a polymerase (Pol) via a tether having an acceptor region, in this example a nucleic acid sequence (generically represented as a sequence of 7 Ns with an ABC region; charge tag portion not shown). The polymerase is complexed to a target nucleic acid and a labeled CTP analog. The linker on the CTP analog includes a nucleic acid region having inosines (I) and a specificity region (A'B'C') that hybridizes to an acceptor region on the tether (ABC).

A tether-binding oligonucleotide moiety of a specificity region of a nucleotide analog can have a sequence of nucleotides that hybridizes specifically to a complementary sequence on a tether's acceptor region. In some examples a tether-binding oligonucleotide moiety can also include promiscuous nucleotide positions that bind non-specifically to a tether. Such positions can provide a weak interaction between the tether-binding oligonucleotide moiety and tether that facilitates the formation of a specific hybrid structure. For example, as shown in FIG. 9, an oligonucleotide moiety can include several inosines (I) that are known to bind promiscuously, albeit weakly, with all four native nucleotides of DNA. A tether-binding oligonucleotide moiety (e.g., a specificity region) and tether (e.g., acceptor region) can form a weak complex via interactions between inosines in the tether-binding oligonucleotide moiety and native nucleotides in the tether. This can allow the specific portions of the sequence (e.g. indicated as ABC and its complement A'B'C' in the figure) to associate more rapidly than they would have if required to diffuse absent formation of a weak complex. Furthermore, once a specific complex has formed inosines can provide further stability.

The non-limiting, example tether-binding oligonucleotide moieties in FIG. 9 include promiscuous nucleotide positions flanking both sides of a specific sequence. However, it will be understood that one or more promiscuous nucleotide positions can be located on only the 5' or 3' side of a specific sequence. Other examples of promiscuous nucleotide positions include those formed by degenerate oligonucleotide synthesis or those formed with other nucleotide analogs known in the art to hybridize promiscuously with 2 or more types of nucleotides.

Figure 10:
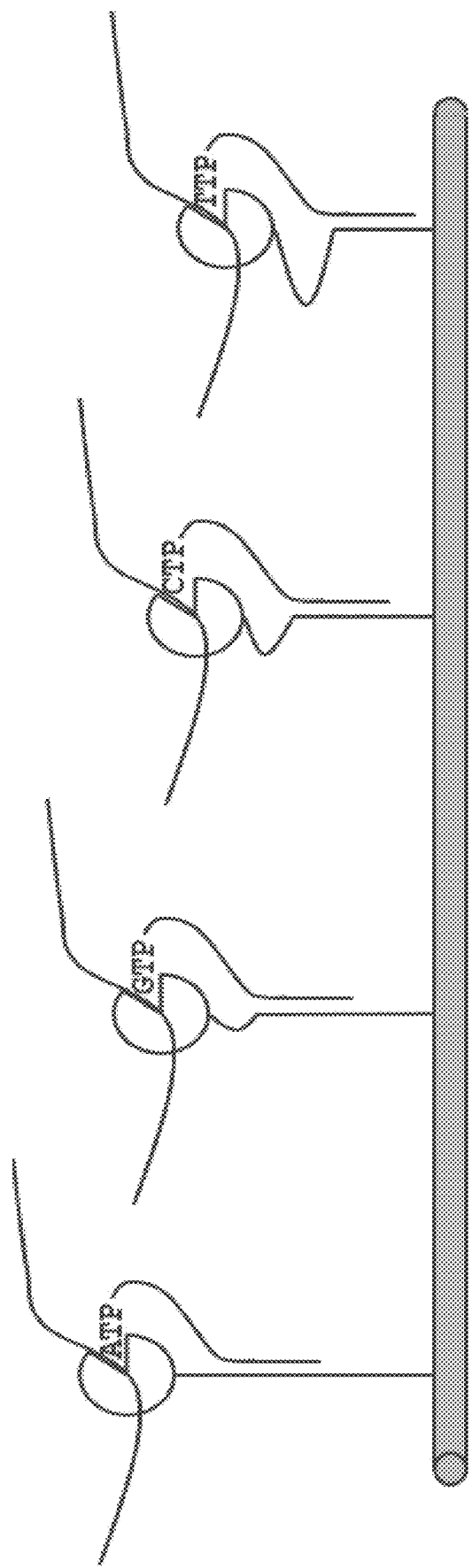
FIG. 10 shows, in one example, a tethered polymerase in four different positional states relative to the conductive channel due to the binding of each of four different nucleotide analogs through a specificity region in each linker with an acceptor region in the tether. For this illustrative example, the nucleotide analogs are identified as ATP, GTP, CTP and TTP, but any nucleotide analogs could be used (e.g., deoxyribonucleotide analogs may be used). Each of the nucleotide analogs has an oligonucleotide moiety of the same length as the other 3 nucleotide analogs, but each nucleotide analog has a specific binding sequence that binds to a different region of the acceptor region in the tether compared to the regions where the other nucleotide analog linkers bind. The charge tag, being an oligonucleotide in this example or other phosphodiester-containing charge tag in other examples, extends outside the region of hybridization at the end of the linker opposite the nucleotide.

Several examples set forth herein have exemplified the use of a plurality of different nucleotide analogs having oligonucleotide specificity regions of differing lengths. In such examples, different nucleotide analog types may be distinguishable based on different lengths of their specificity regions. Alternatively, different nucleotide analogs can have tether-binding oligonucleotide moieties of the same or similar lengths that may not permit of distinguishing one from another. However, each nucleotide analog can have a specificity sequence that binds to a different acceptor region of a tether compared to an acceptor region or regions where specificity regions of other nucleotide analogs bind. An example configuration is shown in FIG. 10 where binding of a polymerase to different nucleotide analogs places the polymerase in one of four distinguishable states. In the non-limiting example shown in FIG. 10, a tether-binding oligonucleotide moiety of an ATP analog binds to a location on the tether that is nearest to the attachment point of the tether to the polymerase, a tether-binding oligonucleotide moiety of a TTP analog binds to a location on the tether that is furthest from the attachment point of the tether to the polymerase, and a tether-binding oligonucleotide moiety of GTP and CTP analogs bind to respectively distinct locations on the tether that are at intermediate distances from the binding sites for the tether-binding oligonucleotide moieties other two nucleotide analogs. Binding of different nucleotide analogs to the polymerase may position a polymerase at different distances from a conductive channel (e.g. causing different size loops to form in the tether as shown in the figure). In examples where one or more of the nucleotide analogs includes a charge tag or other detectable moiety (e.g. extending from an end of a tether-binding oligonucleotide moiety distal to the end that extends from the nucleotide to be incorporated into a nucleotide sequence by the polymerase), the binding between the tether-binding oligonucleotide moiety and tether may position the charge tag moiety at different distances from the conductive channel. In such cases, different types of nucleotide analogs can be distinguished at least in part based on differences in signals produced for the different distances of the detectable charge tag moieties from the conductive channel. For this illustrative example, the nucleotide analogs are identified as ATP, GTP, CTP and TTP, but any nucleotide analogs could be used (e.g., deoxyribonucleotide analogs may be used).

Figure 13A:
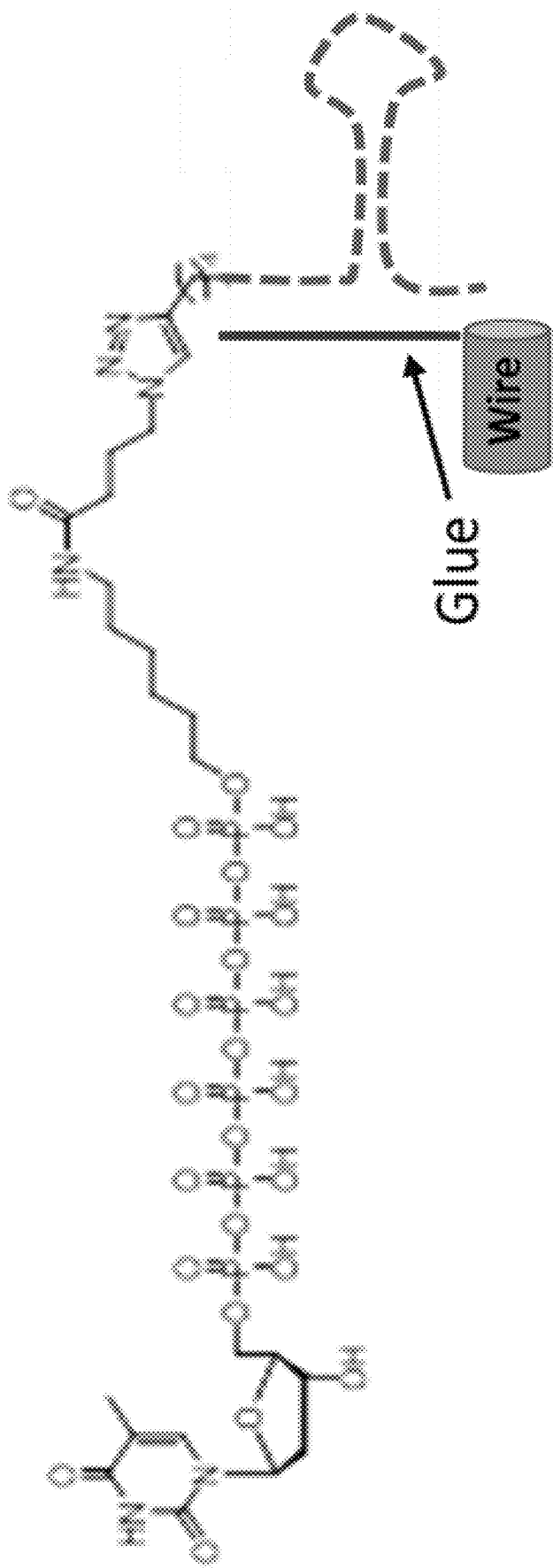
FIGS. 13A, 13B, and 13C show, in one example, several structures of a modified nucleotide with a structured oligonucleotide as a charge tag. Shown are modified nucleotides with a charge tag extending therefrom, wherein the charge tags include a specificity region bonded to an acceptor region (indicated as "Glue").
Figure 13B:
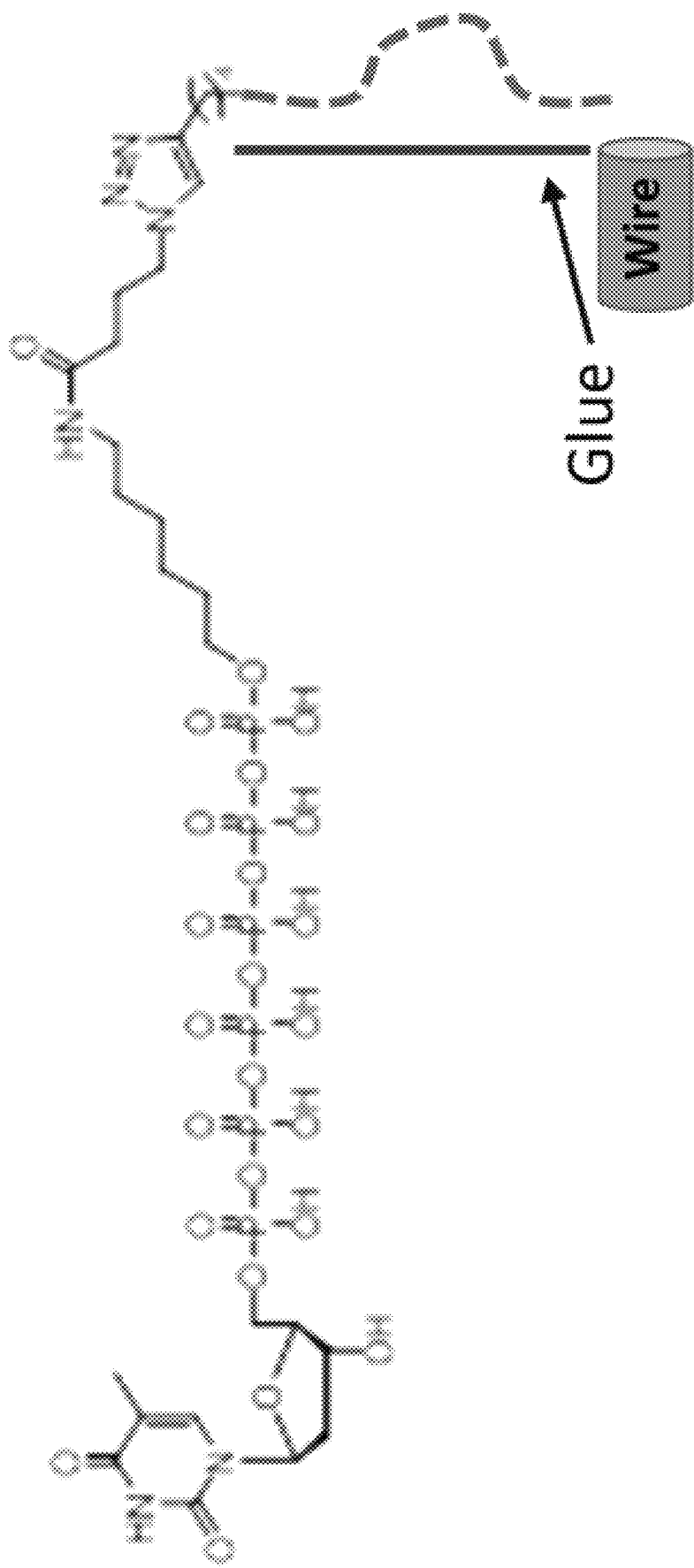

In other examples, such as illustrated in FIGS. 13A and 13B, a specificity region of a tagged nucleotide as disclosed herein may include polynucleotide sequences that each hybridize to a different section of an acceptor region of a tether. Between such sequences of the specificity region may be a span of nucleotides that do not hybridize to a portion of the acceptor region. The two sequences may therefore hybridize to the correspondingly complementary portions of the acceptor region of the tether and the intervening portion of the specificity region, with the intervening sequence free to hybridize elsewhere (such as two complimentary portions of such intervening sequence of a specificity region hybridizing to each other to form a hairpin structure as shown in FIG. 13A) or free to hybridize or itself to remain unbound specifically (such as shown in FIG. 13B). In FIGS. 13A and 13B "Glue" signifies an acceptor portion of a tether that hybridizes or otherwise transiently bonds to a specificity region of a tagged nucleotide. In some examples, such bonding may increase detection of a charged tag by a conductive channel (represented in FIGS. 13A and 13B by the wire to which the tether/acceptor region/"Glue" is attached).

Figure 4:
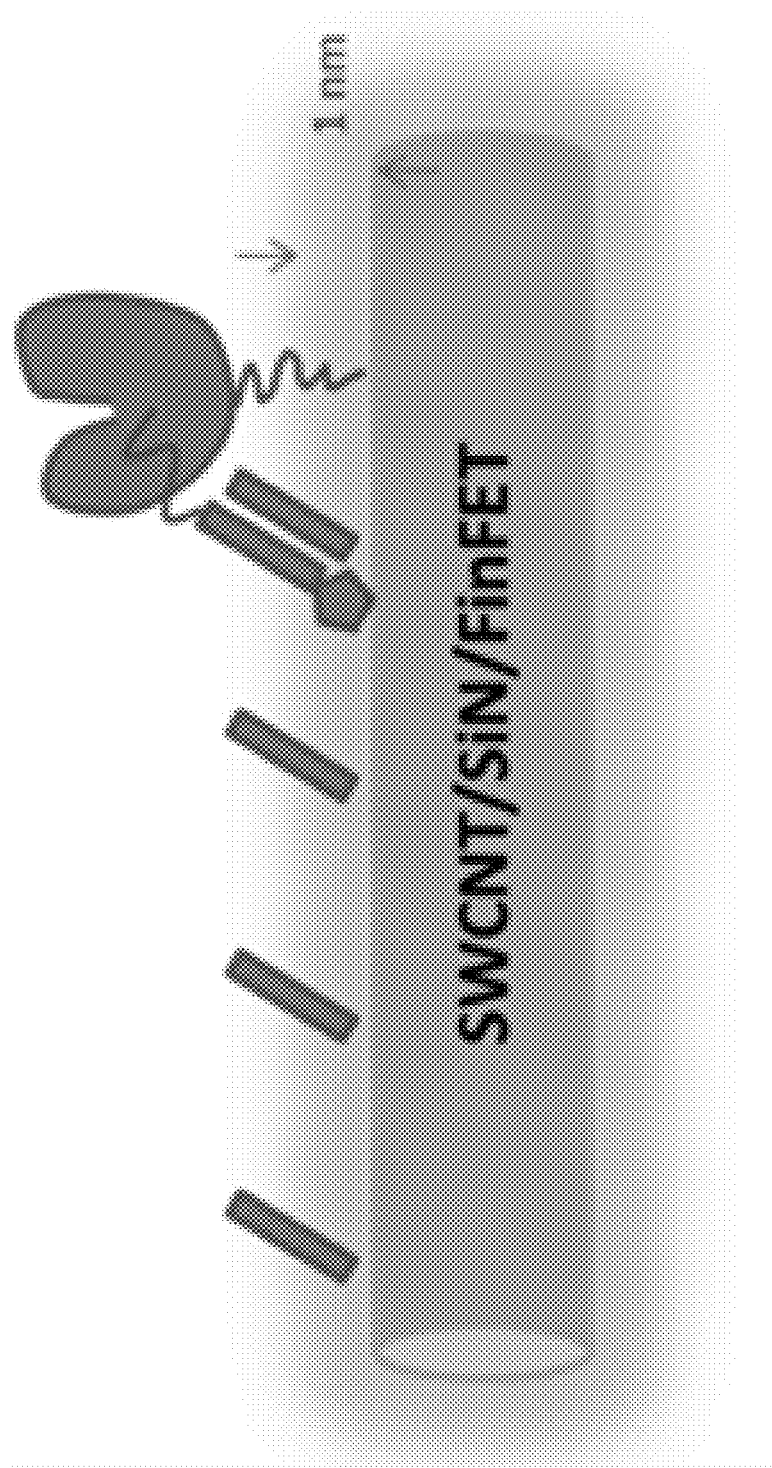
FIG. 4 shows, in one example, a polymerase tethered to a conductive channel, wherein the conductive channel is also attached to an acceptor region, including in this example a plurality of oligonucleotides capable of binding (e.g., hybridizing) to a specificity region within linkers on nucleotides.

As demonstrated by the example diagrammed in FIG. 4, a tether that attaches a polymerase to a conductive channel need not be capable of hybridizing to a charge tag or specificity sequence that may be present on an analog nucleotide. Rather, a conductive channel can be functionalized by attachment of an acceptor region separate from a polymerase's tether, to which a specificity region of a nucleotide analog may bind. Discrimination of different nucleotides can be achieved based on valence of charge of a charge tag, strength of the charge, length of a specificity region: acceptor region binding complex, or proximity or location of an acceptor region: specificity region complex formation to or in relation to a conductive channel, or a combination thereof, whether the acceptor region is part of a polymerase tether or otherwise attached to the conductive channel.

Figure 5:
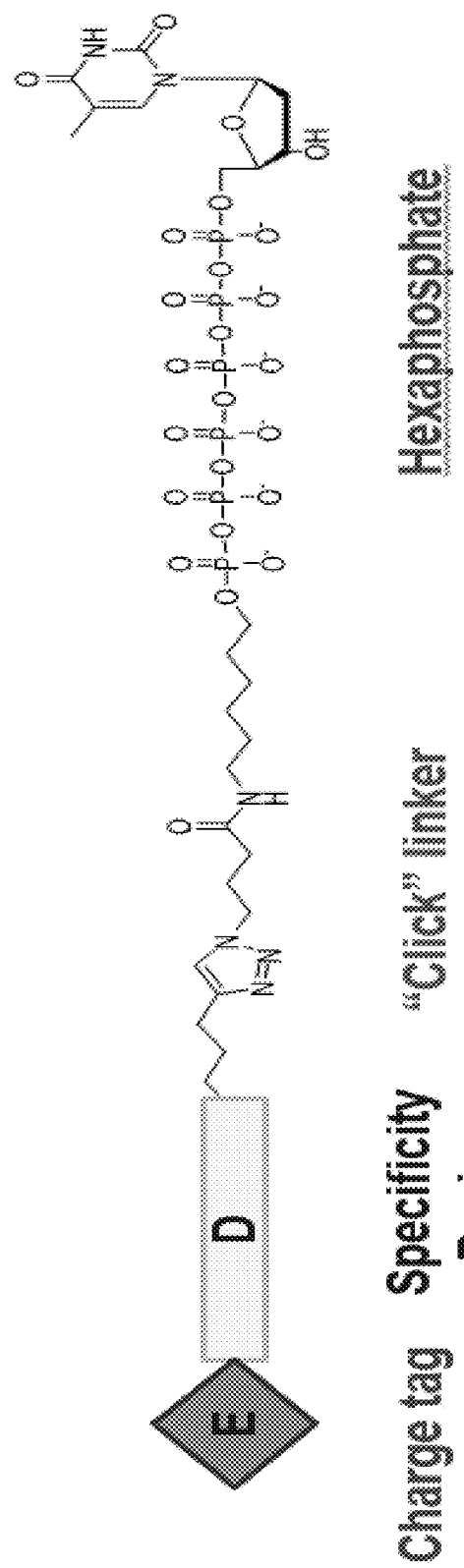
FIG. 5 shows an illustration of a non-limiting example of a nucleotide analog bearing a charge tag in accordance with the present disclosure. A nucleotide analog may include a nucleotide polyphosphate (such as dT hexaphosphate as shown), a linker region optionally comprising a specificity region, and a charge tag. In this non-limiting example, a linker includes a covalent attachment formed by azide-alkyne click chemistry. As further described below, a specificity region may be included in the linker and may assist in promoting charge tag proximity with a conductive channel during nucleotide incorporation by a polymerase.
Figure 6:
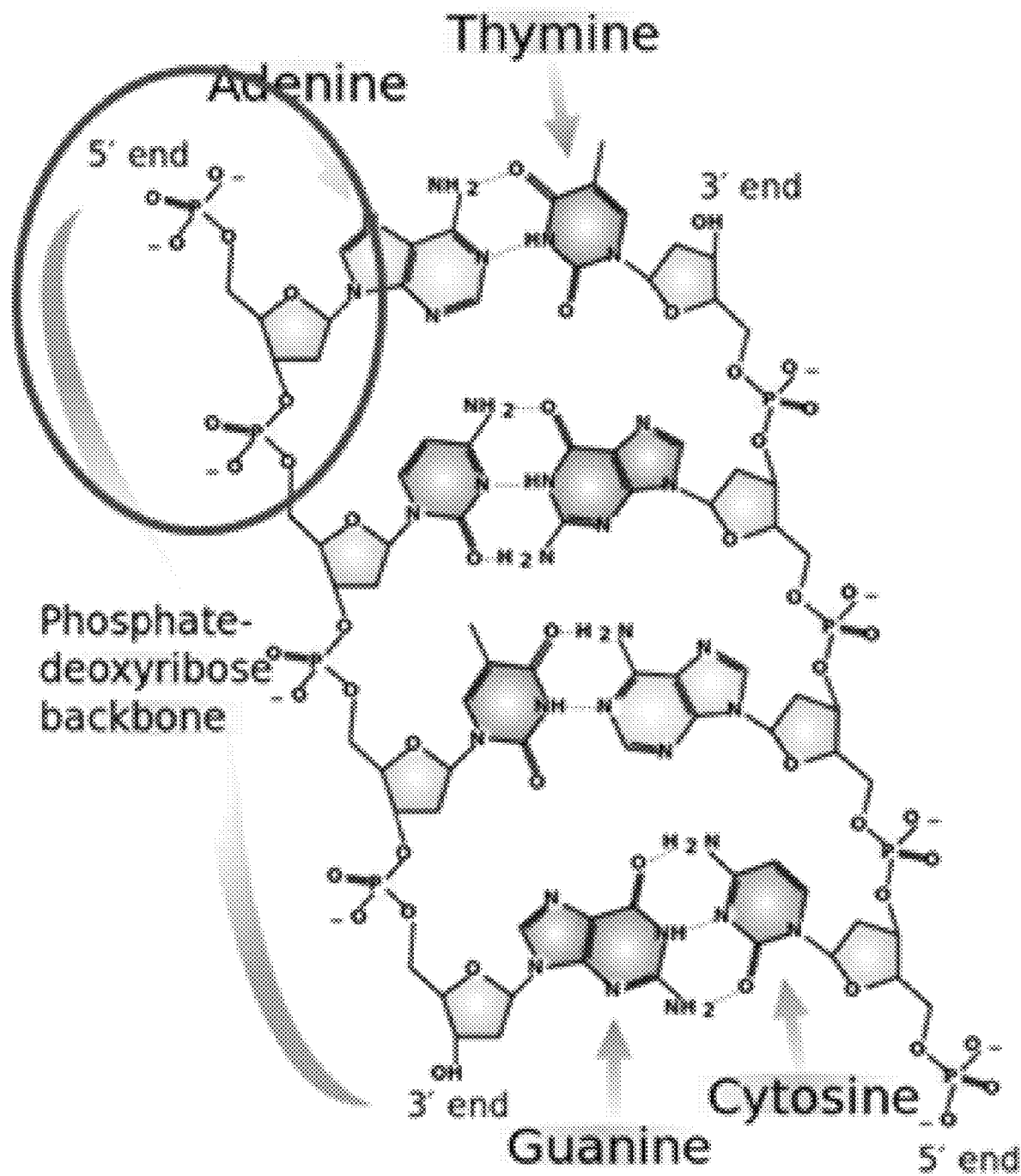
FIG. 6 shows, in one example, a nucleotide label having negatively charged oxygens in the phosphodiester backbone of an oligonucleotide moiety of the label.
Figure 7:
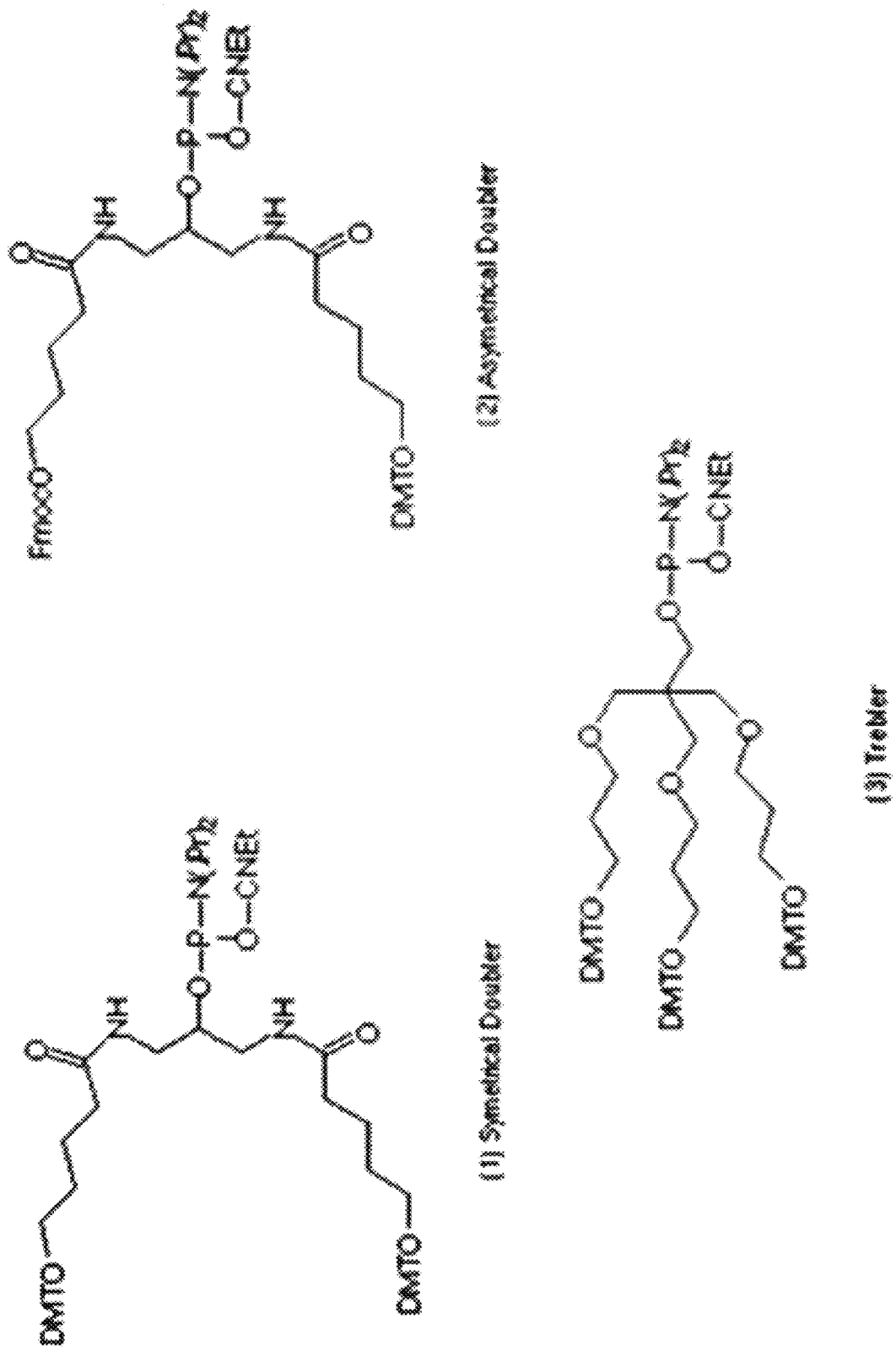
FIG. 7 shows, in one example, example multiplier units to construct branched charge tags that can be detected using a conductive channel.

An illustrative example of a nucleotide analog bearing a charge tag in accordance with the present disclosure is show in FIG. 5. This is but one of many examples of a nucleotide analog as described and disclosed herein and is not limiting of the scope of the present disclosure. In this non-limiting example, a dT hexaphosphate is connected to a charge tag via a linker region comprising a specificity region. The linker in this non-limiting example includes covalent bonds formed by an azide-alkyne click reaction, though other chemistries may be employed instead, as further disclosed herein. For ease of reference, when describing portions of a nucleotide analog herein, the region towards the right of the molecule as illustrated in FIG. 5, will be referred to as the 3' end, according to a convention of referring to a free 3' hydroxyl group on the deoxyribose of the nucleotide. Correspondingly, the region towards the left of the molecule as illustrated in FIG. 5, where the charge tag is located in this example, will be referred to as the 5' end, as an extension of a phosphate group bound to the 5' carbon of the ribose of the nucleotide.

Table I provides a non-limiting listing of some useful modifications and charges that may be used as labels in an apparatus or method set forth herein.

TABLE I

| 5' Terminus | Reagents | Final Charge State |
| --- | --- | --- |
| 5' OH | N/A | Neutral |
| 5' Phosphate | CPR 10-1900 (Glen Res.) | −2 |
| 5' Phosphate (x2) | CPR 10-1900 and symmetric doubler (Glen Res.) | −4 |
| 5' Phosphate (x3) | CPR 10-1900 and symmetric trebler (Glen Res.) | −6 |
| 5' primary amine | 5' amino-modifier 5 | +1 |

In an aspect, the present disclosure relates to a modified nucleotide including: a nucleotide; a linking molecule attached to a phosphate group of the nucleotide; and a charge tag attached to the linking molecule, wherein the charge tag includes a plurality of elements selected from the group consisting of nucleotides and amino acids, and optional linkers between elements, and wherein the charge tag comprises an internal folded or secondary structure. In an example, wherein the charge tag comprises one or more phosphodiester groups, and optional linkers between elements. In some aspects, the nucleotide is a natural nucleotide or a modified nucleotide. Modified nucleotide structures are known to one of ordinary skill in the art and may include structural modifications to the base or the sugar moiety (e.g., alkylation, amino groups, or protecting groups). In some examples, the linking molecule comprises a specificity region. In some examples, the specificity region comprises a nucleotide sequence including from one to six nucleotides. In some examples, the charge tag includes from about 1 charge to about 100 or about 200 charges. In some examples, the linking molecule comprises a structure as shown below in Formula I from —$X_2$ through the $(CH_2)_m$ group. In one example, the charge tag does not bind to a polymerase (e.g., Phi29) used in the methods herein. In some examples, the charge tag comprises a plurality of nucleotides comprising two noncontiguous regions that bind to an acceptor region in a polymerase tether, thereby forming a hairpin structure in the charge tag.

An example of a nucleotide analog, or a labeled nucleotide, is represented by a compound of the following Formula I:

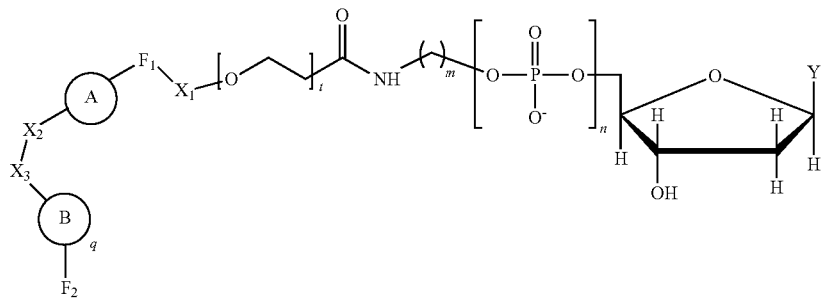

wherein n is an integer from 3 to 10, m is an integer from 1 to 10, t is an integer from 0 to 50, $X_1$ is a direct bond, a $C_1$-$C_{10}$ alkyl, a $C_1$-$C_{10}$ oxaalkyl, a $C_1$-$C_{10}$ thiaalkyl, or a $C_1$-$C_{10}$ azaalkyl, $X_2$ is $C_1$-$C_{20}$ alkyl wherein optionally one or more individual $CH_2$ residue is replaced with one or more of a peptide bond and (—O—$CH_2$—$CH_2$—)$_a$ wherein a is an integer from 1 to 24, $X_3$ is a direct bond or an oligonucleotide wherein the oligonucleotide hybridizes to an acceptor region of the tether when the label is in proximity to the conductive channel, $F_1$ is selected from a fluorophore and a direct bond and $F_2$ is absent or a fluorophore, A is

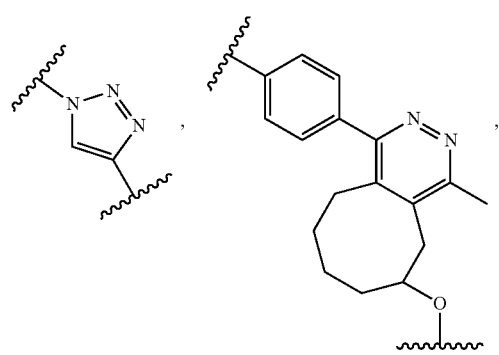

or an amide bond, and
Y is selected from

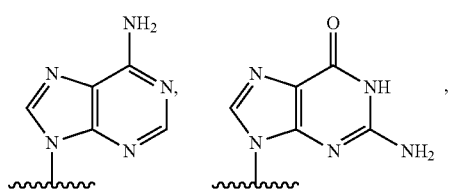 and 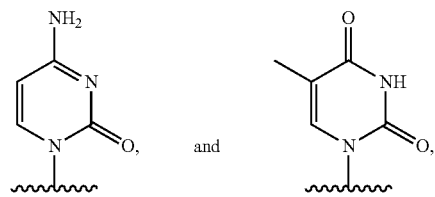

q is an integer from 1 to 100, and
B is selected from an amino acid, a nucleotide,

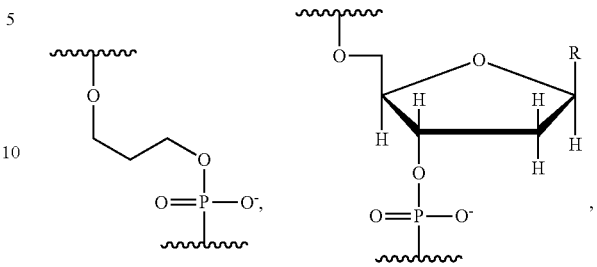

wherein R is selected from Y and hydrogen, and a dendron; and wherein q is equal to 1 when B is a dendron, and the q number of B has a charge and a charge density. In an example, provided is a method including detecting an incorporation of a labelled nucleotide into a nascent polynucleotide strand complementary to a template polynucleotide strand by a polymerase, wherein the polymerase is tethered to a solid support conductive channel by a tether, the labelled nucleotide is a compound of Formula I, and the conductive channel is to detect the labelled nucleotide during the incorporation.

In an example, B comprises a charge tag and the charge tag includes nucleotides, oligonucleotides, amino acids, peptide nucleic acids, or combinations thereof, wherein the charge tag has an internal folded or secondary structure.

As explained further herein, making a compound of Formula I may include forming A by a reaction including a linking reaction and the linking reaction is selecting from the group consisting of an azide-alkyne copper-assisted click reaction, a tetrazine-trans-cyclooctene ligation, an azide-dibenzocyclooctyne group copper-free click reaction, and a thiol-maleimide conjugation.

Also provided is a method of detecting, with a charge detector, a charge tag of a compound of Formula I, such as during incorporation of a nucleotide portion of a compound of Formula I into a nascent strand of a polynucleotide. In a non-limiting example, detecting may occur during sequencing a nucleic acid, including (a) providing a polymerase tethered to a solid support conductive channel; (b) providing one or more compounds of Formula I, whereby the presence of the compound can be detected by the conductive channel when the label is in proximity to the conductive channel; and (c) detecting incorporation of the compound into a nascent strand complementary to a template nucleic acid using the conductive channel.

Also provided is a compound of Formula I, wherein B includes one or more oligonucleotides with one or more stem-and-loop shapes, one or more cloverleaf shapes, one or more tubular shapes, one or more annular shapes, one or more cuboidal shapes, one or more cruciform shapes, one or more spherical shapes, one or more rectangular shapes, one or more pyramidal shapes, one or more diamond shapes, one or more laminar shapes, one or more columnar shapes, one or more corrugated shapes, or any combination of two or more of the foregoing. In another example of a compound of Formula I, B includes one or more polypeptides with one or more coiled shapes. Also provided is a compound of Formula I, wherein B includes one or more oligonucleotides forming a cruciform shape, one or more peptide nucleic acid molecules bonded to one or more of the oligonucleotides, and one or more polypeptides bonded to the one or more peptide nucleic acid molecules.

Also provided is a compound of Formula I wherein B has a charge of between −100e and +100e. Also provided is a compound of Formula I wherein B has a charge of between −100e and +100e and a charge density of between −100e per cubic nanometer and +100e per cubic nanometer. Also provided is a compound of Formula I wherein B has a charge of between −200e and +200e. Also provided is a compound of Formula I wherein B has a charge of between −200e and +200e and a charge density of between −200e per cubic nanometer and +200e per cubic nanometer.

In some examples, a compound of Formula I may optionally include a fluorophore, such as represented by $F_1$, $F_2$ or both. Some non-limiting examples of fluorophores include cyanine dyes (e.g., Cy2, Cy3, or Cy5), fluorescein isothiocyanate, rhodamine fluorophores (e.g., tetramethyl rhodamine), or others. Optional presence of a fluorophore in a compound of Formula I may provide additional uses such as for detection of a tagged nucleotide including a fluorophore. For example, presence of a fluorophore-containing charge tag may be detected no only through detection of a presence, valence, and magnitude of a charge carried by the tag but by methods for detecting fluorescence emission, such as fluorescence resonance energy transfer.

Also provided is a tagged nucleotide wherein the charge tag includes one or more peptide nucleic acids. In some examples, the charge tag includes one or more peptide nucleic acids, and one or more of the peptide nucleic acids is attached to one or more charged amino acids.

Also provided is a method of forming a compound of Formula I, wherein the charge tag includes oligonucleotides and is formed by DNA origami. As would be appreciated by skilled artisans, DNA origami involves folding DNA in creation of non-arbitrary shapes at the nanoscale. Compacted, origami DNA structures may permit high charge density, permitting variations in charge density in different compounds of Formula I. Higher charge, higher charge density, and greater flexibility in varying charge and charge density of a charge tag may increase probability of detection of a charge tag by a conductive channel and also permit discriminating between different charge tags detected by a conductive channel. A greater range of charges that may be carried by a charge tag allows for greater differentiation between charges carried by different examples of compounds of Formula I. In some examples, different nucleotides may be differentiated from each other by the charge carried by a tag to which they are linked as a compound of Formula I. A conductive channel may thereby be able to differentially detect different nucleotides constituting a portion of a compound of Formula I based on differences in the magnitude of the charge carried by different such nucleotides.

B may include positively charged amino acids such as arginine, histidine, and lysine, yielding a change tag with a positive charge. B may instead include aspartic acid and glutamic acid, yielding a charge tag with a negative charge. In some examples, B is a branched polypeptide, or a linear polypeptide, or a cyclic polypeptide. In some examples, B may be a single amino acid or a polypeptide with anywhere from 2 to 10, or 11 to 20 amino acids. In some examples, some of the amino acids of B may be uncharged and in other examples B may contain some amino acids that are oppositely charged from other amino acids of B, yet B may retain an overall positive or negative charge.

In this non-limiting example of Formula I, a nucleotide directly bonded to the n phosphate groups may be a nucleotide recognizable by a polymerase, and incorporated into a nucleotide sequence synthesized thereby complementarily to a template sequence. While the nucleotide analog is held in place by the polymerase during addition to a growing synthesized polynucleotide sequence, the remainder of the analog may extend therefrom and, as disclosed herein, for a polymerase in proximity to a conductive channel, a charge tag (such as represented by B in Formula I and in a charged peptide to which it is directly bound) may move or be brought into proximity with the conductive channel such that the conductive channel may sense the valence and magnitude of the charge. Different nucleotide analogs may contain different nucleotides at the 3' end of the analog, and correspondingly different peptide charge tags at the 5' end of the analog, such that a conductive channel tethered to a polymerase may detect differences in charge valence and magnitude when the polymerase associates with different nucleotide analogs to incorporate a nucleotide in a nucleotide sequence being synthesized. In these examples, a polymerase may cleave all but one phosphate group bound directly to the 5' nucleotide of the nucleotide analog such that the dNMP portion of the nucleotide analog remains in a synthesized nucleotide sequence with a 5' phosphate group free to bind to the next nucleotide to be incorporated and the cleaved remainder of the nucleotide analog free to dissociate from the complex.

A phosphate or series of phosphate groups bound directly to the 3' nucleotide may include 1, 2, 3, 4, 5, 6, 7, 8, 9, or 10 phosphate groups. Other examples may include more than 10 phosphate groups. This portion of a nucleotide analog may then be connected by an alkyl linkage including 1-10 —$CH_2$— groups. Other examples may include from 11-20 such groups at this position. In other examples, one or more of these 1-10, or 11-20, —$CH_2$— groups may be substituted by a $C_1$ to $C_{20}$ hydrocarbon.

This portion of the nucleotide analog may be further connected by 0 to 50 oxaalkyl groups, such as —O—$CH_2$—$CH_2$— groups. In other examples, one or more of these 0-50 —O—$CH_2$—$CH_2$— groups may be substituted by a $C_1$ to $C_{150}$ hydrocarbon. This portion of the nucleotide analog may be further connected to by an alkyl linkage including 0-10 —$CH_2$— groups as represented by $X_1$. Other examples of $X_1$ may include from 11-20 such groups at this position. In other examples of $X_1$, one or more of these 1-10, or 11-20, —$CH_2$ groups may be substituted by a $C_1$ to $C_{20}$ hydrocarbon. $X_1$ may also be a direct bond, a $C_1$-$C_{10}$ alkyl, a $C_1$-$C_{10}$ oxaalkyl, a $C_1$-$C_{10}$ thiaalkyl, or a $C_1$-$C_{10}$ azaalkyl, As described more fully below, A represents a linking group by which a 5' end of a nucleotide analog may be connected to a charge tag towards a 3' end of the nucleotide analog. For example, a nucleotide polyphosphate may have functional groups appended to the 5' phosphate group most distal to the deoxyribose (or ribose), at the end of which functional groups may be a reactive group. A reactive group is a chemical group capable of reacting with another chemical group-together being two reactive groups—to form a covalent bond or bonds therebetween, under controlled conditions such as in the presence of a specific reagent or reagents, or at a predetermined pH or temperature, etc. For example, compositions resembling or example of portions of Formula I from the 3' nucleotide up to or some number of bonds short of A may be commercially available or synthesized according to known methods. A reactive group may then be appended to the end of such compound such that a charge tag with another reactive group, with which the first can react to form a covalent bond, may be reacted together thereby covalently linking a charge tag to a 3' nucleotide to form a compound of Formula I.

Attached to A may be $X_2$. $X_2$ may be $C_1$-$C_{20}$ alkyl wherein individual $CH_2$ residues may be independently replaced with one or more of a peptide bond and $(-O-CH_2-CH_2-)_a$ wherein a is an integer from 1 to 24. In other examples of $X_2$, a may be an integer from 6 to 20. In still other examples, one or more of the 1-20 alkyl groups of $X_2$ may be substituted by a $C_1$ to $C_{20}$ hydrocarbon.

In an example, B may represent a charge tag connected to $X_2$ by a phosphate linkage. B may include from 1 to 100 moieties containing phosphodiester groups. In an example, B may include from 1 to 200 moieties containing phosphodiester groups. Negative charges carried by oxygen atoms in such phosphodiester groups may confer a negative charge on a B charge tag, with magnitude proportional to the number of moieties. Each of the q moieties of B may be a different moiety from any of the other moieties of B, or they may all be the same as each other. Any one or more moieties of B may be a dNMP with an adenine, thymine, cytosine, or guanosine base, for example. Any one or more moieties of B may be: a C3 spacer

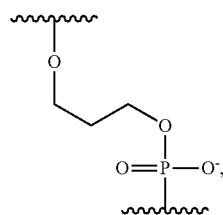

or a dSpacer

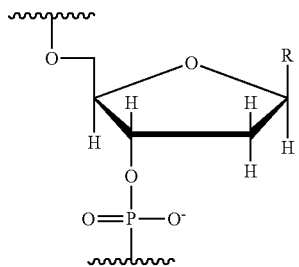

where R is hydrogen.

In some examples, any moiety of B may include any NPP (nucleotide polyphosphate). Charge tags whose charge valence, magnitude, or both differ from those of other charge tags to which different 3' nucleotides are bound permits differentiated identification of nucleotide analogs by a conductive channel as they are held by a polymerase tethered thereto during polynucleotide synthesis. In some examples, some nucleotide analogs are a compound of Formula I or similar compound as disclosed herein. In some examples, all nucleotides used in a sequencing-by-synthesis reaction contain a charged tag that includes one or more phosphodiester groups as disclosed herein, such as examples of compounds of Formula I or related compounds. In other examples, some nucleotides used in a sequencing-by-synthesis reaction contain a charged tag that includes one or more phosphodiester groups as disclosed herein, such as examples of compounds of Formula I or related compounds, whereas other nucleotides used in a sequencing-by-synthesis reaction contain a charged tag that do not include such compounds.

In other examples, each B may independently selected from arginine, histidine, and lysine, yielding a change tag with a positive charge. In another example, each B may independently selected from aspartic acid and glutamic acid, yielding a charge tag with a negative charge. In some examples, the q number of B is a branched polypeptide, or a linear polypeptide, or a cyclic polypeptide. In some examples, the q number of B may be a single amino acid or a polypeptide with anywhere from 2 to 10, or 11 to 20 amino acids. In some examples, some of the amino acids of B may be uncharged and in other examples B may contain some amino acids that are oppositely charged from other amino acids of B, yet B may retain an overall positive or negative charge. In some examples, B may include non-natural amino acids.

In still other examples, B may be a dendron of z generations comprising one or more constitutional repeating unit and a plurality of end units, wherein z is an integer from 1 to 6, the constitutional end units are selected from the group consisting of:

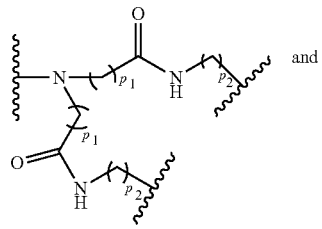

and

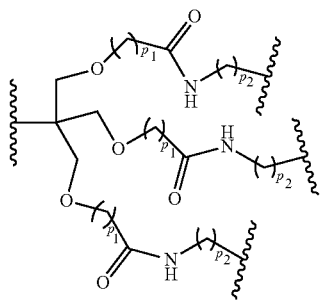

wherein $p_1$ is an integer from 1 to 3 wherein any one or more of the $p_1$ —$CH_2$— groups is optionally replaced with from 1 to 3 —O—$CH_2$—$CH_2$— groups, $p_2$ is an integer from 1 to 3 wherein any one or more of the $p_2$ —$CH_2$— groups is optionally replaced with from 1 to 3 —O—$CH_2$—$CH_2$— groups, and the end groups are selected from the group consisting of carboxylic acid, sulfonic acid, phosphonic acid, amino group, or quaternary ammonium group.

B may represent a dendron charge tag connected to $X_2$ by its free valence end. In some examples, a dendron disclosed herein may be unattached to a nucleotide analog, such as before it has been chemically bonded thereto. B may include a constitutional repeating unit with 2 degrees of branching, such as represented by the following:

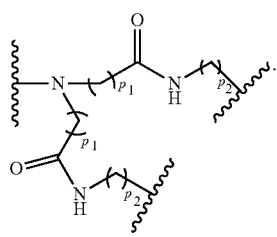

Or, B may include a constitutional repeating unit with 3 degrees of branching, such as represented by the following:

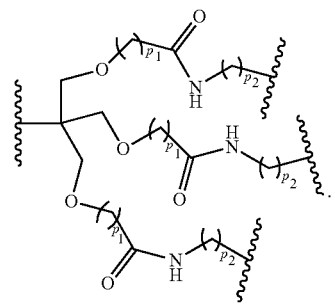

As further disclosed herein, dendron charge tags may be anywhere from 1 to 6 generations in size. End groups on terminal constitutional repeating units may be charged, either positively or negatively. Dendrons with 2 degrees of branching may therefore yield a charge tag with a charge of $2^z$ and dendrons with 3 degrees of branching may yield a charge tag with a charge of $3^z$ (where the magnitude of charge per end group is 1).

In an example where B represents a dendron, end groups may be any of a number of charged functional groups, such as, for example, carboxylic acid, sulfonic acid, phosphonic acid, amino group, or quaternary ammonium group, or any other charged functional group. In some examples, constitutional repeating units of a dendron may include a charge on an atom other than on and end group of the terminal constitutional repeating units. For example, as one non-limiting example, a constitutional repeating unit may contain a quaternary ammonium group at a branch point, which could carry a positive charge. Unlike a charged end group, which would only be present on a terminal constitutional repeating until, such internal charge may be present on every instance of a constitutional repeating unit in the dendron.

A peptide bond may be present, such as represented optionally at $X_2$ in Formula I. In other examples, in place of the peptide bond shown in Formula I, a $C_1$ to $C_{20}$ hydrocarbon may be present, or a direct bond.

For A, a linker linking a nucleotide to a charge tag may be formed by a linking reaction between reactive groups. For example, A may be formed by an azide-alkyne copper-assisted click reaction between a nucleotide with an azide (or alkyne) group and a charge tag with an alkyne (or azide) group, yielding a chemical structure such as the following or an equivalent thereof:

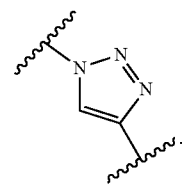 [SMILES: *c1cn(*)nn1]

Or, A may be formed by a tetrazine (TET)-trans-cyclooctene (TCO) ligation between a nucleotide with a tetrazine (or trans-cyclooctene) group and a charge tag with a transcyclooctene (or tetrazine) group, yielding a chemical structure such as the following or an equivalent thereof:

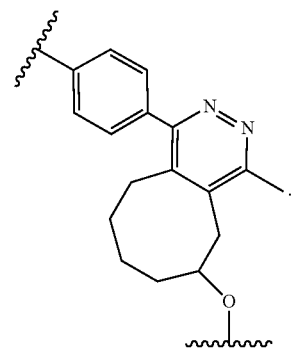 [SMILES: *OC1CCCCc2c(-c3ccc(*)cc3)nnc(C)c2C1]

Or, A may be formed by an azide-dibenzocyclooctyne (DBCO) group copper-free click reaction between a nucleotide with an azide (or dibenzocyclooctyne) group and a charge tag with a dibenzycyclooctyl (or azide) group, yielding a chemical structure such as the following or an equivalent thereof:

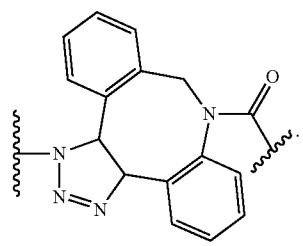 [SMILES: *C(=O)N1Cc2ccccc2C2C(N=NN2*)c2ccccc21]

Or, A may be formed by a thiol-maleimide conjugation between a nucleotide with a thiol (or maleimide) group and a charged tag with a maleimide (or thiol) group, yielding a chemical structure such as the following or an equivalent thereof:

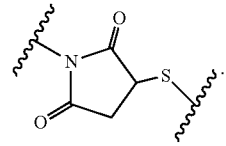 [SMILES: *SC1CC(=O)N(*)C1=O]

Or, A may be formed by an N-hydroxysuccinimide ester-amine linkage reaction between a nucleotide with an amine (or N-hydroxysuccinimide ester) group and a charged tag with an N-hydroxysuccinimide ester (or amine) group, yielding an amide bond.

As would be understood by skilled artisans, other linking groups, formed by other ligation chemistries between suitable reactive groups, may be incorporated into the present disclosure to form other structures for A by which a 3' nucleotide may be linked to a charge tag.

B of Formula I represents a charge tag. As disclosed herein, a charge tag may include polypeptides, oligonucleotides, oligomeric peptide nucleic acids, or a dendron, or combinations of at least two of the foregoing. Charges of a charge tag may be carried by charged functional groups of such moieties, such as phosphodiester bonds, amide groups, carboxylic acid groups, or other charged functional groups that may be added to such compounds such as one or more sulfonic acid, phosphonic acid, or quaternary ammonium groups. As disclosed herein, a charge tag may adopt a particular three-dimensional orientation such that the charges carried by elements thereof are held together and prevented from splaying out and away from a conductive channel. Such condensation of charge by increasing charge density of a charge tag may increase charge detected by a conductive channel.

A charge tag may be synthesized so as to have a reactive group suitable for forming a click chemistry or ligation reaction according to the foregoing. For example, a charge tag may have an azide or alkyne group (such as for covalent attachment to and inclusion in a nucleotide analog as a charge tag by an azide-alkyne copper-assisted click reaction), or a tetrazine (TET) or trans-cyclooctene group (such as for covalent attachment to and inclusion in a nucleotide analog as a charge tag by a tetrazine (TET)-trans-cyclooctene (TCO) ligation), or an azide group or DBCO group (such as for covalent attachment to and inclusion in a nucleotide analog as a charge tag by an azide-DBCO group copper-free click reaction), or a thiol (e.g., a cysteine residue) or maleimide group (such as for covalent attachment to and inclusion in a nucleotide analog as a charge tag by a thiol-maleimide conjugation). Other known ligation, click chemistry, or other covalent attachment chemistries may also be employed, with corresponding reactive groups attached to the charge tag permitting its covalent attachment to a nucleotide analog.

A peptide bond may be present, such as is shown in between A and the 5' nucleotide in Formula I. In other examples, in place of the peptide bond shown in Formula I, a $C_1$ to $C_{20}$ hydrocarbon may be present, or a direct bond.

As would also be appreciated by skilled artisans, some examples include modifications to or variations of a compound of Formula I that incorporate features discussed above related to how an acceptor region of a tether (by which a polymerase is tethered to a conductive channel) may hybridize or otherwise form non-covalent bonds with a specificity region of nucleotide analogs. For example, some portion of an analog nucleotide between the 3' nucleotide and the 5' charge tag may incorporate nucleotides, PNA residues, or amino acids capable of forming non-covalent bonds with a tether by which a polymerase is connected to a conductive channel, or to a portion functionalized with an acceptor region extending from and attached to a conductive channel that itself may not be a portion of such tether, and may also include nucleotides, PNA residues, or amino acids, or combinations thereof. The foregoing may be substituted for or added to regions of the compound of Formula I as disclosed herein between the 5' charge tag and 3' nucleotide. Such substitution or addition may contribute to a synergistic binding of an analog nucleotide to a polymerase and to a tether (or a functionalized portion of a conductive channel apart from a tether for purpose of binding to such substitution or addition) to promote association of a charge tag with a detection region of a charge detector of suitably long duration to permit detection of a charge tag to register and signify incorporation of a nucleotide analog bearing such charge, as disclosed herein.

In some examples, a charge tag's adoption of a three-dimensional structure may lead to formation of a specificity region by bringing together otherwise spatially disparate elements of a specificity region allowing for bonding of the so-assembled specify region to an acceptor region. Such specificity region formation and acceptor region binding might not occur or might be unlikely to occur or to occur only very transiently in the absence of adoption of a particular three-dimensional structure of a charge tag. In other example, the bringing together of otherwise disparate elements of a specificity region upon binding to an acceptor region may induce or promote a charge tag's adoption of a given three-dimensional conformation. In some examples, adoption of a charge tag's three dimensional conformation and the coming together of otherwise spatially distal elements of a specificity region may be synergistic such that each promotes the other. In some cases, the three-dimensional conformation so adopted by the charge tag leads to a higher charge density than would otherwise be likely to occur and may increase detection of a charge tag by a conductive channel.

Various designs of peptide charge tags can be used. Using solid phase peptide synthesis, any of the 21 amino acids can be included in a charge tag. In addition, modified amino acids are also available commercially and can be added to a peptide charge tag to further modulate its properties. Besides using amino acids with electronically charged side chains such as arginine, histidine, and lysine (positive), and aspartic acid and glutamic acid (negative), other amino acids can be incorporated in the peptide charge tag to tweak its hydrophilicity, length and size.

Figure 12A:
FIGS. 12A-12D show examples of peptide-based charge tags in accordance with aspects of the present disclosure.
Figure 12B:
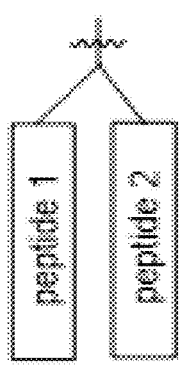
Figure 12C:
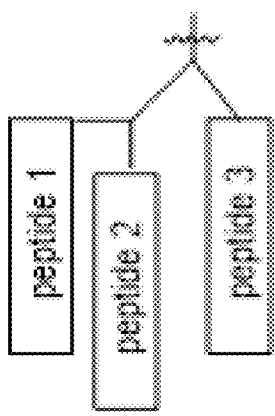
Figure 12D:
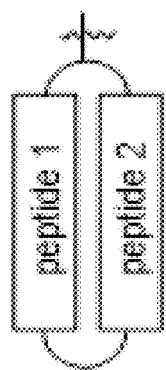

As disclosed above, in one example, a peptide charge tag may be presented in the form of a linear (see FIG. 12A), branched (see FIGS. 12B and 12C) or cyclic chains (see FIG. 12D).

By using different combination of amino acids, such as KKKKK or EEEEE (or other combinations of charged amino acids, with or without additional uncharged amino acids), of various lengths, 4 different nucleotide analogs may be distinguished for sequencing or various nucleotide analogs may be distinguished based on characteristic current signature from each peptide charge tag. Other more complex three-dimensional conformations are also possible. For example, a peptide charge tag may adopt a coiled conformation, such as an α-helix. Such a structure may include positive and negative amino acids, but an overall positive or negative charge. For example, placement of oppositely charged amino acids may induce bonding therebetween and adoption of an α-helical or other structure, wherein excess positive or excess negative charge is held together in proximity, increasing charge density. In other examples, similar bonding may promote adoption of a coiled coil structure including density of net positive or negative charge.

A charge tag may also include an oligonucleotide. An oligonucleotide charge tag may be attached to a nucleotide analog using click chemistry and ligation chemistry reactions described above for attaching a peptide charge tag to a nucleotide analog.

An oligonucleotide charge tag may adopt various three-dimensional orientations that promote compressing its charge at an elevated charge density. For example, phosphodiester bonds between nucleotides of an oligonucleotide may have a negative charge. By adopting a condensed three dimensional structure, negative charges of an oligonucleotide may be held in proximity to one another, increasing detection of such charge tag be a conductive channel. For example, an oligonucleotide may adopt well-known structures such as a step-and-loop structure, a cloverleaf structure, or a cruciform structure (such as a Holliday junction). Polynucleotide origami techniques may also be used to design polynucleotide charge tags that adopt other conformations that increase charge density. A polynucleotide charge tag may adopt a tubular shapes, an annular shapes, a cuboidal shapes, or a spherical shape. Such shapes may result in an oligonucleotide charge tag with a higher charge density that an oligonucleotide with the same nucleotide composition but not adopting the three-dimensional conformation, such as if it were stretched out into a linear conformation, would have.

For convenience and clarity, certain terms employed in the specification, examples, and claims are described herein.

Unless otherwise specified, alkyl is intended to include linear or branched saturated hydrocarbon structures and combinations thereof. Alkyl refers to alkyl groups of from 1 to 20 carbon atoms—e.g., 1 to 10 carbon atoms, such as 1 to 6 carbon atoms, etc. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, propargyl, allyl, cyclohexylmethyl, adamantyl, camphoryl and naphthyl ethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus ($C_3$-$C_{12}$) carbocycle refers to both non-aromatic and aromatic systems, including such systems as cyclopropane, benzene and cyclohexene. Carbocycle, if not otherwise limited, refers to monocycles, bicycles and polycycles. ($C_8$-$C_{12}$) Carbopolycycle refers to such systems as norbornane, decalin, indane and naphthalene.

Alkoxy or alkoxyl refers to groups of from 1 to 20 carbon atoms—e.g., 1 to 10 carbon atoms, such as 1 to 6 carbon atoms, etc. of a straight or branched configuration attached to the parent structure through an oxygen. Examples include methoxy, ethoxy, propoxy, isopropoxy and the like.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 2002 edition, ¶196, but without the restriction of 127(a)—the reference is incorporated by reference in its entirety]—it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples of azaalkyl include ethylaminoethyl and aminohexyl.

Heterocycle means a cycloalkyl or aryl carbocyclic residue in which from one to four carbons is replaced by a heteroatom selected from the group consisting of N, O and S. Heteroaryl is a subset of heterocycle in which the heterocycle is aromatic. Examples of heteroaromatic rings include: furan, benzofuran, isobenzofuran, pyrrole, indole, isoindole, thiophene, benzothiophene, imidazole, benzimidazole, purine, pyrazole, indazole, oxazole, benzoxazole, isoxazole, benzisoxazole, thiazole, benzothiazole, triazole, tetrazole, pyridine, quinoline, isoquinoline, pyrazine, quinoxaline, acridine, pyrimidine, quinazoline, pyridazine, cinnoline, phthalazine, and triazine.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, alkylsulfonylamino, arylsulfonyl, arylsulfonylamino, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxy phenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one example, 1, 2, or 3 hydrogen atoms may be replaced with a specified radical. In the case of alkyl and cycloalkyl, more than three hydrogen atoms can be replaced by fluorine; indeed, all available hydrogen atoms could be replaced by fluorine. Such compounds (e.g., perfluoroalkyl) fall within the class of "fluorohydrocarbons". To be clear, a generic term may encompass more than one substituent, that is, for example, "haloalkyl" or "halophenyl" refers to an alkyl or phenyl in which at least one, but perhaps more than one, hydrogen is replaced by halogen. In some examples, substituents are halogen, haloalkyl, alkyl, acyl, hydroxyalkyl, hydroxy, alkoxy, haloalkoxy, oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino and benzyloxy.

In describing compounds herein, the terminology "substituted with at least one oxygenated substituent" is used. An oxygenated substituent is a substituent that contains oxygen in addition to carbon and hydrogen; an oxygenated substituent may also include additional heteroatoms, such as nitrogen (for example, a carboxamide or methanesulfonyl). Typical examples of oxygenated substituents include alkoxy, hydroxy, fluoroalkoxy, formyl, acetyl and other $C_1$ to $C_6$ acyl chains.

NON-LIMITING WORKING EXAMPLES

The following examples are intended to illustrate particular examples of the present disclosure, but are by no means intended to limit the scope thereof.

Some examples of charge tags for incorporation into a nucleotide that were made in accordance with the present disclosure include the following:

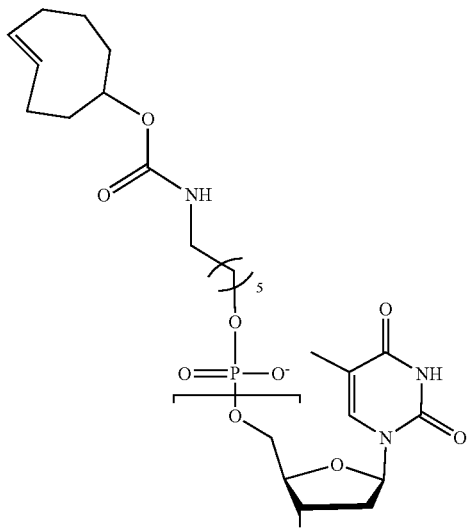

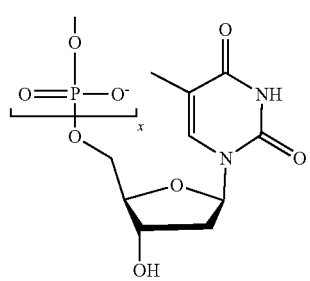

(poly-T or other polynucleotide or combination of nucleotides),

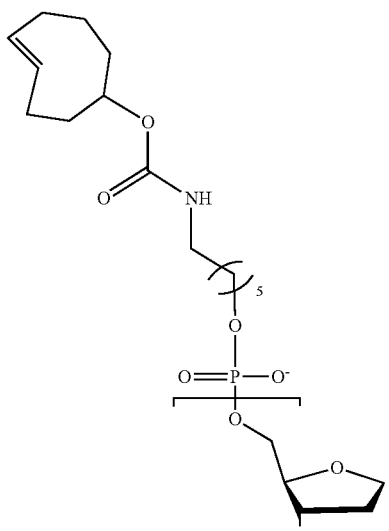

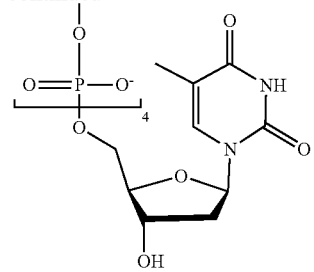

(poly dSpacer), and

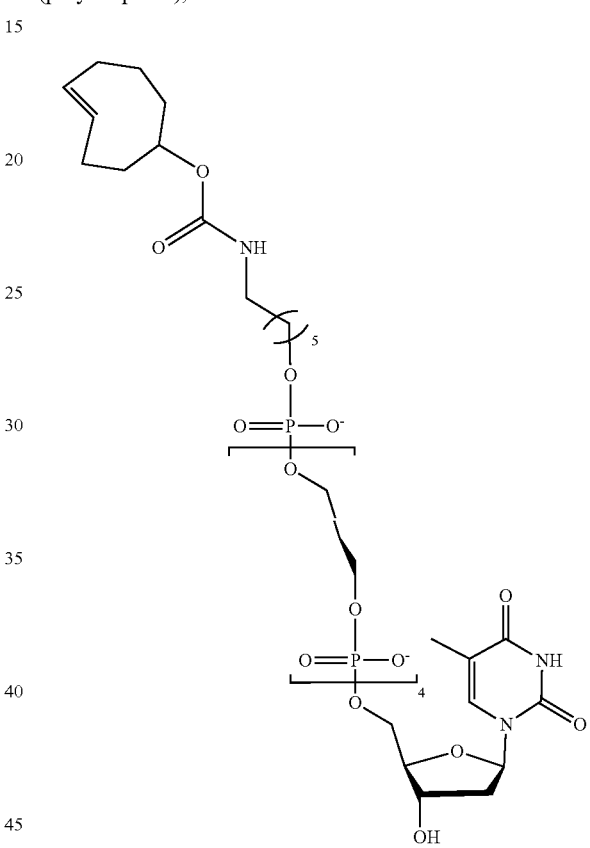

(poly C spacer), or combinations of any of the foregoing.

Charges for such charge tags may be varied by altering the number of phosphate group-containing moieties, e.g. 5, 10, 15, 20, 25, 30, 35, 40, or any number or range therebetween. As many as 40 may be included, or any number from 1 to 40. More than 40 may be included. Suitable reactive groups other than the transcyclooctene group shown in these examples may be used, in accordance with the present disclosure.

An oligonucleotide sequence can be used as a charge tag, with various lengths of charges conferred by phosphates in phosphodiester linkages. In addition, modified oligonucleotides such as dSpacer and C3 Spacer nucleotides can also be used to create charge tags with different hydrophilicity and size. An oligonucleotide sequence can be modified using different bases and hydrophobic modifications to modulate sequence specificity, minimize inhibition to polymerases and optimize interactions with the surface and linkers.

Phosphodiester based charge tags may be attached to a 5'-terminal phosphate of a nucleotide. Upon incorporation of each nucleotide by a polymerase into a growing strand during synthesis of a complement to a template strand, the charge label may be released as part of the pyrophosphate by-product. The charge on the label is detected by the detection system on the conductive channel. Based on a characteristic current signature from each tag (e.g., charge magnitude), bases incorporated into the synthesizing strand can be distinguished using differential magnitude of charge conferred by the tags.

Examples of analog nucleotides according to the present disclosure included the following, without limitation:

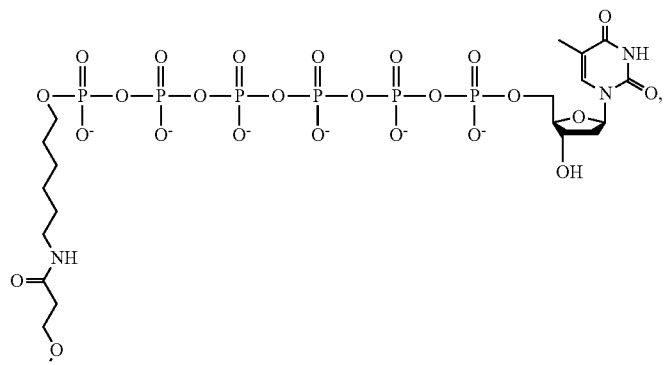

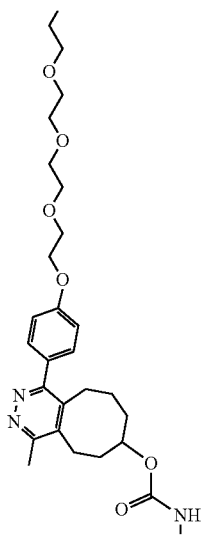

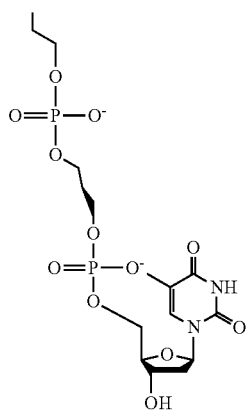

-continued
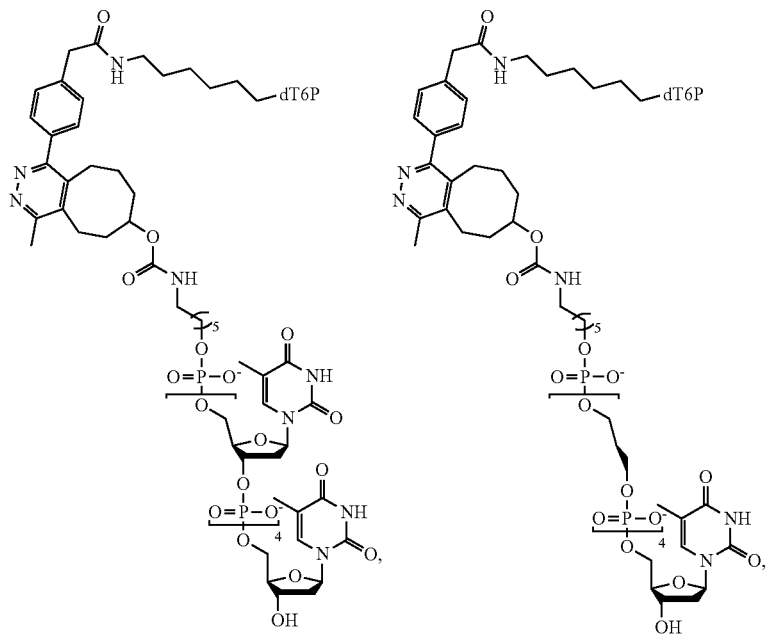
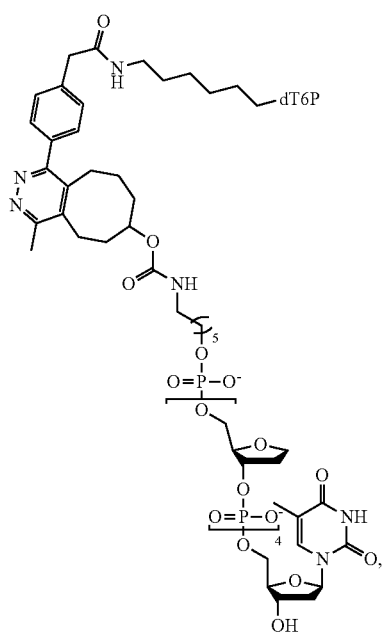

-continued
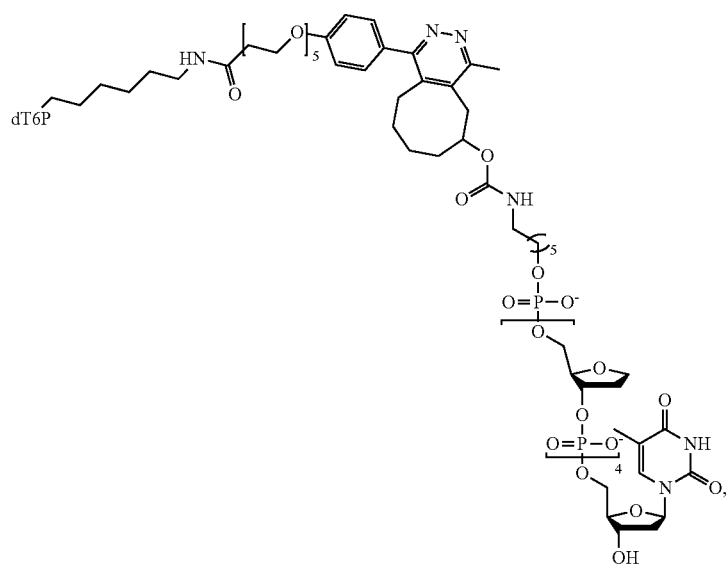
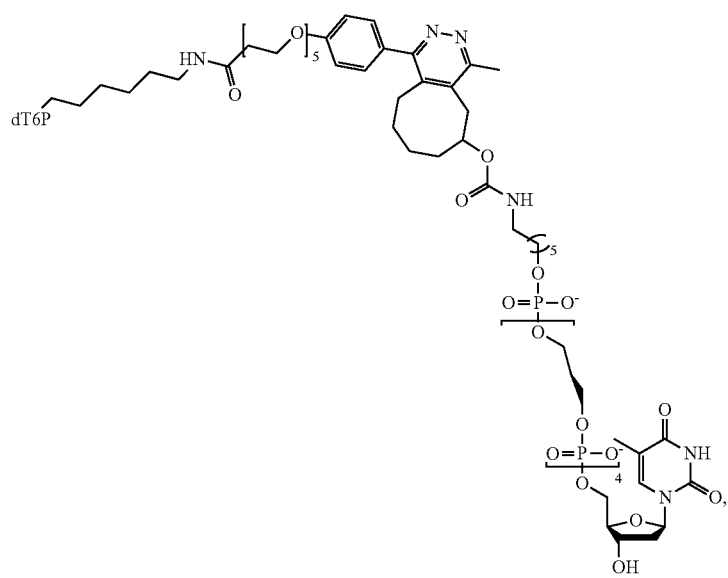
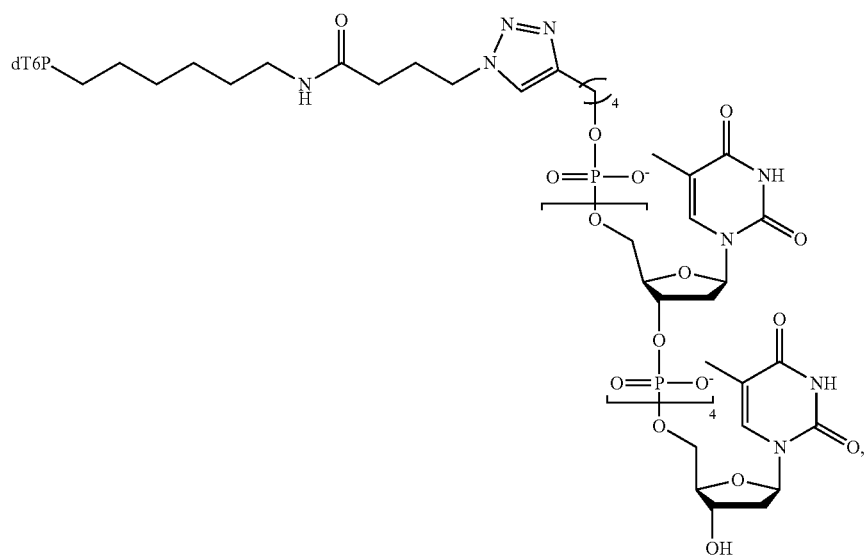

-continued

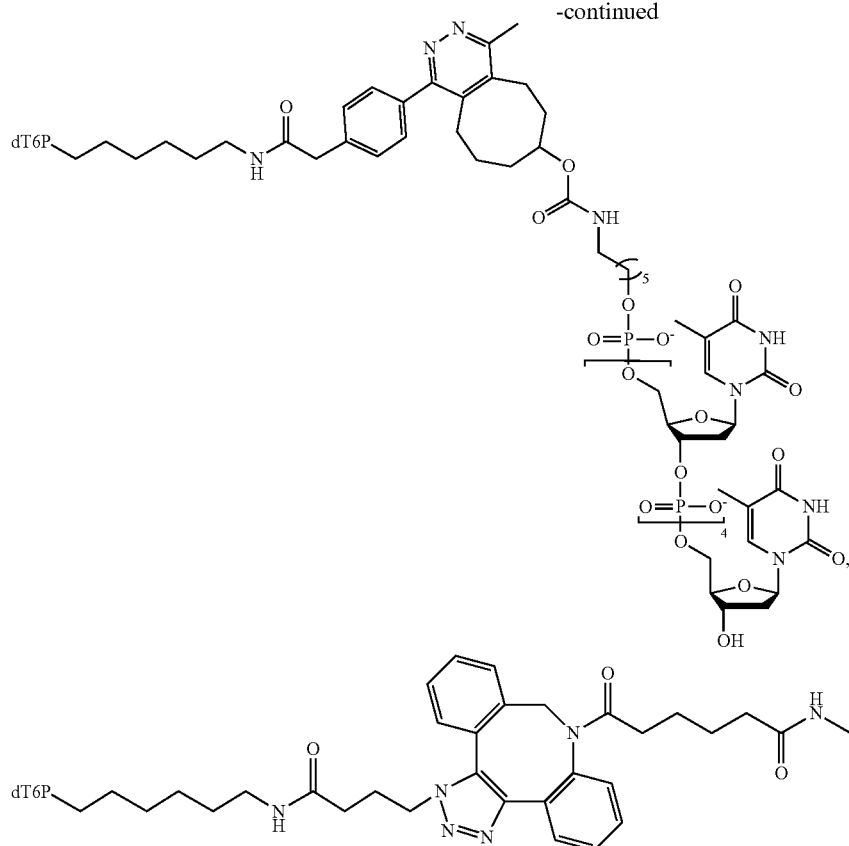

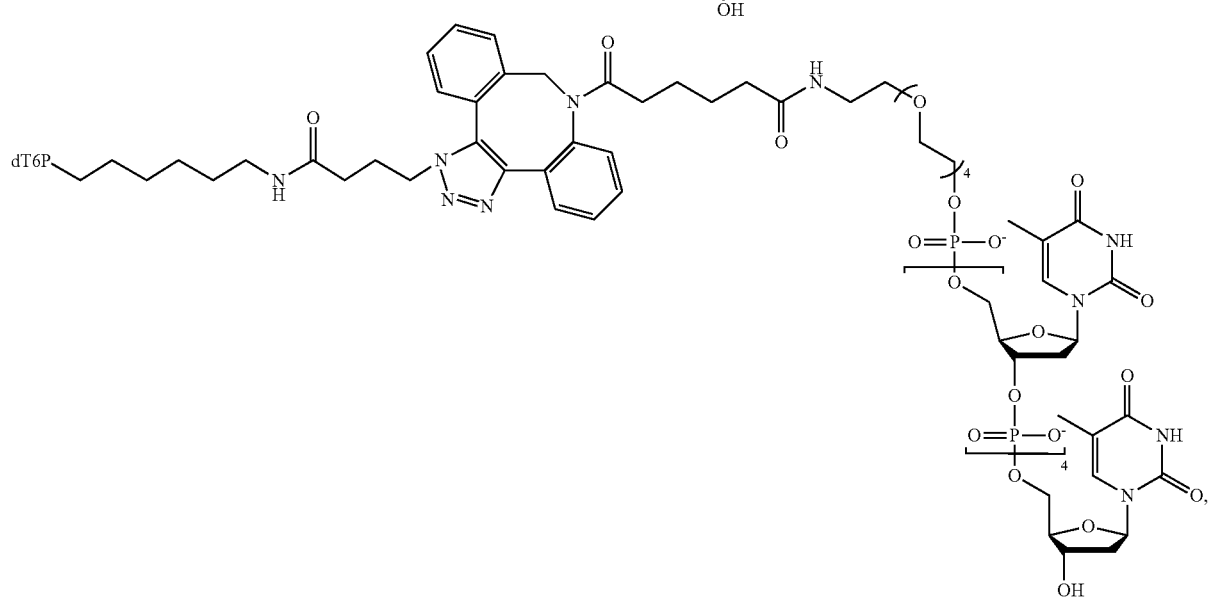

Phosphodiester based charge tags were synthesized using phosphoramidite chemistry and automated oligonucleotide synthesis. They were purified after synthesis, and then attached to a specific nucleotide via orthogonal chemistry methods. Orthogonal chemistry methods included, without limitation, copper catalyzed alkyne-azide, copper free click chemistry with DBCO and azide, TCO-tetrazine ligation, or thiol-maleimide ligation.

The non-limiting examples below show the modification of a 5' amino nucleotide hexaphosphate with various linkers to allow for orthogonal attachment chemistry to the phosphodiester charge tags. A 5'-amine deoxy-thymine hexaphosphate (dT6P) (or other NPP) (1) may be functionalized with azido-butyric N-hydroxysuccinimide (NHS) ester (2a) or methyltetrazine NHS ester (2b) to form azide dT6P (3a) or methyltetrazine dT6P (3b) respectively (Scheme 1).

Scheme 1. Functionalization of 5'-amine dT6P.
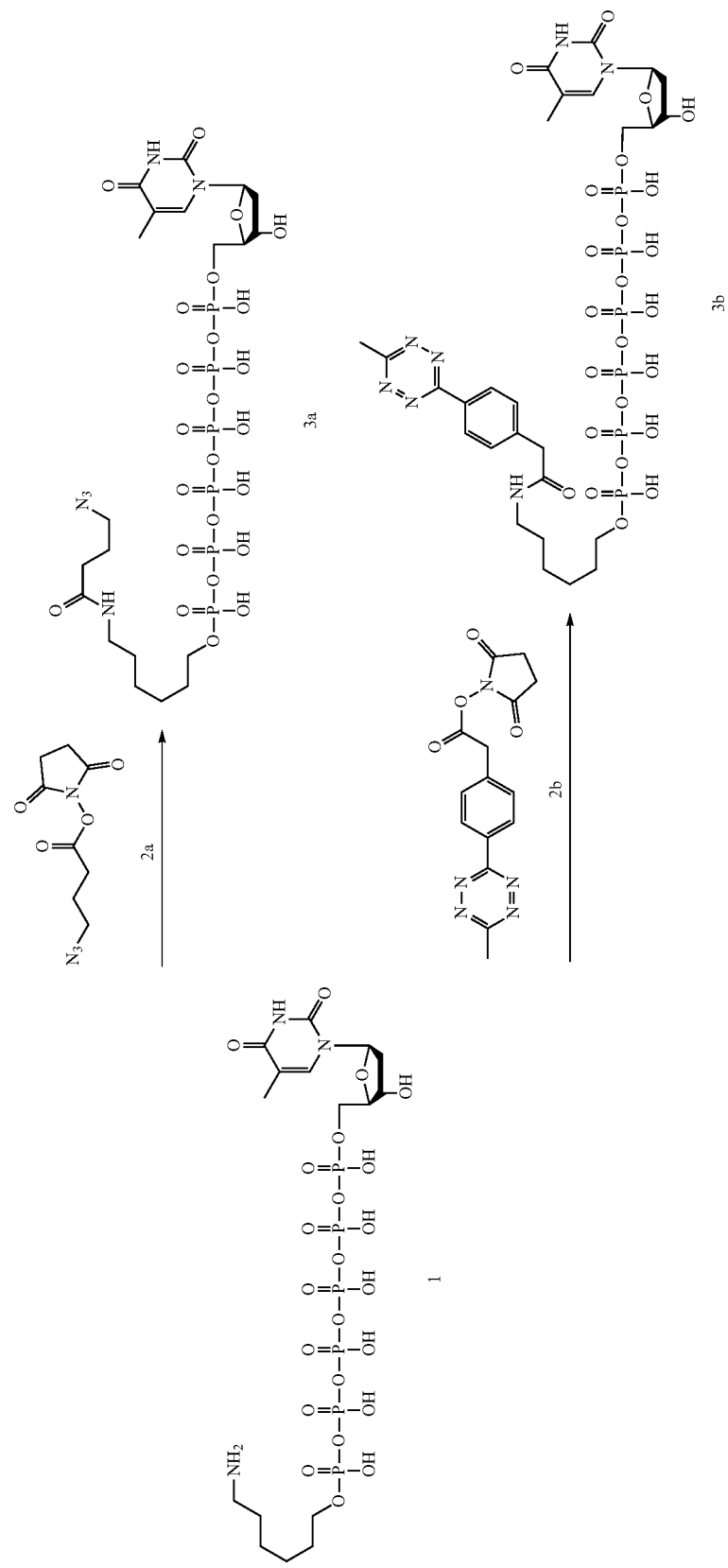

An azide dT6P (3a) may be conjugated to a linear strand of poly-T oligonucleotide (4) with a 5'-hexynyl group via copper(I)-assisted azide-alkyne cycloaddition (CuAAC) in the presence of CuSO₄, tris-hydroxypropyltriazolylmethylamine (THPTA) ligand and sodium ascorbate to form an oligonucleotide conjugate (5a). Purification was performed on C18 reverse-phase High Performance Liquid Chromatography (HPLC) and eluted with 50 mM TEAA (pH 7.5) and acetonitrile. A representative example of the CuAAC reaction with poly-T oligonucleotide is shown in Scheme 2.

A methyltetrazine dT6P (3b) was conjugated to a linear strand of poly-T oligonucleotide (6) with a 5'-transcyclooctene (TCO) group in 50 mM phosphate buffer (pH 7.4) to form an oligonucleotide conjugate (5b). The purification was performed on C18 reverse-phase HPLC and eluted with 50 mM TEAA (pH 7.5) and acetonitrile. A representative example of the methyltetrazine-TCO ligation is shown in Scheme 3.

Scheme 2. Representative CuCCA reaction.

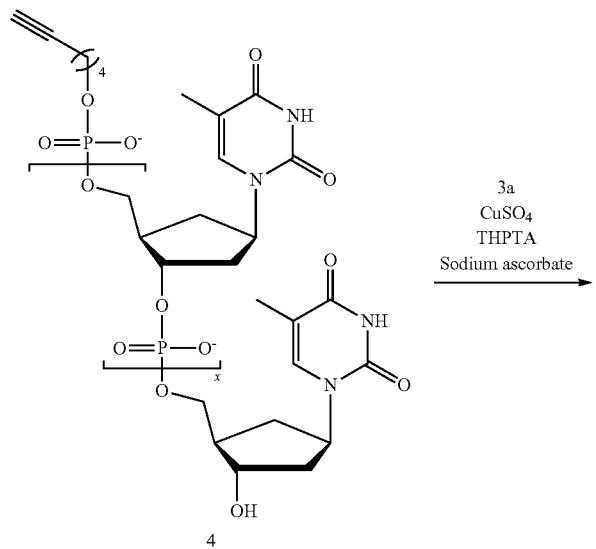

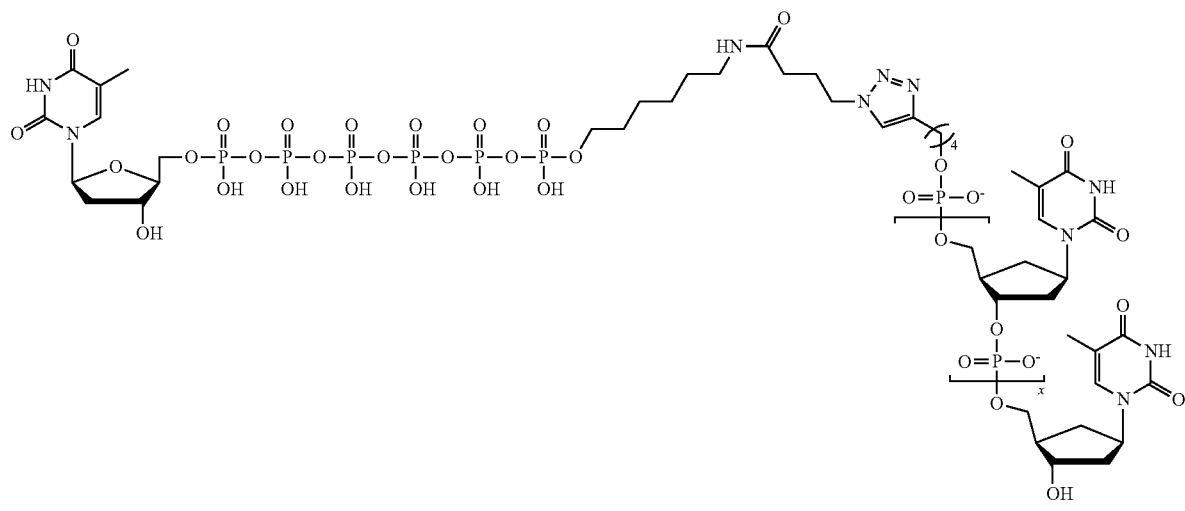

5a

Scheme 3. Representative methyltetrazine-TCO ligation.

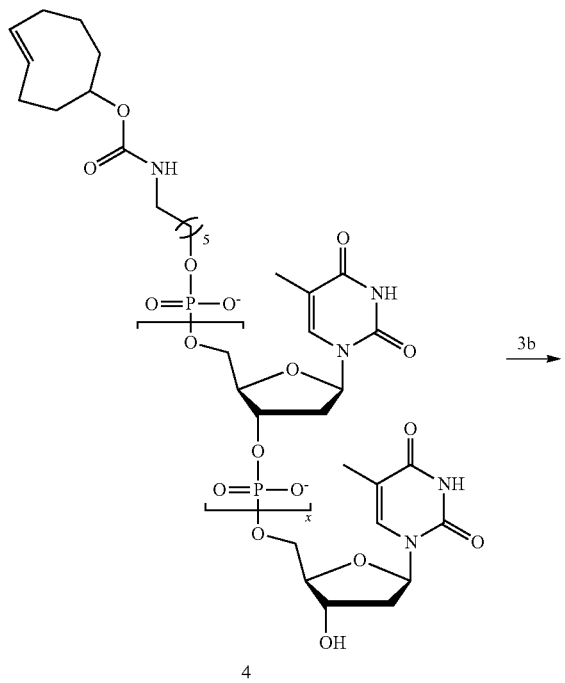

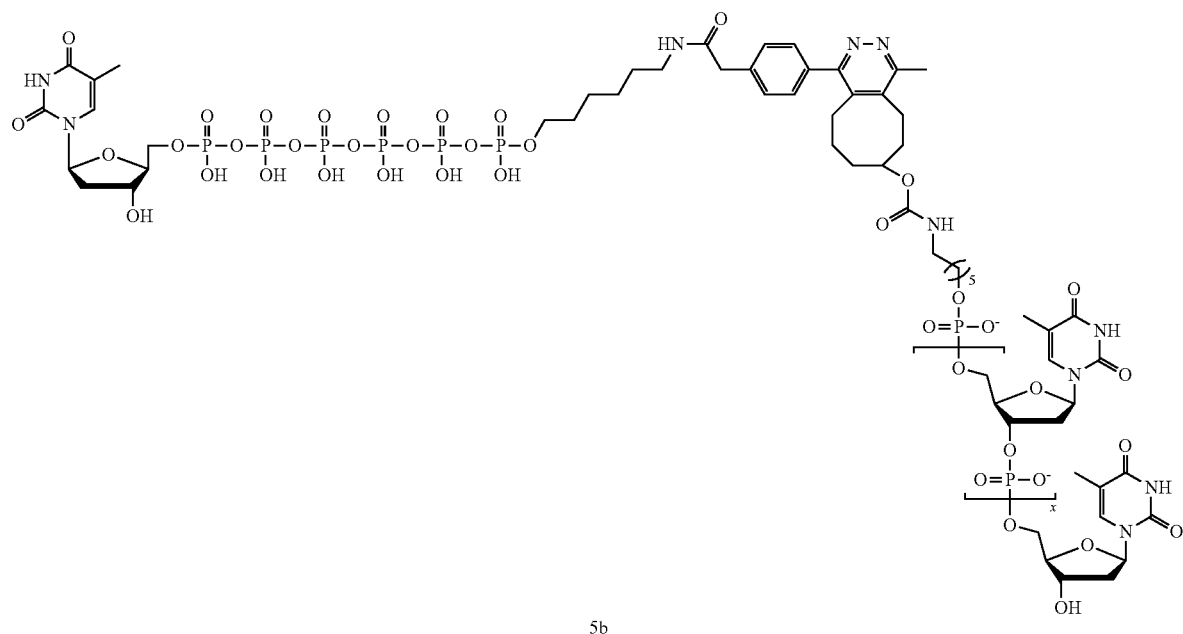

An azide dT6P (3a) was conjugated to a linear strand of poly-T oligonucleotide (7) with a 5'-dibenzocyclooctyl (DBCO) group via copper-free strain promoted azide-alkyne cycloaddition (SPAAC) in 50 mM phosphate buffer (pH 7.4) to form an oligonucleotide conjugate (5c). The purification was performed on C18 reverse-phase HPLC and eluted with 50 mM TEAA (pH 7.5) and acetonitrile. A representative example of the SPAAC reaction with poly-T oligonucleotide is shown in Scheme 4.

Scheme 4. Representative DBCO-azide conjugation.
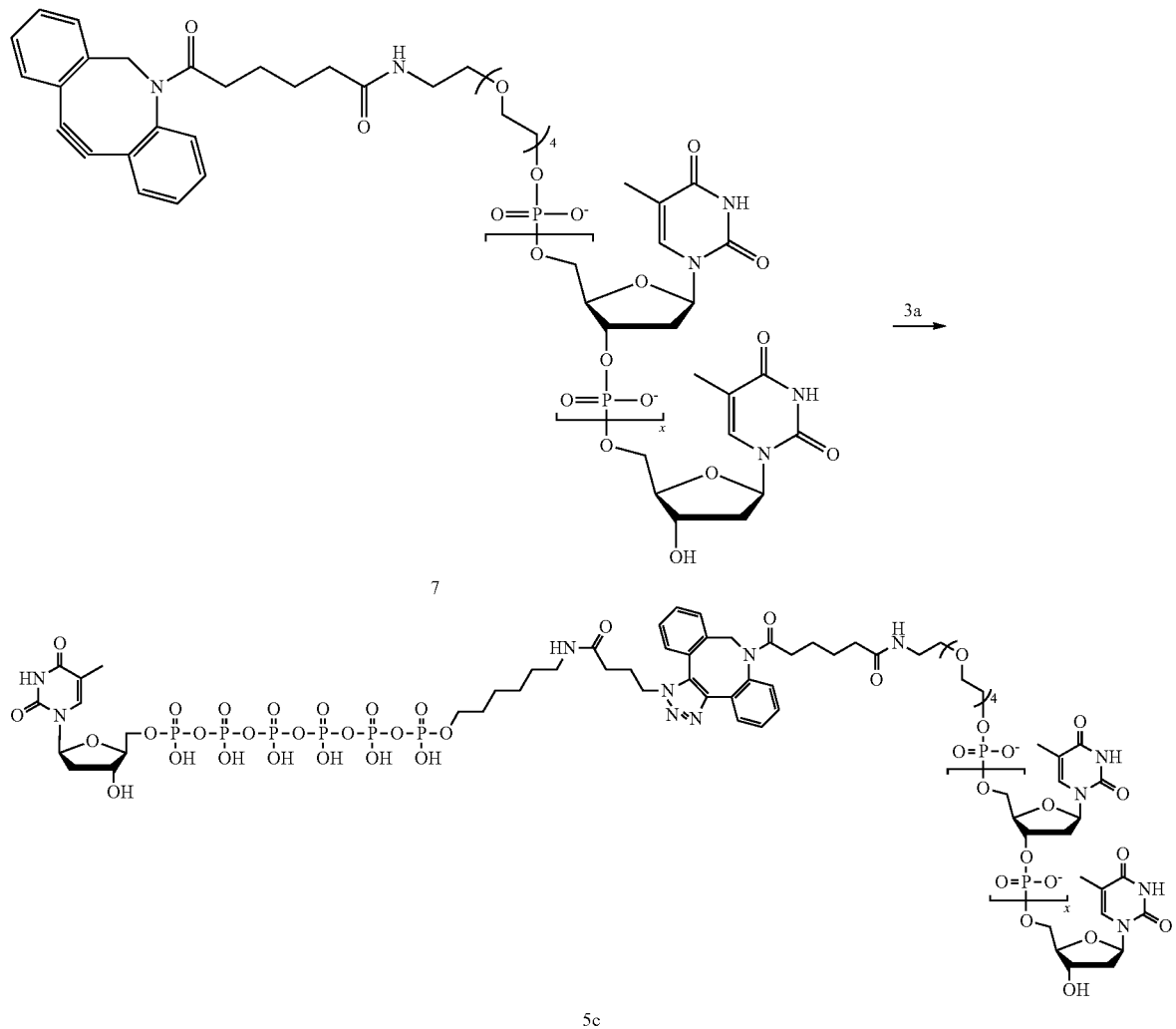
In the following scheme, an azide-alkyne click reaction linked a nucleotide polyphosphate to a charge tag:
Scheme 5. Representative conjugation by click chemistry.
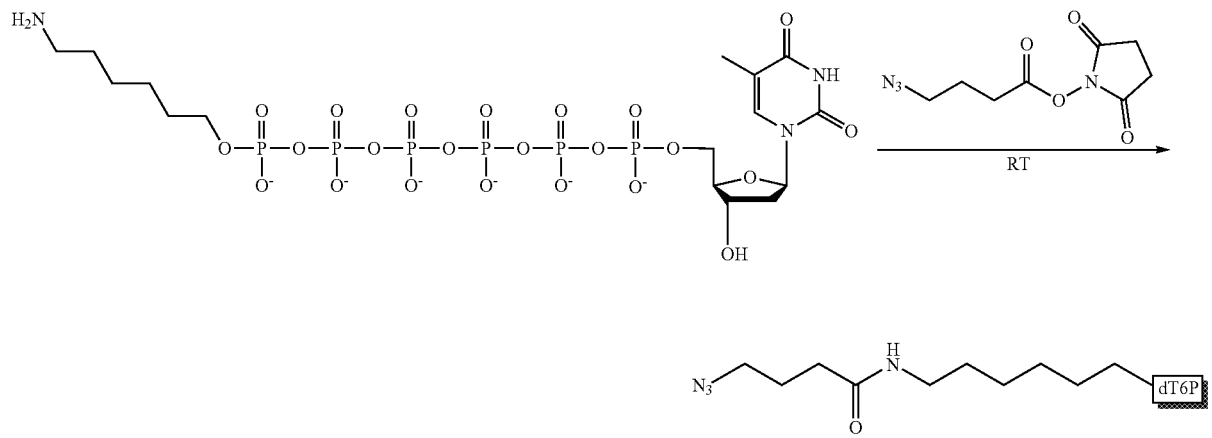

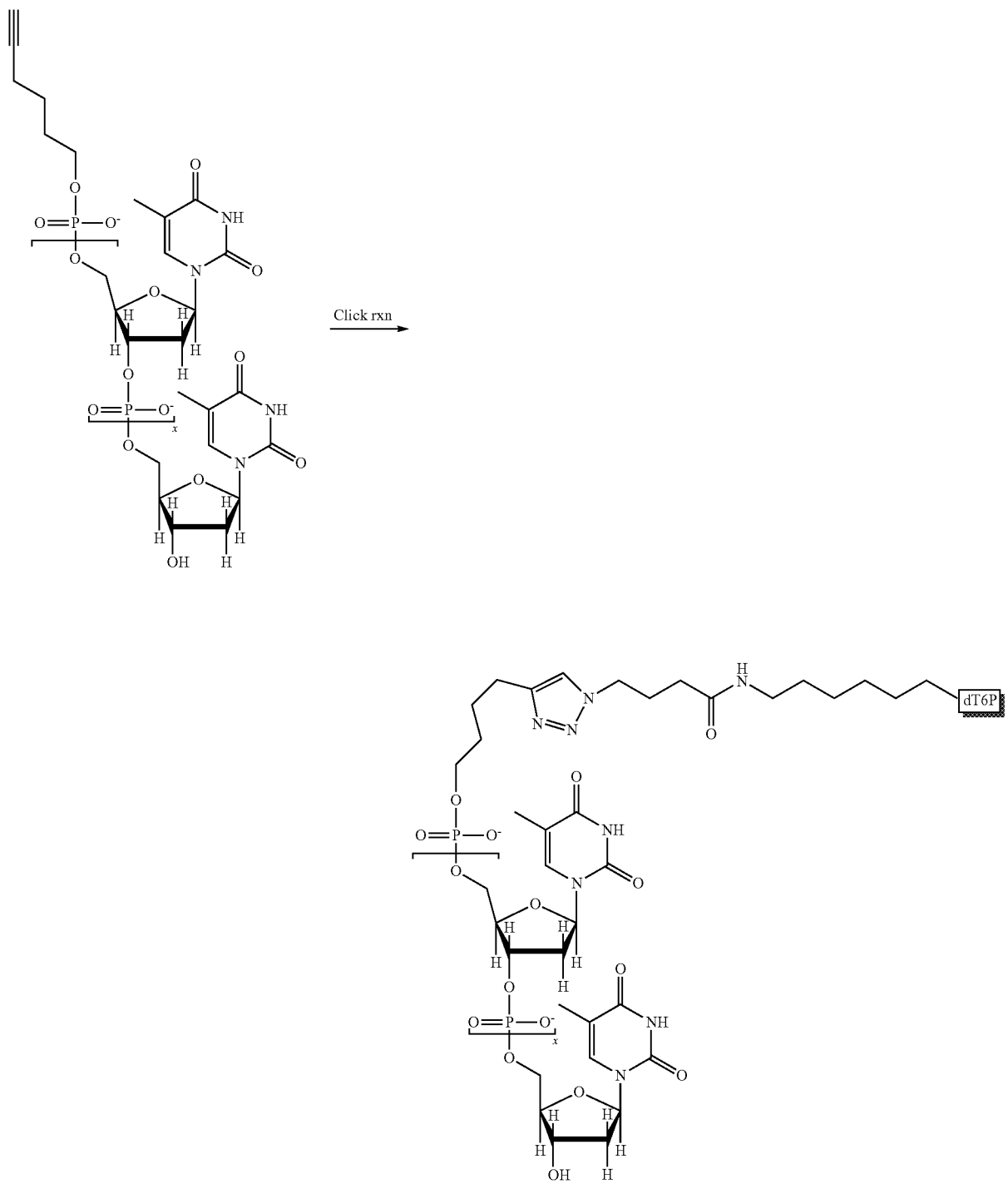

As would be appreciated by skilled artisans, the foregoing examples may be modified, such as by reversing the placement of each reactive group of a ligation reaction or click chemistry reaction, yielding the foregoing linkages but oriented in the opposite direction with regard to the 5' and 3' ends of the analog nucleotides.

Reactive groups and linker chemistries may be appended to nucleotides and charge tags according to various applicable chemistries in accordance with the present disclosure. In some non-limiting examples, an azide or methyltetrazine tail may be added to an aminated NPP by reaction with an appropriate NHS residue, which may include linker portions of various lengths such as PEG4 linker, or PEG linker of varying lengths. Non-limiting examples of such synthesis schemes include the following and variations thereof:

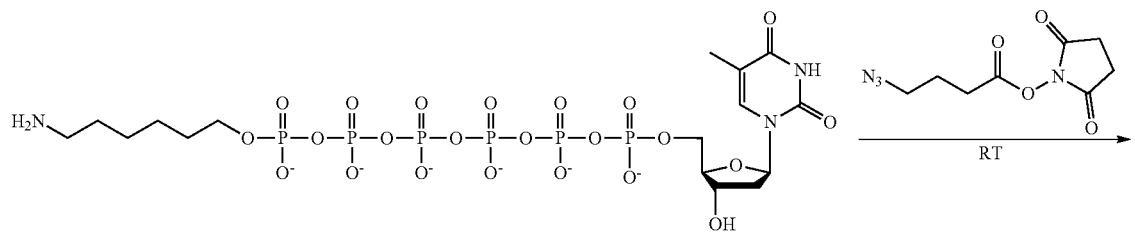
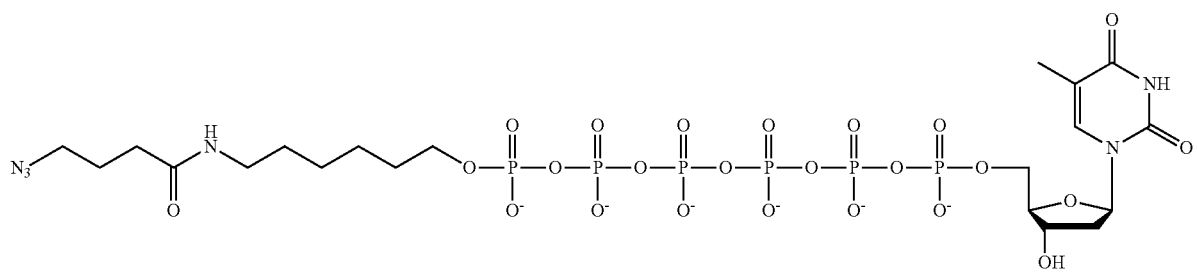
Different NHS-moieties were used to add an azide or methyltetrazine reactive group, and with various linker lengths. Non-limiting examples include:
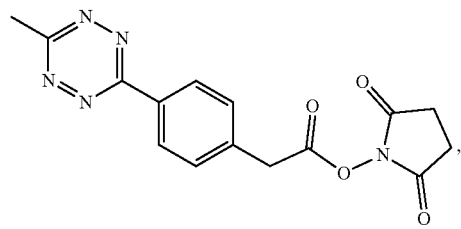
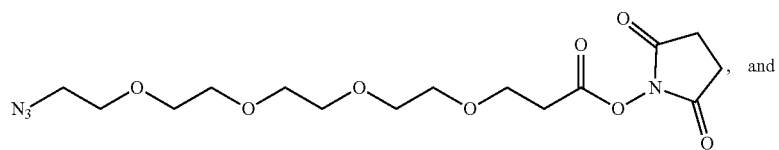
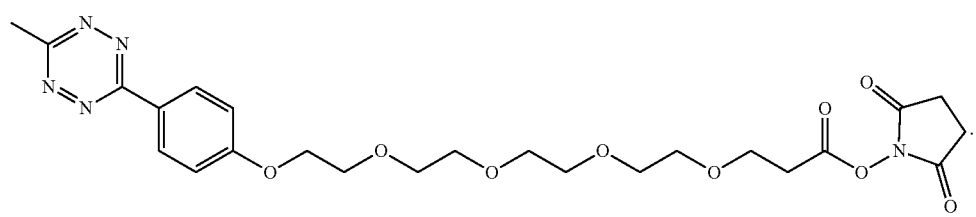

Various NPPs were formed with different reactive groups for click or ligation chemistry reactions to connect them covalently with charge tags. Some non-limiting examples included:
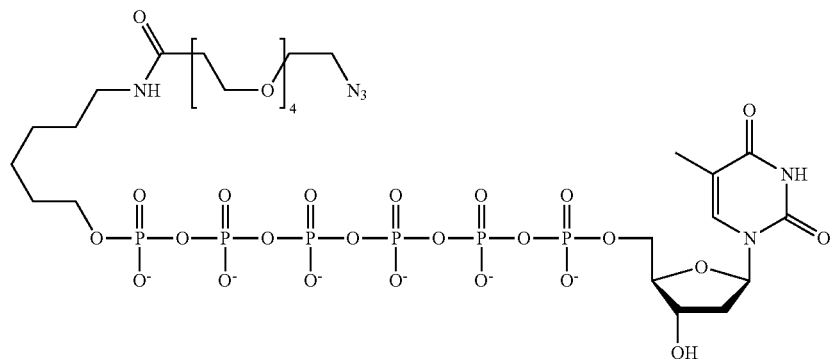
35
reacted with an alkyne-containing charge tag to create, for example, the following:
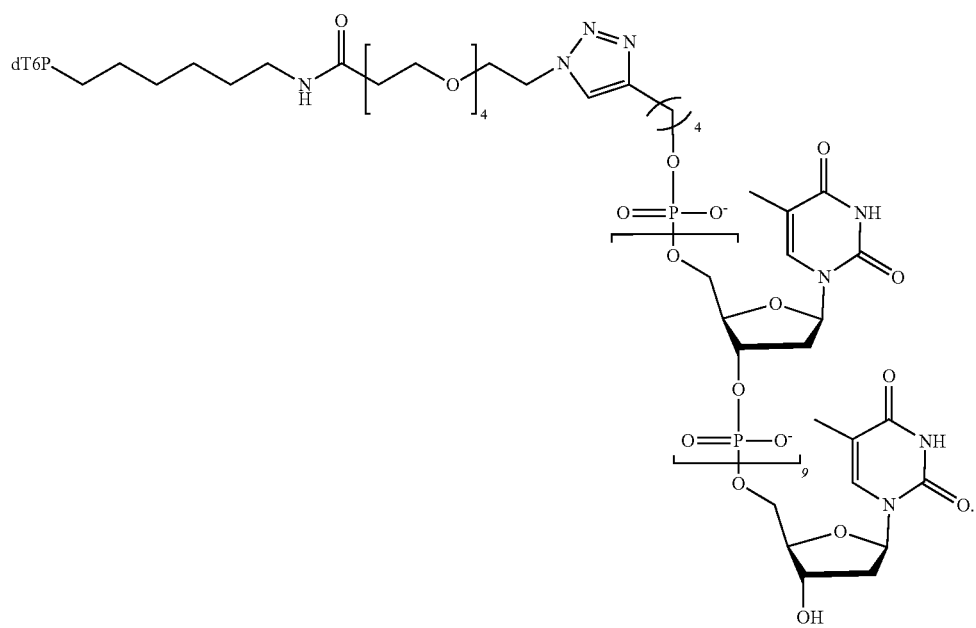

Alternatively, a methyltetrazine containing NPP such as
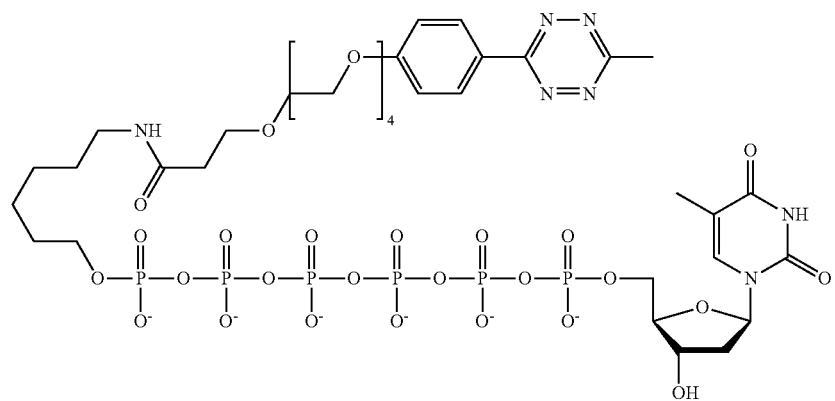
was reacted with a TCO-containing charge tag to form the following:
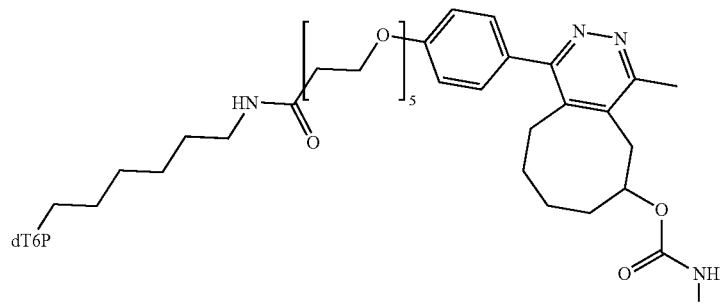
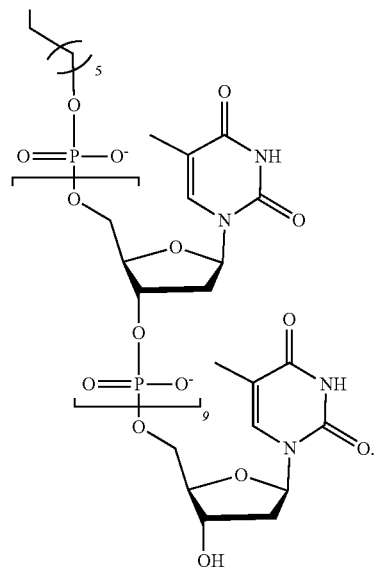

In other examples, DBCO-azide click chemistry between an NPP and a charge tag was used to form compounds such as the following:

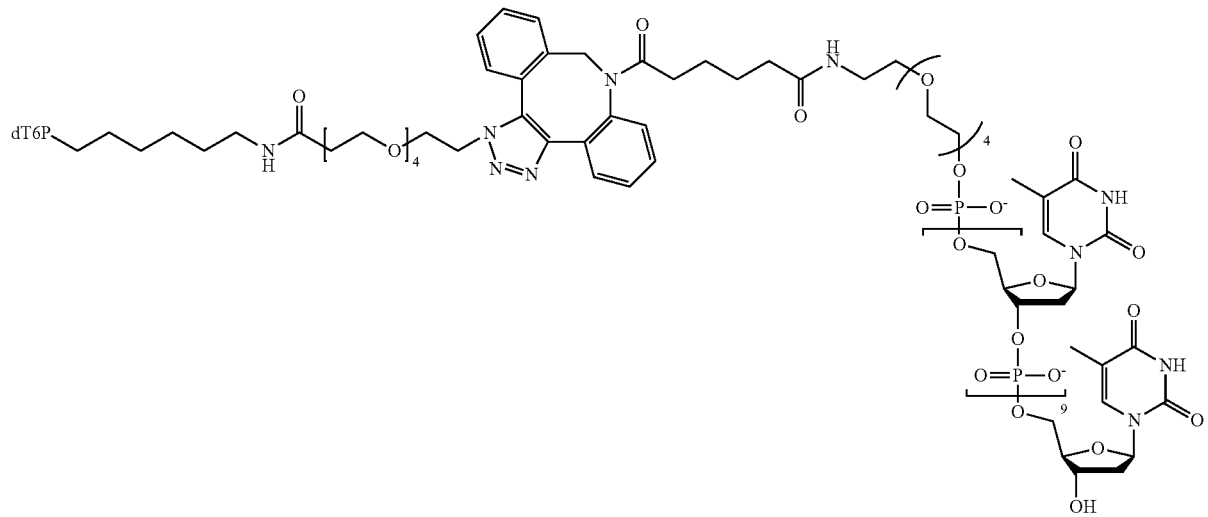

In other examples, a maleimide group on a nucleotide or charge tag may be reacted with a thiol group on a charge tag or nucleotide, respectively, to link the two via a maleimide-thiol reaction:

An NPP or charge tag containing a maleimide group

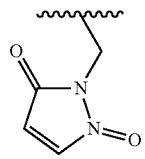

reacted with a charge tag or NPP containing a thiol-containing group, respectively, in the presence of a reducing agent such as (tris(2-carboxyethyl)phosphine) resulted in covalent bonding between the two, for example

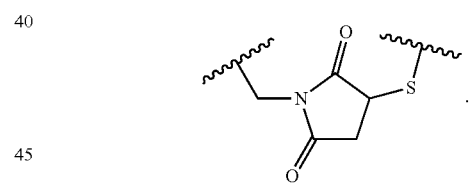

As shown in Table 2, various copper salts, ligands, additives, solvents, reaction durations, and reaction temperatures may be used for different copper-assisted click chemistries.

TABLE 2

Cu-assisted click chemistries

| Cu salt | Ligand | Additive | Solvent | Duration | T Deg. C. | Remarks |
|---|---|---|---|---|---|---|
| CuBr (10) | TBTA (20) | — | DMSO/t-BuOH | Overnight | 40 | No pdt, $N_3$-dT6P recovered |
| $CuSO_4$ (25) | THPTA (50) | Na Asc (50) | $H_2O$ | 2 h | RT | Incomplete rxn, pdt formed |
| $CuSO_4$ (500) | PMDETA (3500) | Na Asc (10000) | $H_2O$ | 1 h | RT | $N_3$-dT6P recovered |
| $CuSO_4$ (500) | THPTA (3500) | Na Asc (10000) | $H_2O$ | Overnight | RT | Pdt formed in low yield |

TABLE 2-continued

Cu-assisted click chemistries

| Cu salt | Ligand | Additive | Solvent | Duration | T Deg. C. | Remarks |
|---|---|---|---|---|---|---|
| CuSO$_4$ (25) | THPTA (50) | Na Asc (eq) | H$_2$O | Overnight | RT | Pdt formed, incomplete rxn |
| | | | | | 4 | Pdt formed, incomplete rxn, highest yield in series |
| | | | | | −20 | Pdt formed, incomplete rxn, lowest yield in series |
| CuSO$_4$ (10) | TBTA (20) | Na Asc (200) | DMSO/t-BuOH | Overnight | RT | No pdt, both SMs present |
| CuSO$_4$ (10) | THPTA (20) | Na Asc (200) | H$_2$O | Overnight | RT | Pdt formed, incomplete rxn |
| CuSO$_4$ (100) | THPTA (300) | Na Asc (1000) | H$_2$O | 24 h | RT | Pdt formed, complete rxn |

As can be seen, in general terms, in high Cu loading, a reaction may run to completion but with low yield. Comparatively, with low Cu loading, a reaction may not run to full completion but yield may be higher. With intermediate Cu loading, a reaction may run to completion and reaction product may be isolated in 86% yield by HPLC.

Figure 11:
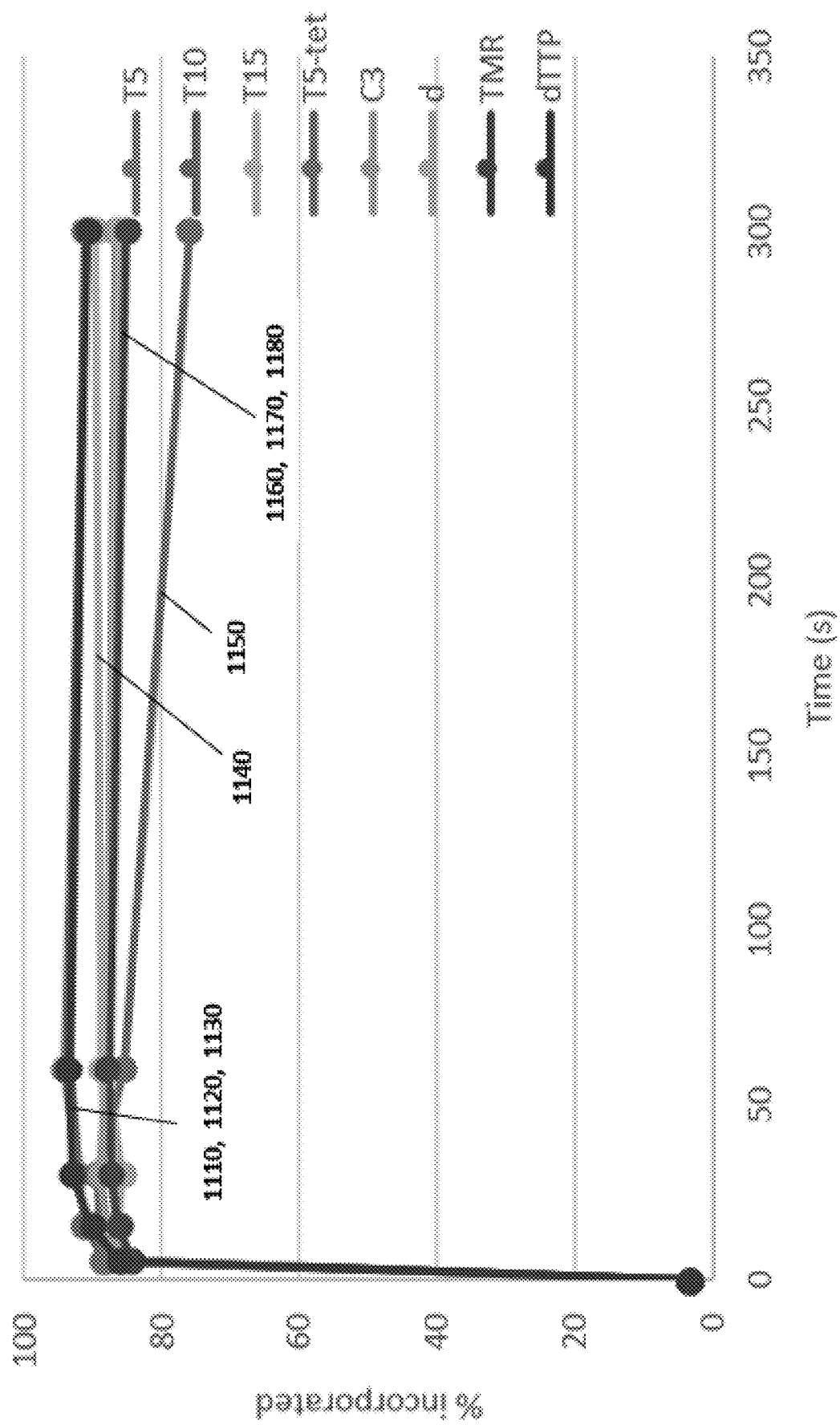
FIG. 11 shows, in one example, single nucleotide incorporation of phosphodiester based charge tags by polymerase phi29.

Incorporation of phosphodiester based charge tag modified nucleotides have been demonstrated. Incorporation may be carried out with different polymerases such as phi29 (and variants thereof) and Klenow fragment, or others used in sequencing-by-synthesis processes. Both polymerases can incorporate the charge tags successfully. Incorporation by phi29 for this example is shown in FIG. 11. In this example, single-stranded DNA template polynucleotide sequences were immobilized on a polymerized substrate and incubated with a buffer solution (50 mM Tris pH 7.5, 5 mM MnCl$_2$, 4 mM DTT) containing 100 nM 5'-Cy5-labelled DNA primers (22-mers) complimentary to a portion of such template sequences, 1 μM phi29, and 10 μM of a given nucleotide for single-nucleotide incorporation into the primers based on the template. Following incubation for various durations at 30 degrees Celsius, to allow 5' incorporation of a charge-tagged thymidine (complementary to adenosine residue on the template strand immediately 5' to the portion complementary to the primers), polymerase reaction was quenched, primers were dehybridized and separated on a gel for detection of single-nucleotide incorporation. Linkages between deoxyribo-thymidine 5'-hexaphosphate (dT6P) included T5, T10 and T15, having the indicated repeats of thymidine nucleotides as charge tags; T5, T10 and T15 are attached via click chemistry, while T5-Tet is attached via tetrazine-TCO ligation. C3 Spacer (C3) and dSpacer (d) oligos were also used as charged tags, attached via TCO-tetrazine ligation. TMR is a tetramethylrhodamine-labelled dT6P with the following formula:

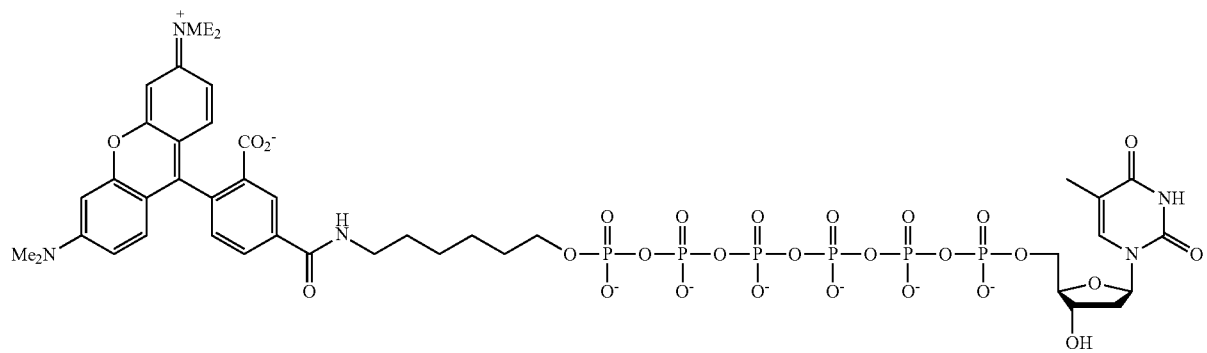

V2 and dTTP is deoxy-thymidine triphosphate without a charge or label to serve as a control.

Referring to FIGS. 11, 1110, 1120, and 1130 each individually represents % incorporation of dTTP, T10, or T5, respectively (whose plots overlap with each other and are therefore nearly indistinguishable from each other in FIG. 11), 1140 represents incorporation by T15, 1150 represents incorporation by T5-Tet, and 1160, 1170, and 1180 each individually represents % incorporation of TMR, d, and C3, respectively (whose plots overlap with each other and are therefore nearly indistinguishable from each other in FIG. 11).

A non-limiting example of a synthesis scheme used to synthesize a nucleotide analog with a peptide charge tag in accordance with the present disclosure is shown below

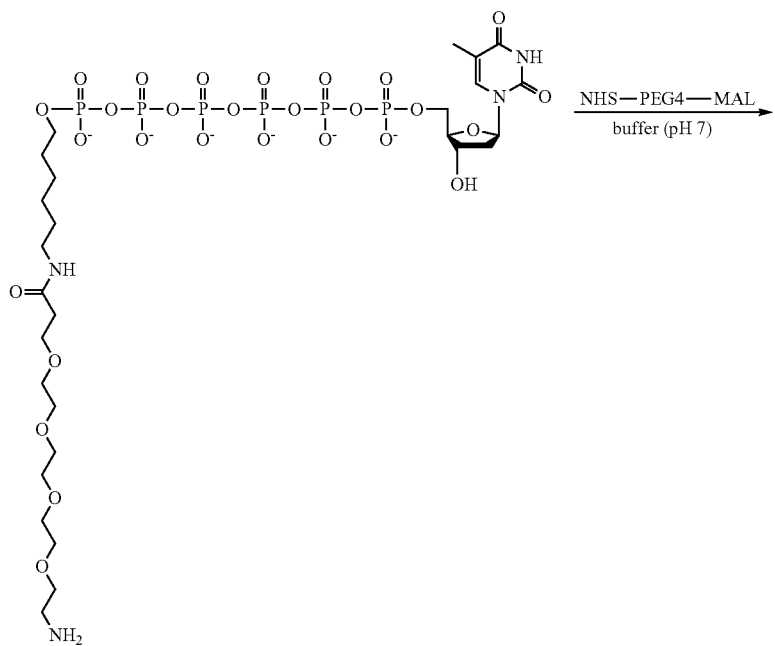
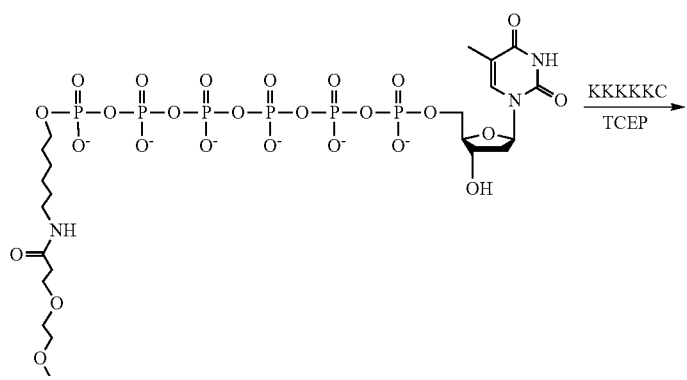
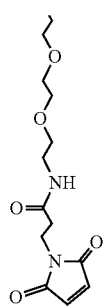

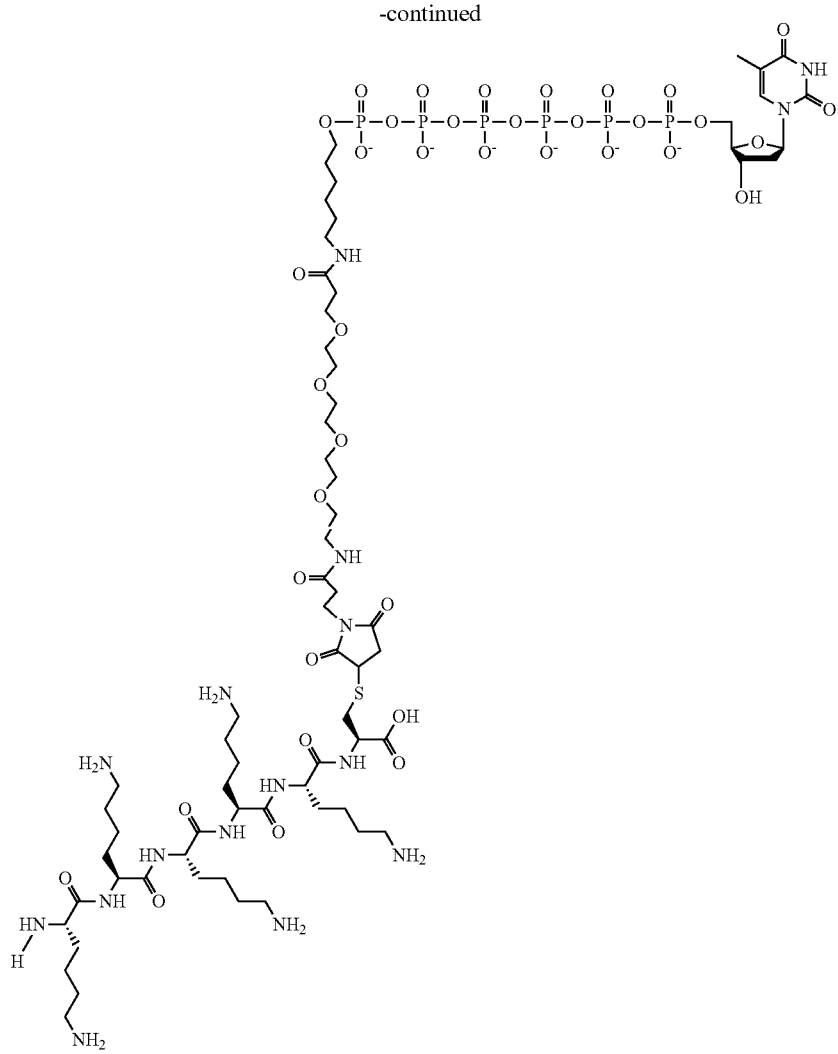

In another example, rather than positively charged lysine residues as illustrated above, a comparable scheme was used for synthesizing a charge tag with negatively charged amino acids such as:

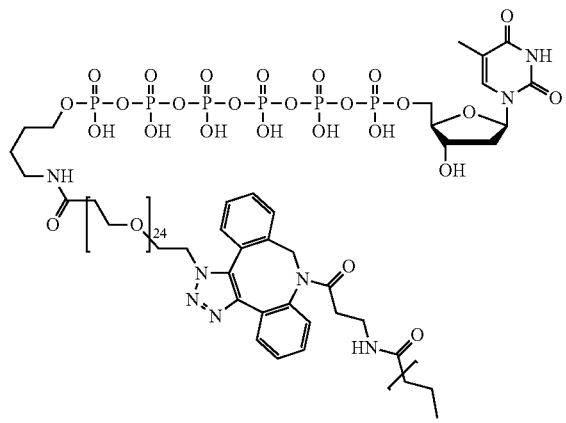

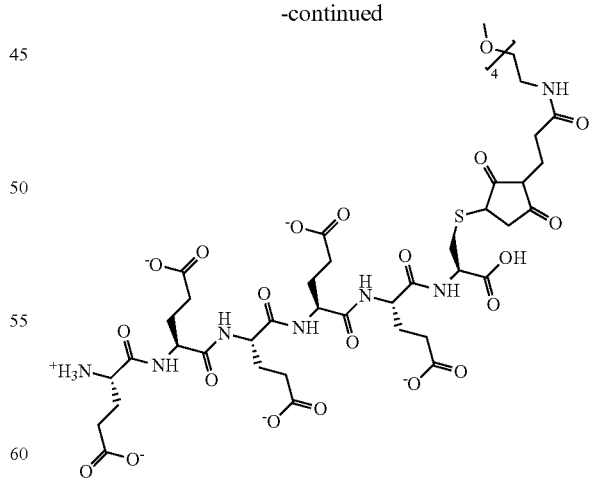

As would be evident to skilled persons, many variations on this scheme would be possible within keeping with the teachings of the present disclosure. For example, amino acids other than lysine, including any of the charged or uncharged amino acids described above may be employed, and they may number more or less than the peptide charge tag length shown in this example. Peptide charge tags with charges of different valences and magnitudes may therefore be employed.

Furthermore, different reactive groups may be added to the 5' end of a nucleotide analog, and with different types and lengths of linker portions, such as, for additional non-limiting examples:

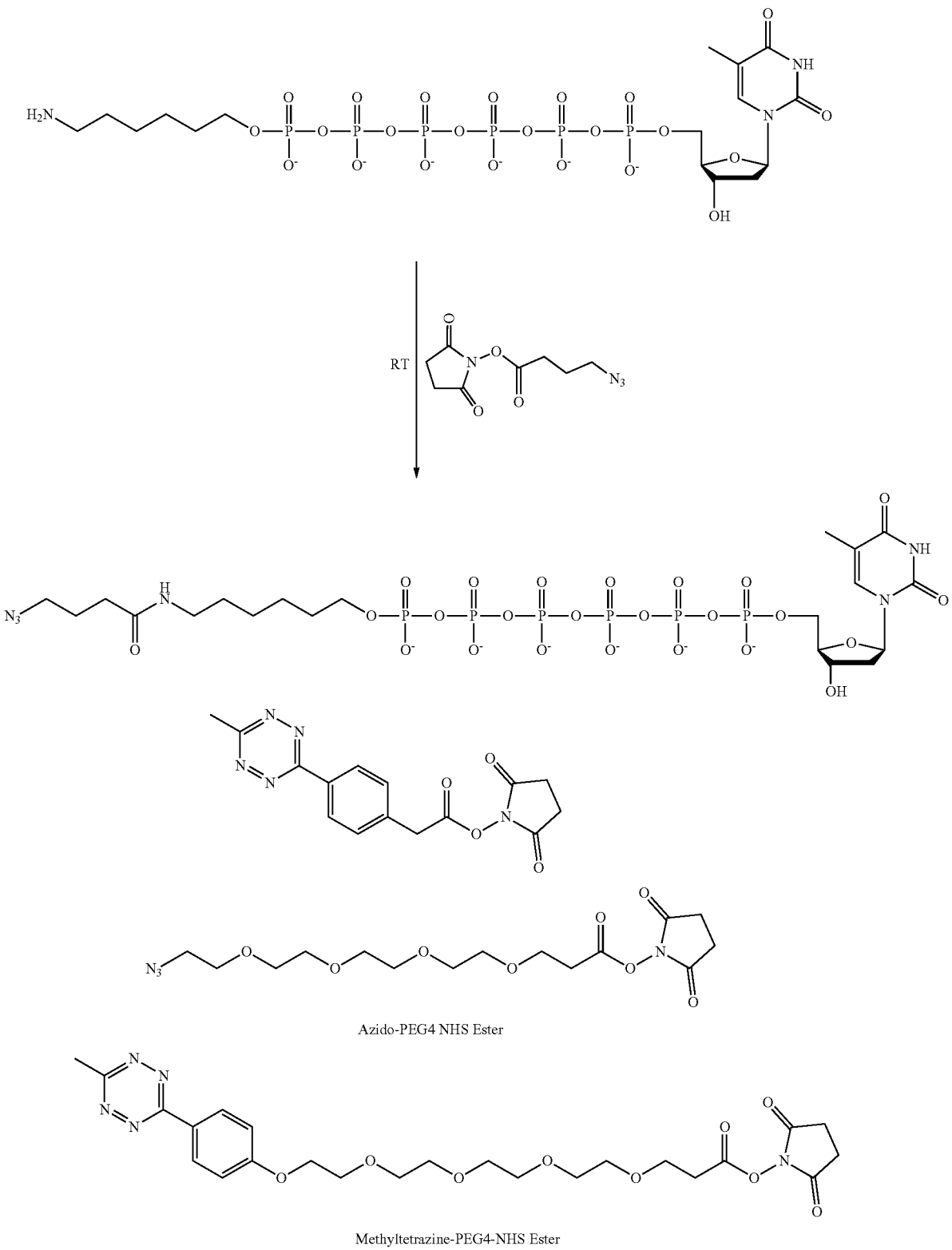

Azido-PEG4 NHS Ester

Methyltetrazine-PEG4-NHS Ester

These additions may yielded nucleotide analogs with various reactive groups including azide or methyltetrazine reactive groups, appended by linkers of various types and lengths, including, as non-limiting examples:

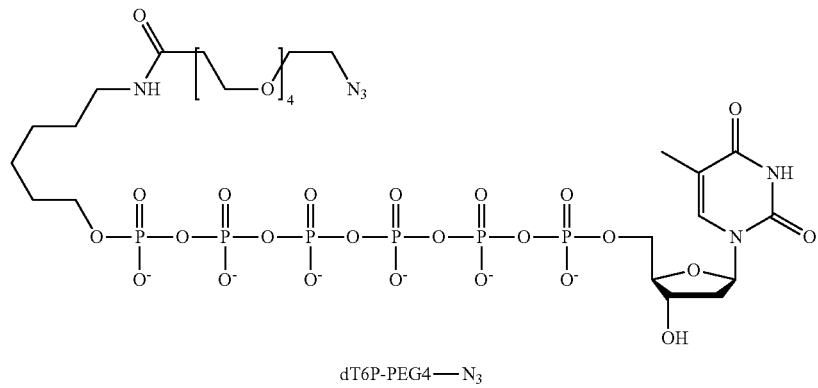

dT6P-PEG4—N₃

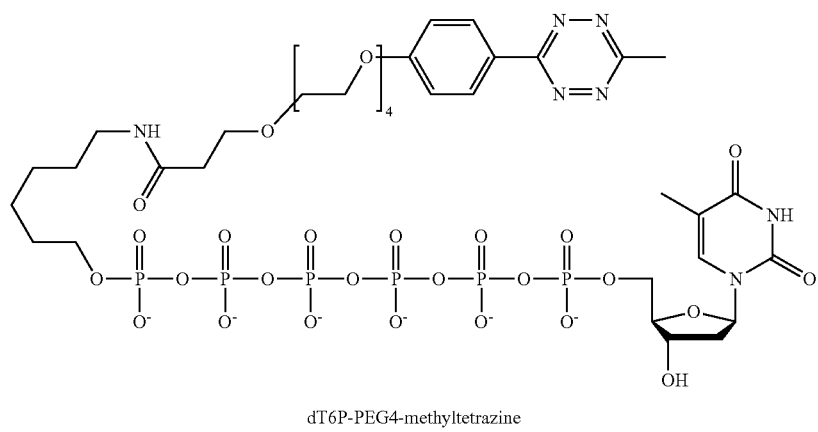

dT6P-PEG4-methyltetrazine

In still other examples, an alkyne, TCO, or DBCO group was similarly added, or a thiol group. A corresponding reactive group could then be added to a peptide charge tag such that the two could be joined by the above-disclosed click or ligation chemistries, or others known to skilled artisans. Peptide based charge tags can be synthesized using fluorenylmethyloxycarbonyl (Fmoc) and tert-butyloxycarbonyl (Boc) protecting group chemistry for solid phase peptide synthesis. An orthogonal "handle" reactive group can be introduced in the peptide synthesis at the terminal end to allow conjugation to a nucleotide or nucleic acid. Orthogonal chemistry methods include azide-alkyne copper-assisted click reaction, copper free click chemistry with DBCO and azide, and TCO-tetrazine ligation. Reactive side chains of amino acids such as thiol of cysteine can also be used in thiol-maleimide chemistry.

The availability of amino acids containing side chains with different pKas also allow peptide charge tags that would be charged at different pHs. For instance, histidine has a pKa of 6.04, while Lysine has a side chain with a pKa of 10.54. Thus, at neutral pH, only lysine could be charged. This also allows further modulation of the number of charges and charge density by modifying the pH of the buffer environment.

In addition, peptide charge tags can be easily appended to peptide nucleic acid (PNA) oligomers, since both peptides and PNAs are synthesized with the same solid phase peptide chemistry. This would be used to further modify the properties of the peptide charge tag, or add association properties of the charge tag to linkers such as nucleic acid based linkers.

Examples of compounds used in the synthesis of a dendron charge tag, and corresponding charges per terminal constitutional repeating unit, include the following:

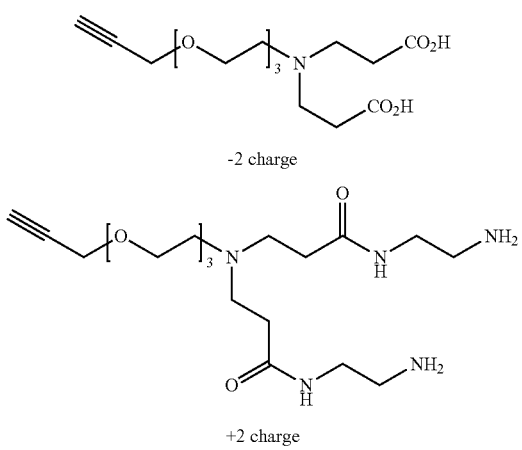

-continued

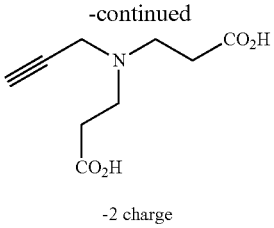
-2 charge

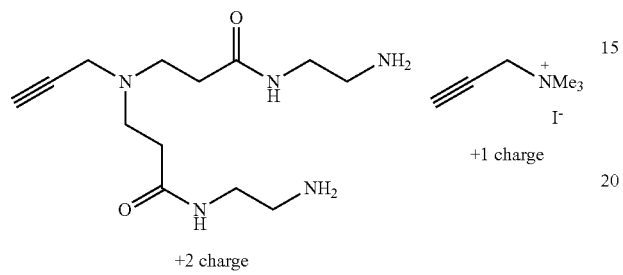
+2 charge     +1 charge

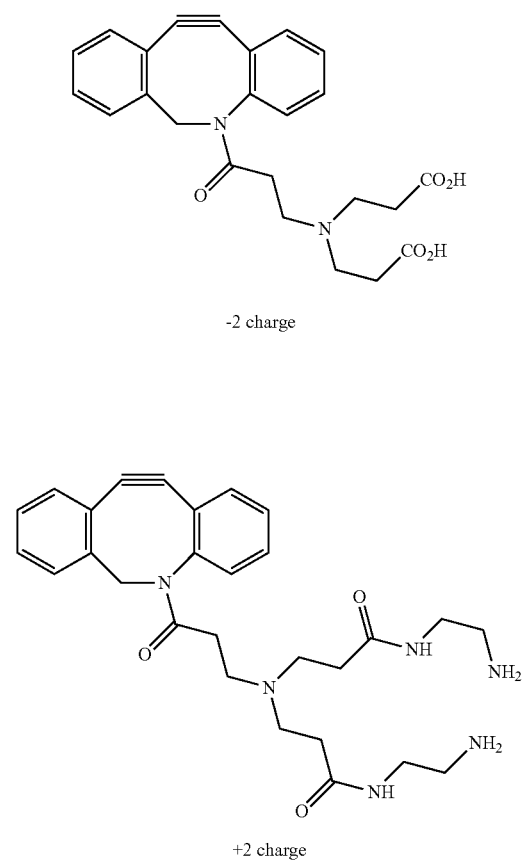
-2 charge

+2 charge

In these examples, different reactive groups are shown at the free valence end of the dendron, as well as different potential stem lengths between a branch point and a free terminal end of an individual constitutional repeating unit, but these are merely non-limiting examples.

The following scheme provides illustrative examples of possible dendron charge tag structure:

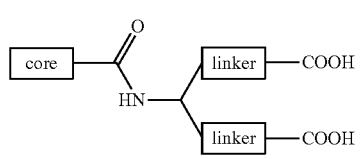
(A)

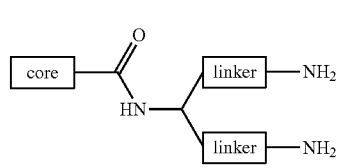
(B)

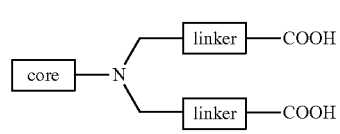
(C)

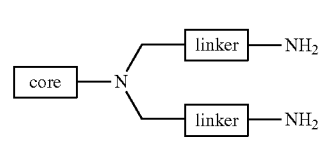
(D)

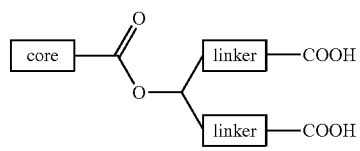
(E)

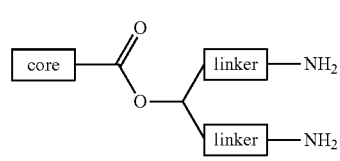
(F)

Shown are, for example, dendron with amide linkages and (A) terminal carboxylic acid or (B) amino groups; dendron with polypropylene imine) (PPI) linkages and (C) terminal carboxylic acid or (D) amino groups; and dendrons with ester linkages and (E) terminal carboxylic acid or (F) amino groups.

Generally, dendron charge tags may be synthesized according to divergent or convergent synthesis methods, according to the following representative schemes:

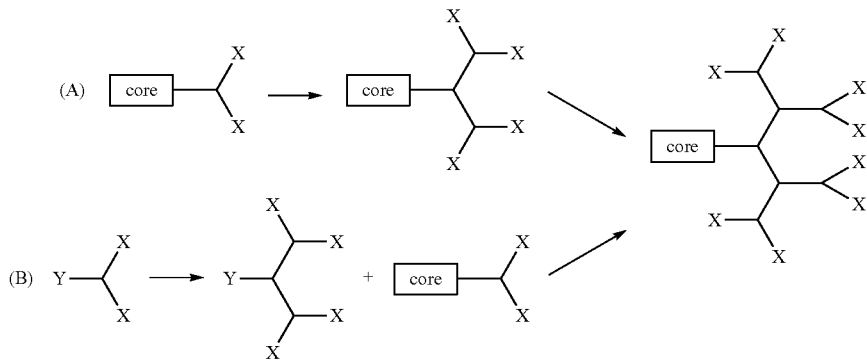

In divergent synthesis (A), a dendron is assembled by a series of outwards extending reactions from the core, usually by repetitive Michael addition. In convergent synthesis (B), a dendron is constructed by a series of inwards building reactions from the peripheral and eventually attached to the core.

Some examples of such divergent synthesis schemes in accordance with the present disclosure were as follows:

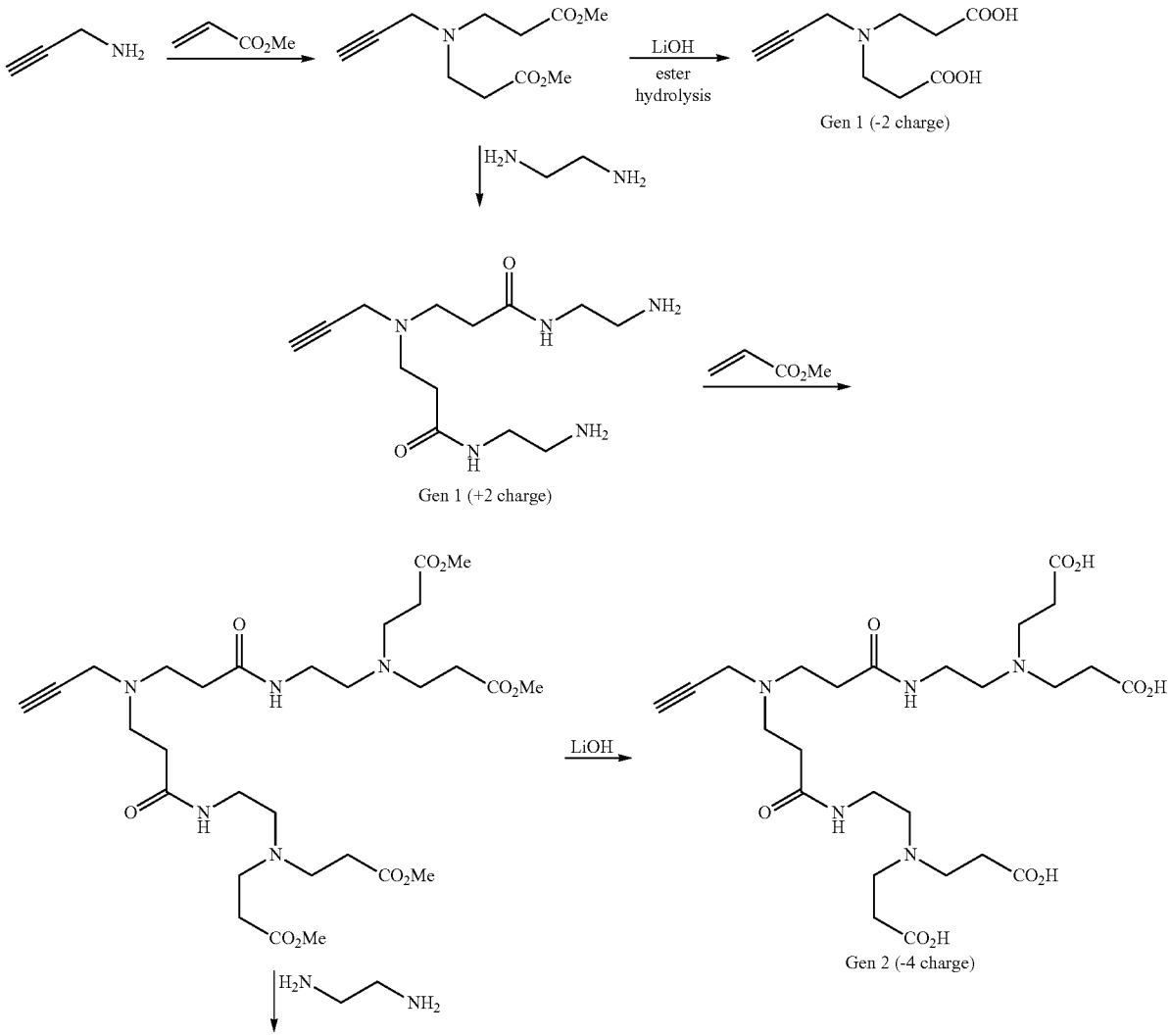

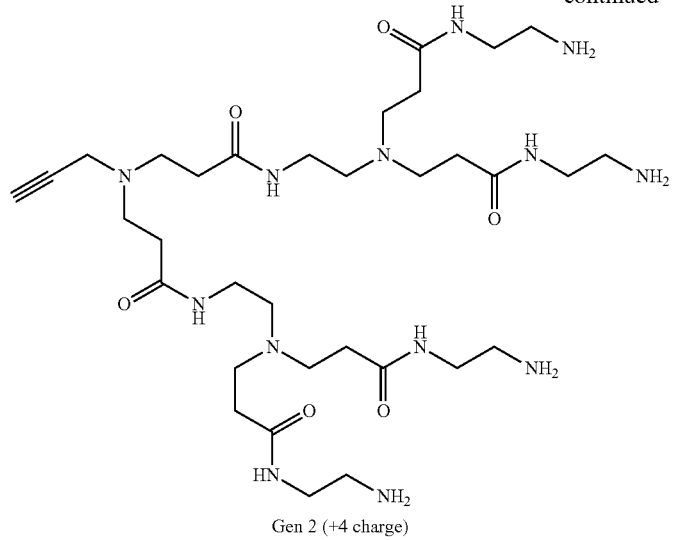

Gen 2 (+4 charge)

Figure 18A:
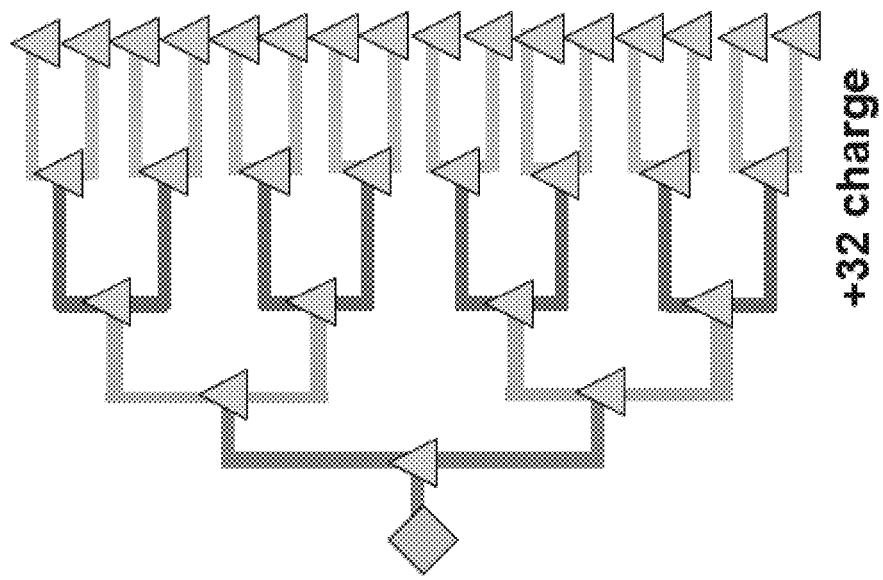
FIGS. 18A and 18B show examples of branched peptide-based charge tags.
Figure 18A:
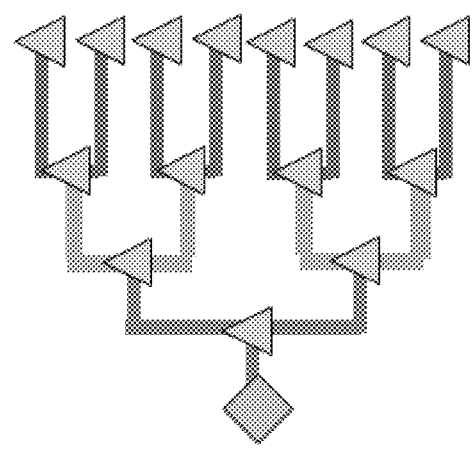
Figure 18A:
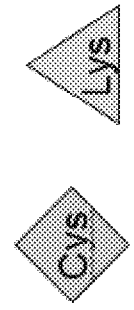
Figure 18B:
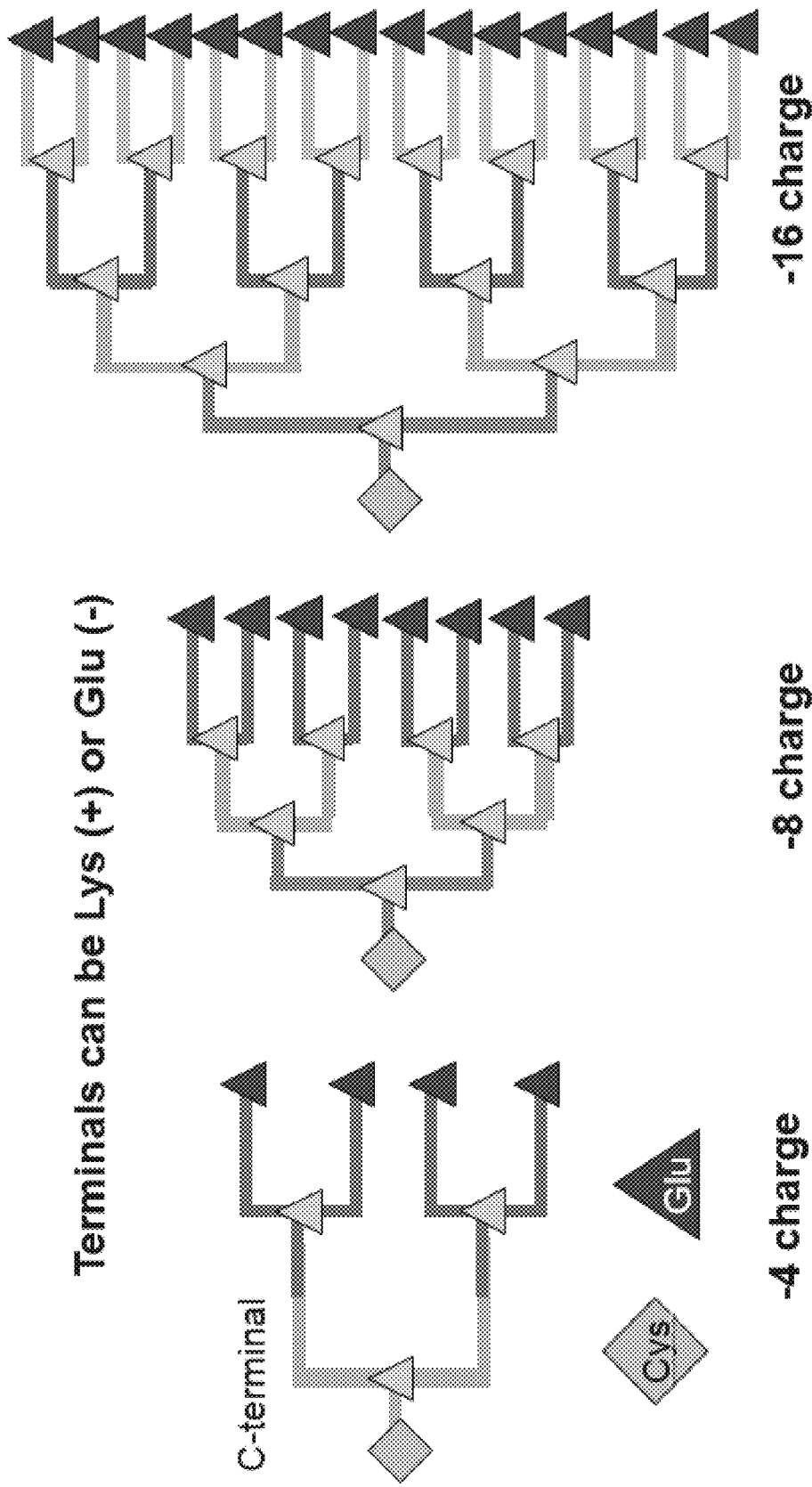

In these examples, a methacrylate group was added by Michael addition to an alkyne stem, followed by either deprotection of acetyl groups to form the carboxylic acid groups, or addition of ethylenediamine to form the amino groups. Repetitive cycles of Michael addition resulted in successive generation of dendrons with twice the number of terminal functional groups compared to the previous generation. Additional generations may be added, and a different reactive group could be used at the stem/free valence end. In some examples, an additional generation or more may be iteratively added according to the foregoing synthesis schemes to increase charge carried by a tag. Valence of a charge may be varied by incorporating a positively or negatively charged amino acid at an end group. Examples are shown in FIGS. 18A and 18B. In both non-limiting example, a charge tag terminating in a cysteine residue is shown, which could be linked to a linker section for charging a nucleotide as disclosed herein, though other chemistries such as disclosed herein are also intended as examples. In FIG. 18A, positively charged lysine residues for the end groups following either 2, 3, or 4 branchings, yielding different terminal charge magnitudes. Alternatively, as shown in FIG. 18B, a negatively charged amino acid such as glutamate could form end groups after various generations of branching, again yielding different magnitudes of terminal charge.

In another example, one or more lysine residues in a charge tag may be methylated (e.g., trimethylated). Unlike unmethylated lysine, the charge of trimethylated lysine is not pH-dependent.

Another example, with a DBCO at the free valence end, is as follows:

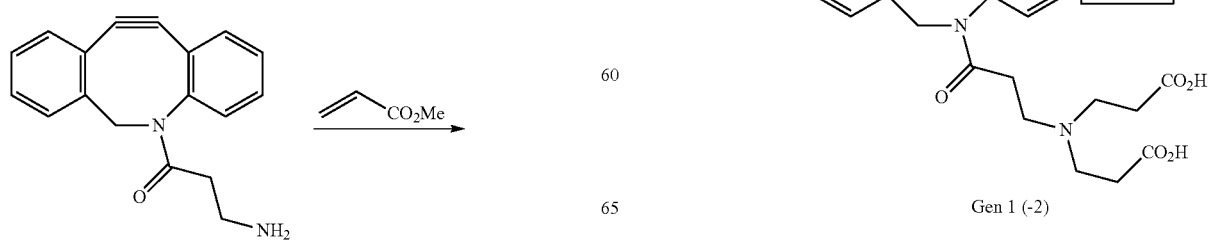

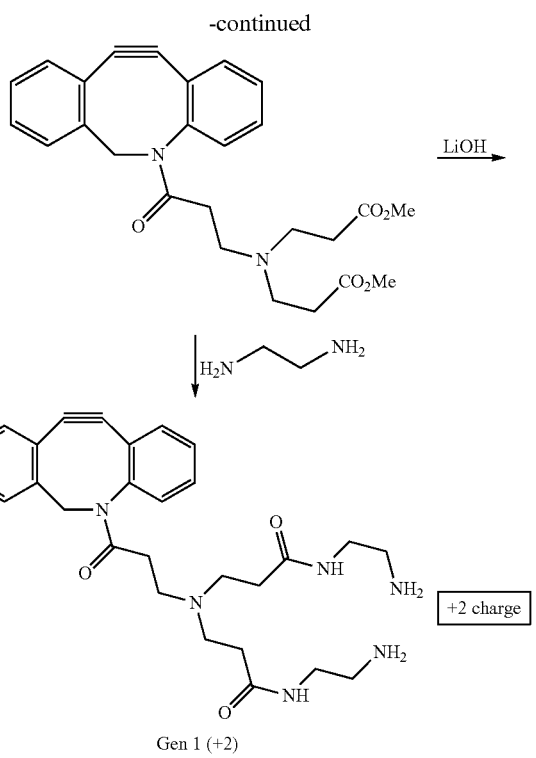

Some examples of amide-based and PPI dendron designs for dendron charge tags and their synthesis include the following:

A-1
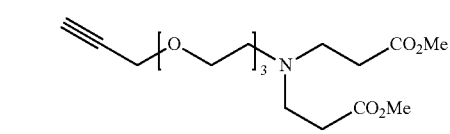

A-2
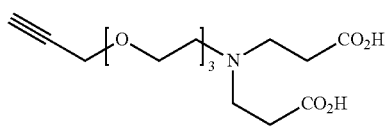

A-3
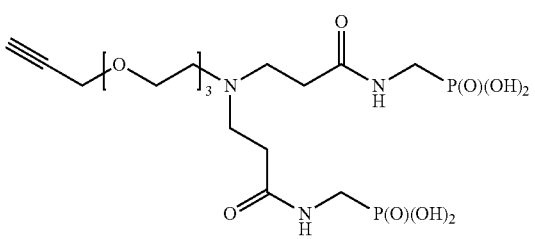

A-4
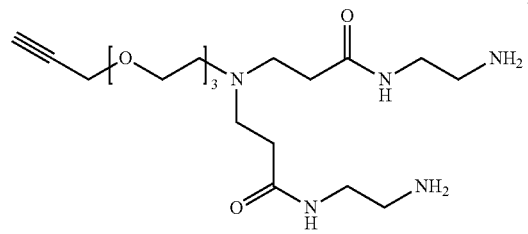

B-1
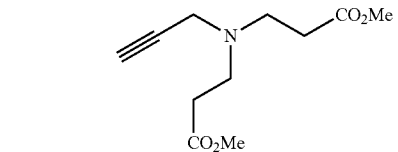

B-2
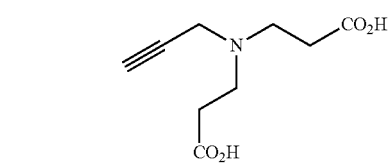

B-3
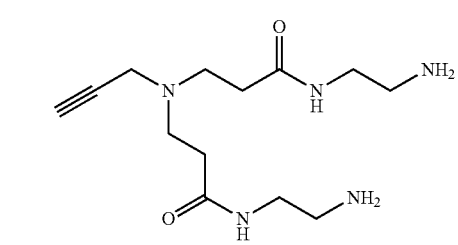

B-4
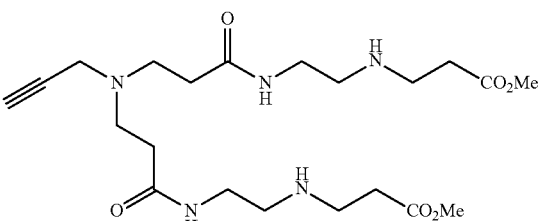

C-1
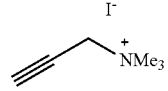

C-2
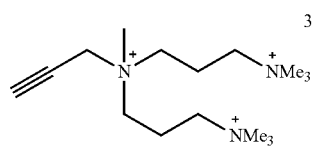

Some advantages of quaternary ammonium groups included in examples C-1 and C-2 are that they may not be affected by pH, may not coordinate metals, and may be less likely to attach to poly(vinyl phosphonic acid) (PVPA) during synthesis and handling.

In another example, a constitutional repeating until with three degrees of branching may be used. It yet a further example, convergent synthesis may be used rather than divergent synthesis. A benefit of using a unit with three degrees of branching is that more charges may be added per generation, compared to a dendron with units having only two degrees of branching, resulting in fewer generations required to attain a given preferred charge. An example was as follows:

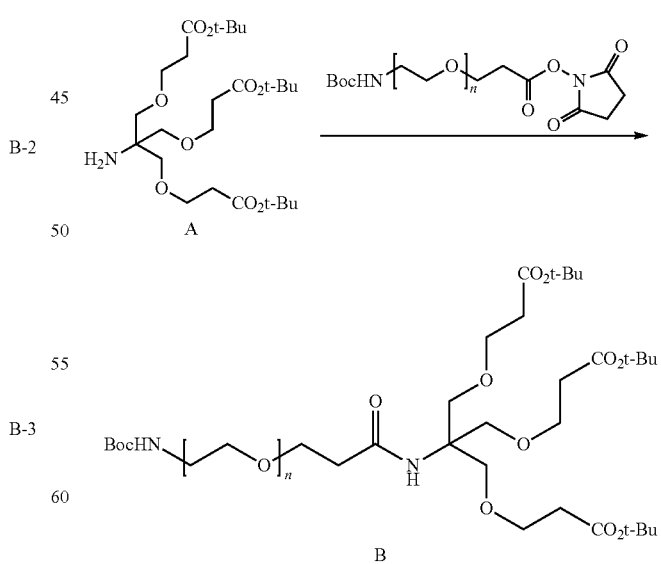

In this example, a constitutional repeating unit is functionalized with a tert-butyloxycarbonyl (Boc) group. Subsequently,

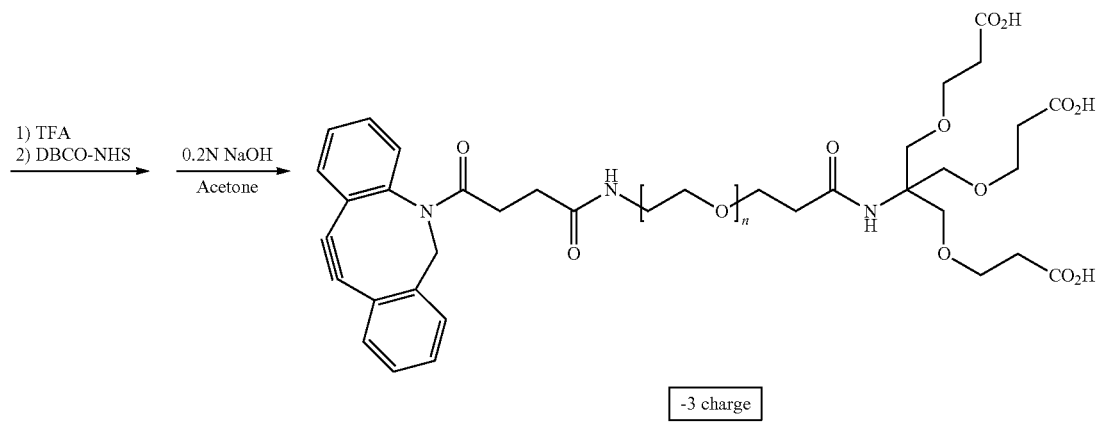
a DBCO group may be added and, upon deprotection of acetyl groups to form the carboxylic acid groups. The resulting compound has, in this case, a −3 charge. In a subsequent reaction, compound the compound A above was added in a second generation dendron, to give a charge of 9, as follows:
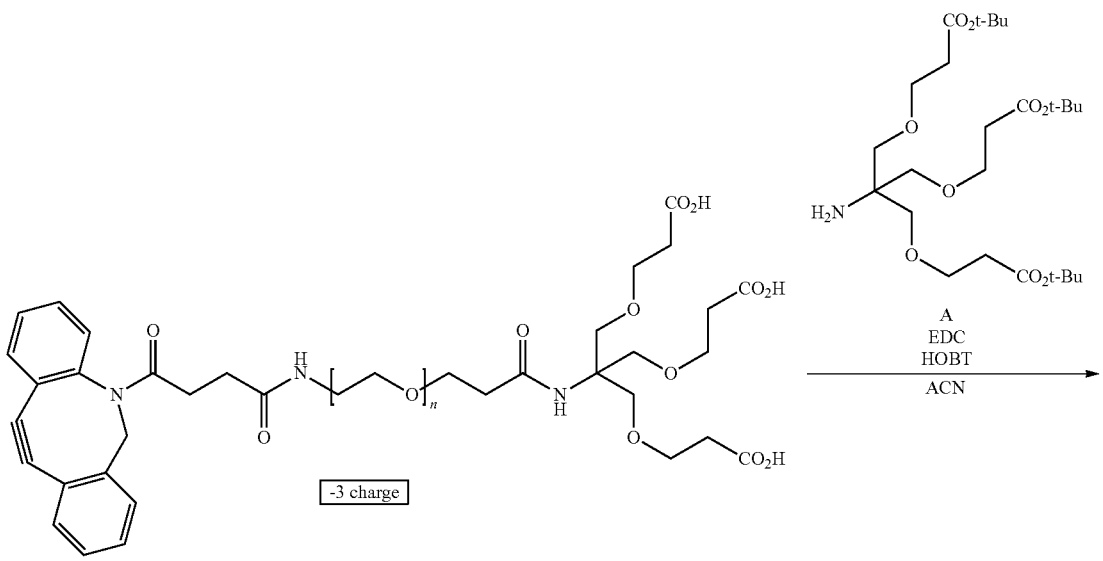

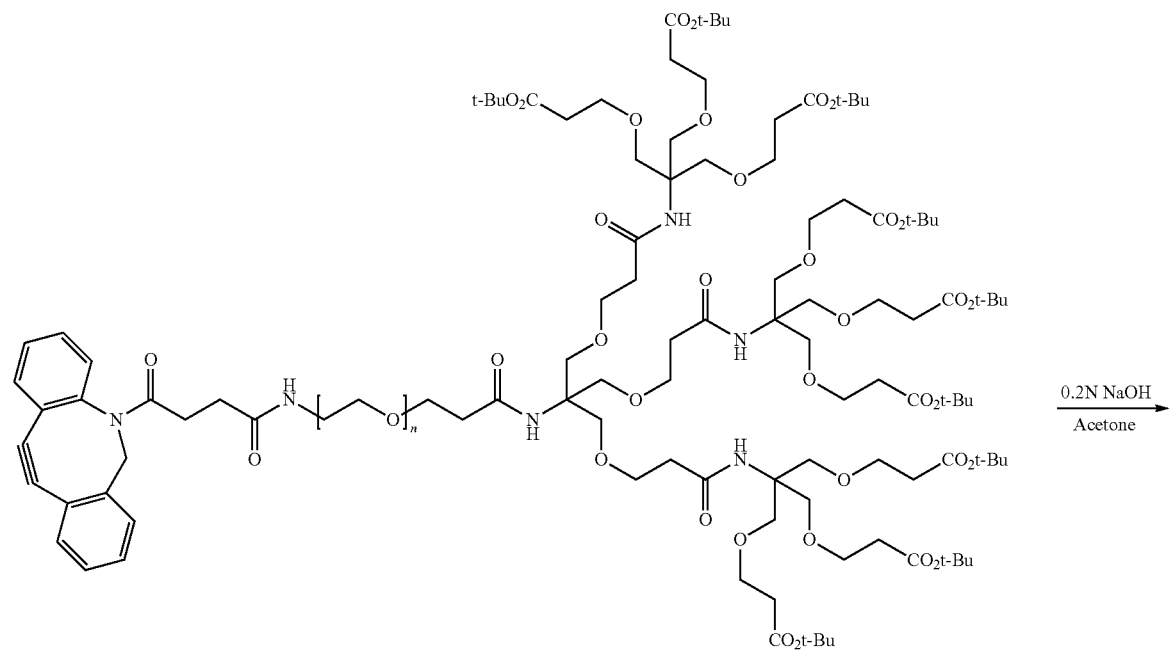
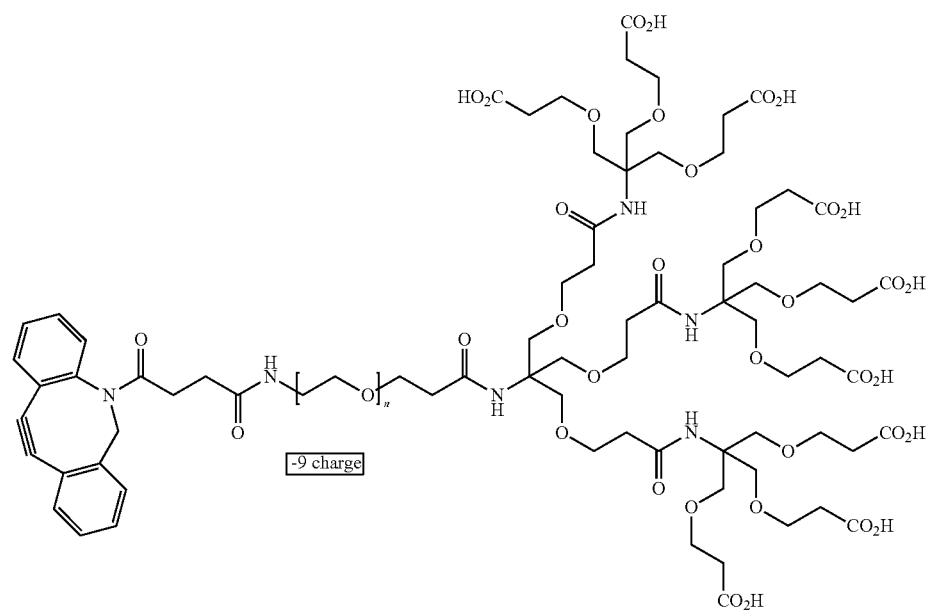

By iteratively combining the foregoing steps, three second degree dendrons can be combined, to create a third generation dendron with a charge of −27, via convergent synthesis, according to the following example:
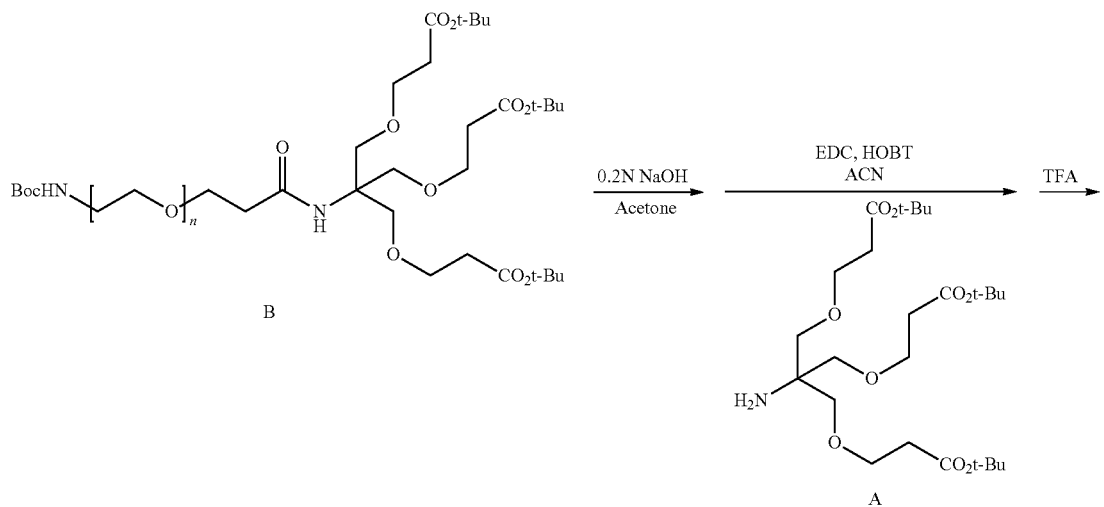
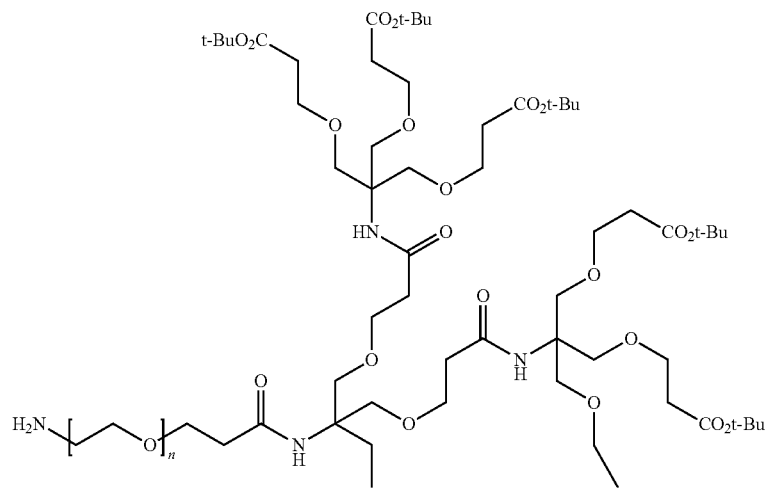
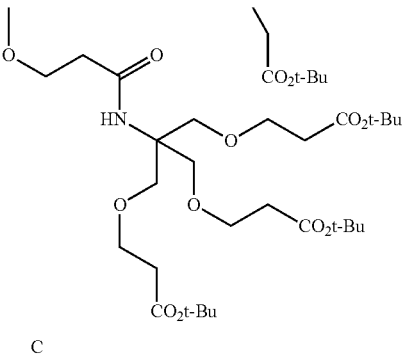

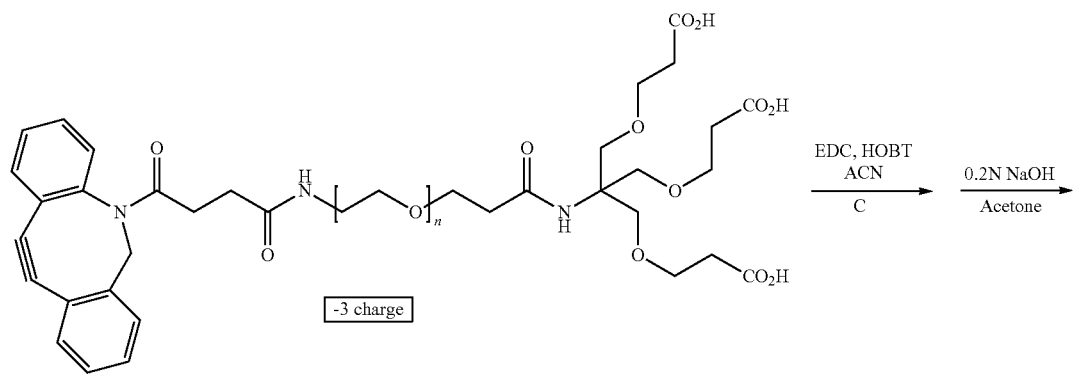
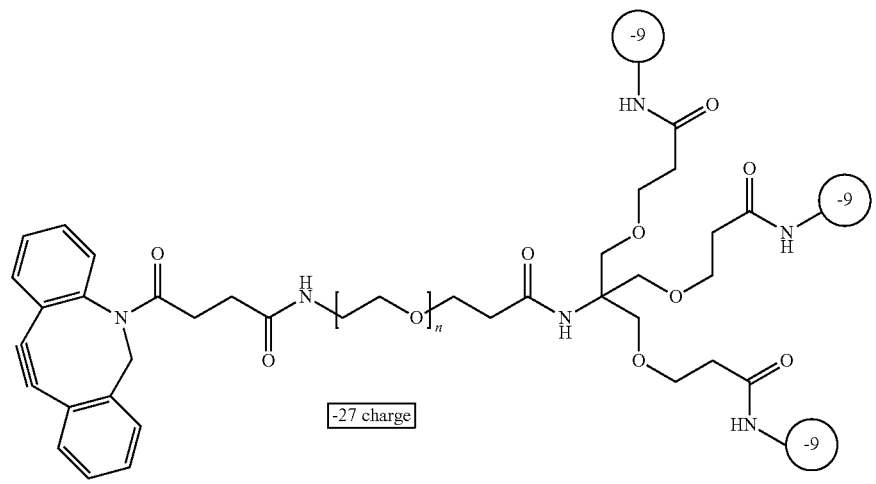
A dendron bearing negatively charged carboxylic acid groups was converted to a dendron bearing positively charged amine groups as follows:
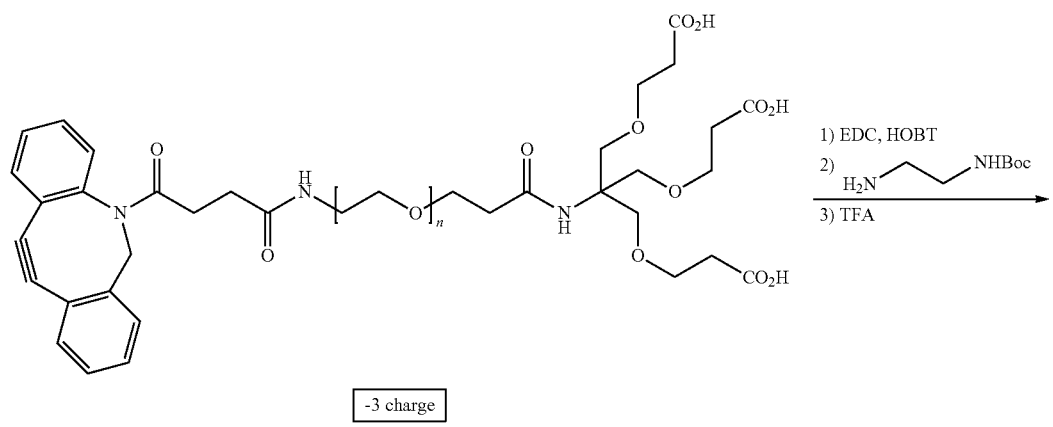

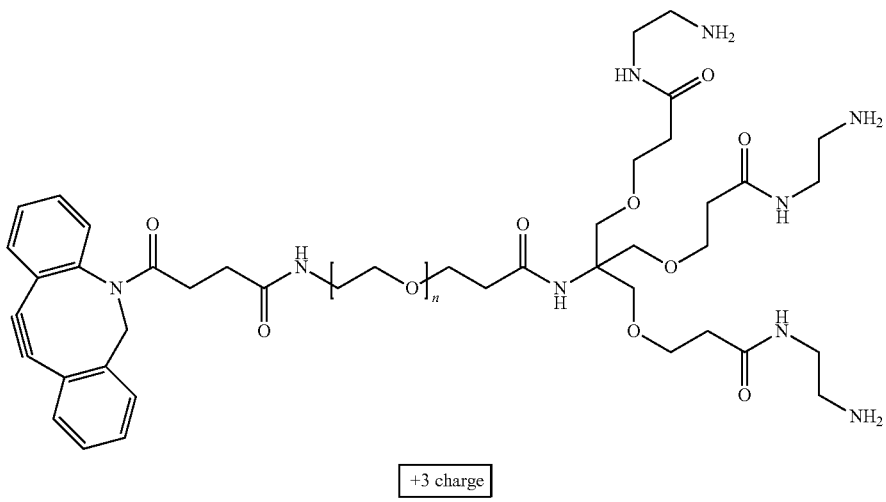
+3 charge
In another example, carboxylic acid groups was converted to amine groups according to the following scheme:
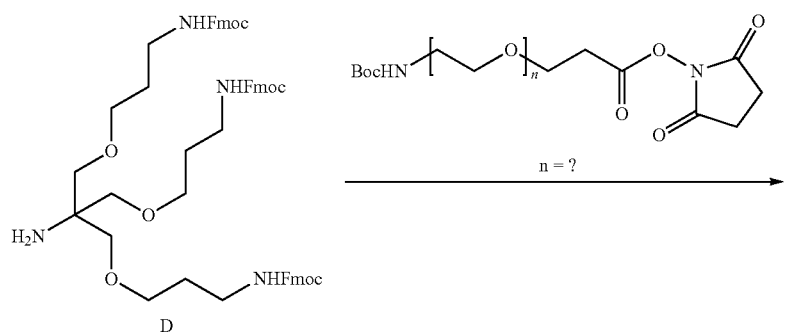
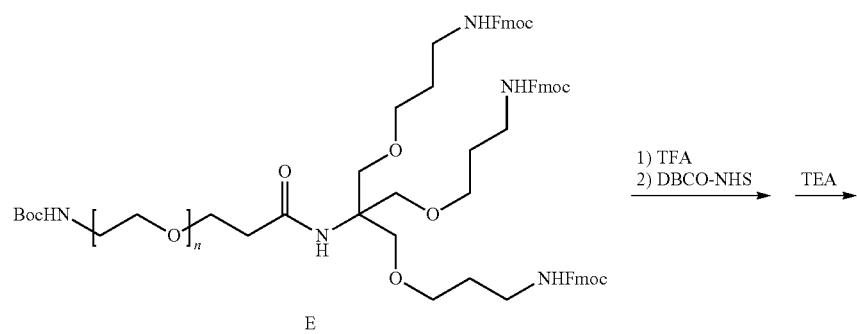

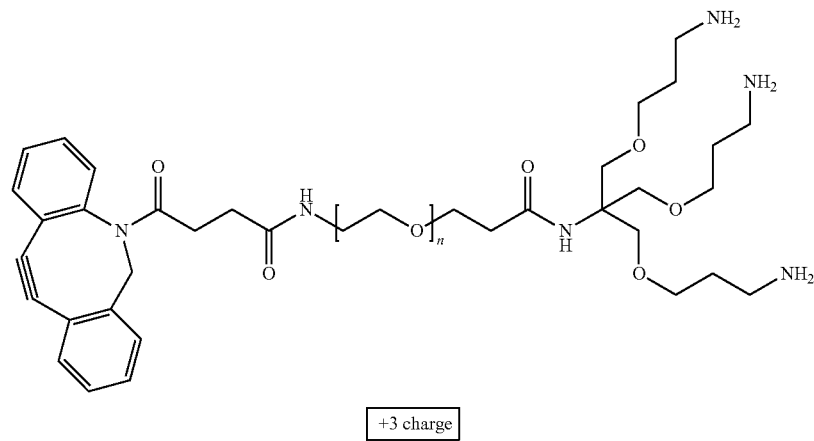
+3 charge
For a second generation, with a +9 charge, the following scheme may be used:
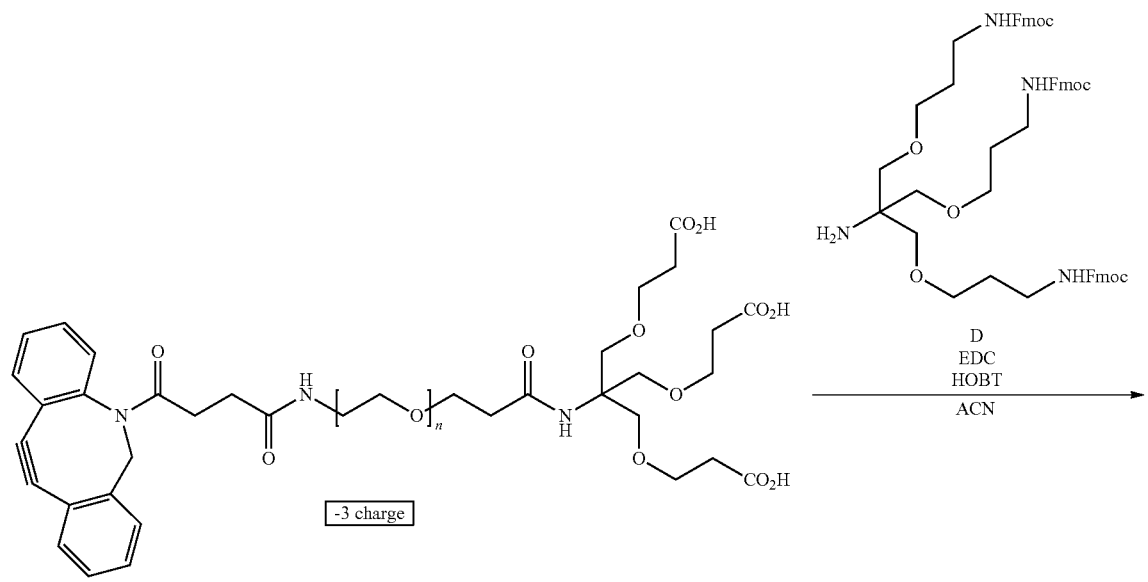

-continued
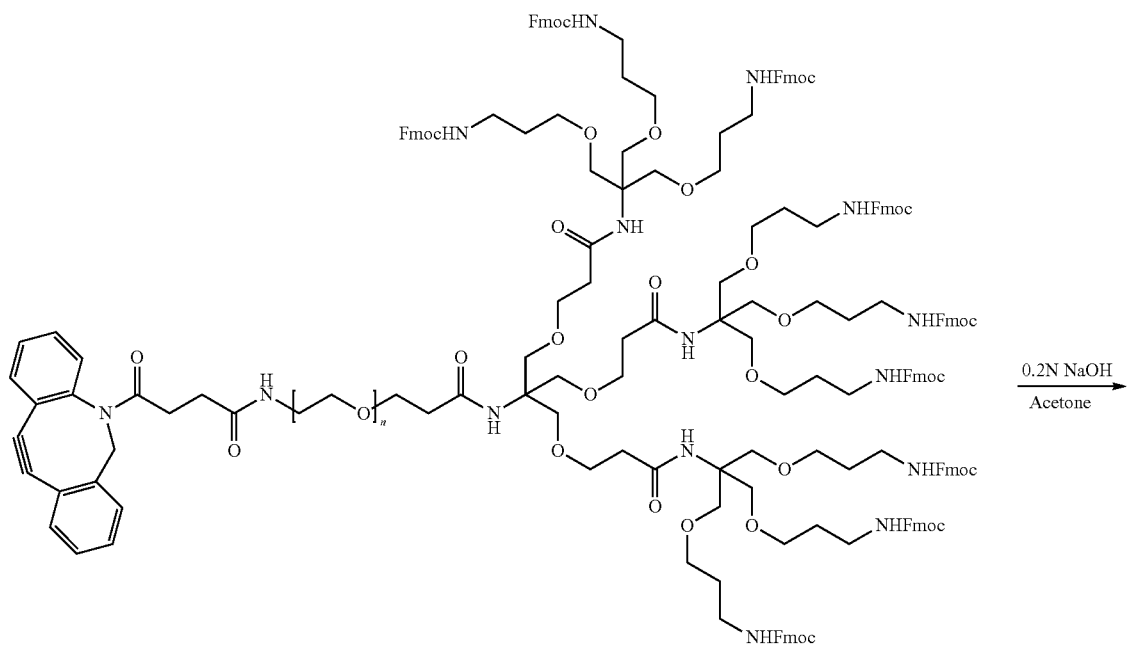
0.2N NaOH / Acetone →
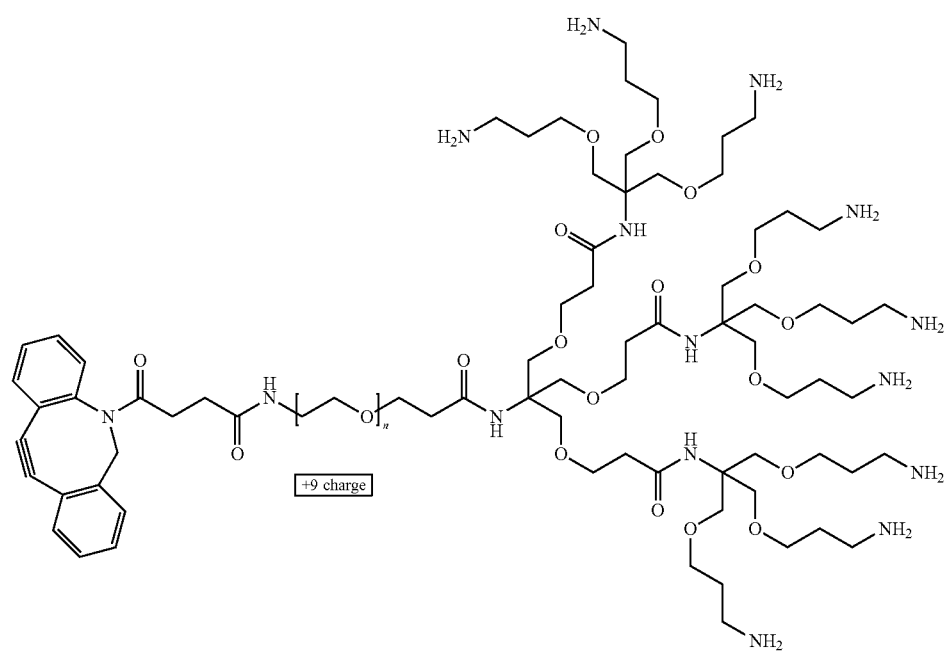
+9 charge

And, a third generation dendron may be synthesized, by a convergent synthesis scheme, to generate a dendron with +27 charge, as follows:
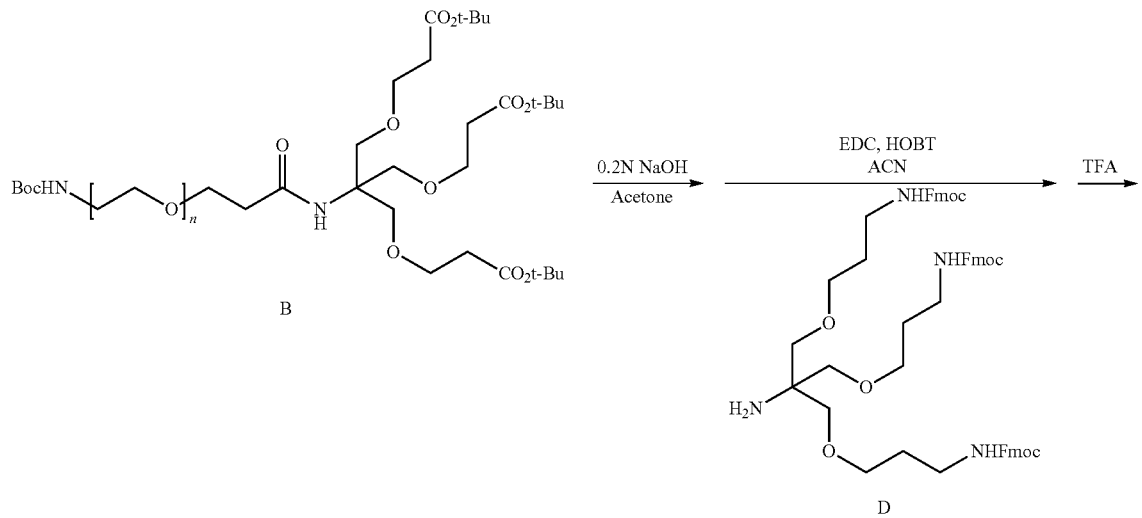
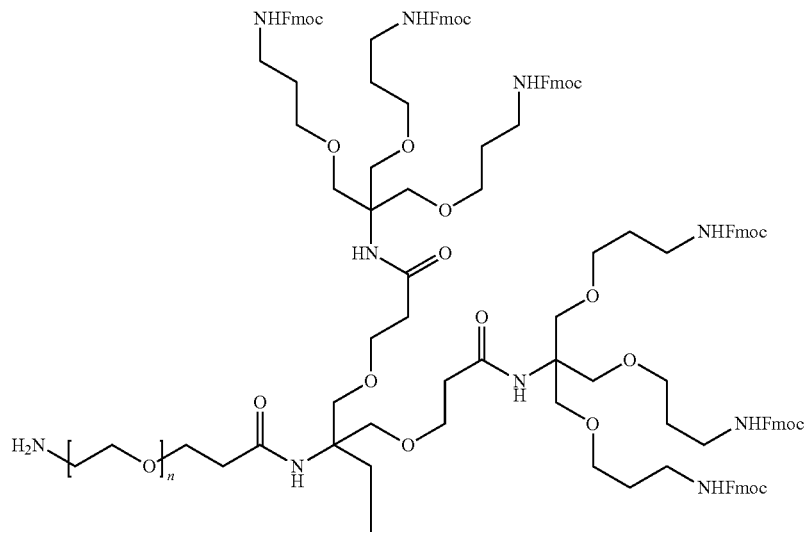
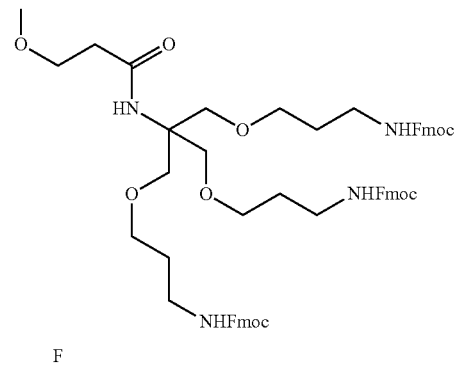

-continued

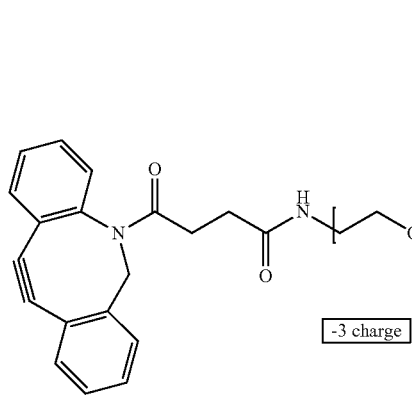 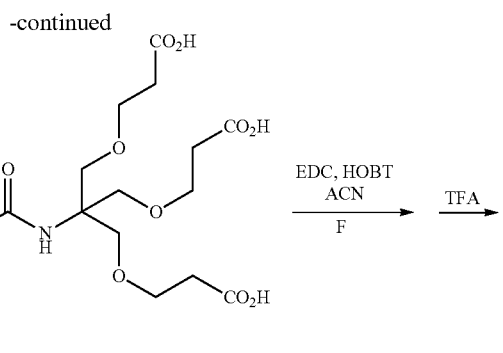

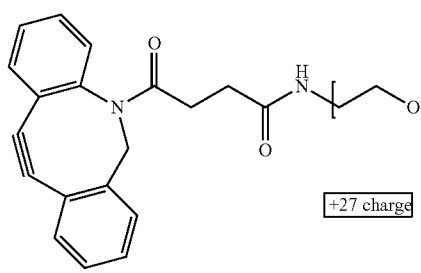 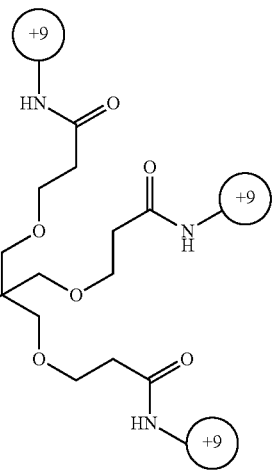

Depending on the reactive groups at the free valence end of a dendron synthesized in accordance with the present disclosure, which may include without limitation any of the examples described above, a corresponding paired reactive group may be appended to a nucleotide analog to allow ligation of the charge tag dendron to the nucleotide analog. According to the foregoing, a wide range of charges may be included in a nucleotide analog, including −32, −27, −16, −9, −8, −4, −3, −2, +2, +3, +4, +8, +9, +16, +27, and +32. Charged functional groups other than those illustrated in the foregoing non-limiting, example synthesis schemes may also be used.

Figure 17A:
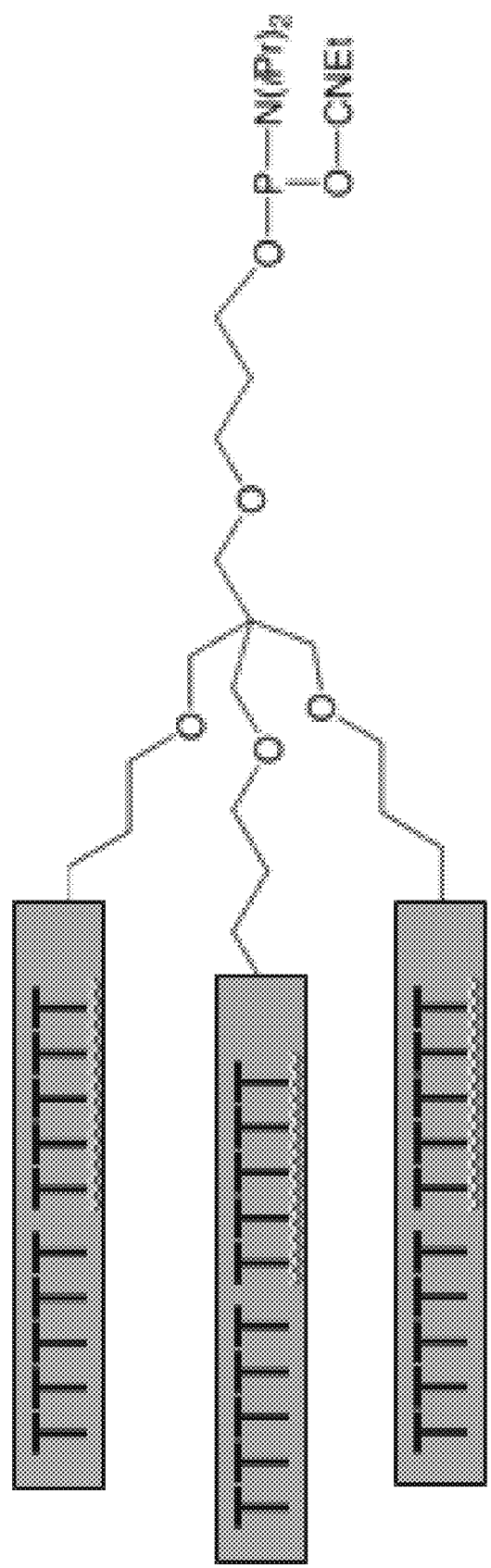
FIGS. 17A and 17B show examples of phosphodiester-based charge tags having a branched, dendron-like structure.
Figure 17B:
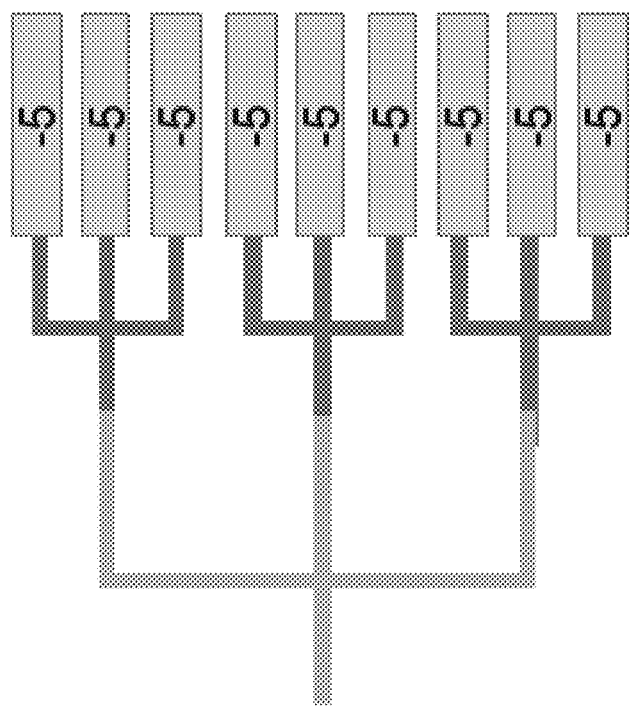
Figure 17B:
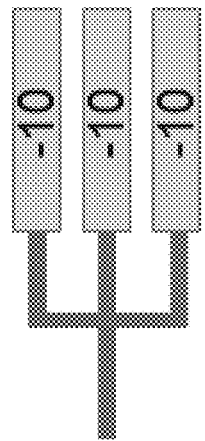
Figure 17B:

In some examples, such branching structure may be used to add multiples of phosphodiester-based charges to a charge tag. For example, rather than a single linear strand of polynucleotide or other phosphodiester-containing charge as disclosed herein, a branched structure such as according to a dendron structure as shown here may include as an end group a nucleotide or polynucleotide. By basing branching of such phosphodiester-containing tags in successive generations in accordance with a dendron structure as disclosed herein, multiple polynucleotides or other phosphodiester-based charges may be combined into a single charge tag. For example, dendron-based structures such as shown in FIGS. 17A and B. FIG. 17A shows an example of a tag combining three poly-T sequences into a single tag, which can be incorporated into a compound of Formula I according to methods as disclosed herein. In this example, the tag would carry a charge of −30. FIG. 17B illustrates several ways of combining phosphodiester-containing tags to yield a given charge (in this example, −30): a linear sequence of 30 phosphodiester charges, a triply-branched structure terminating in three phosphodiester sequences of 10, or a structure twice branched trebly and terminating in 6 phosphodiester sequences of five. An advantage of increased branching, such as in the last example as compared to the first, may be a higher density of charge, with a higher concentration of short charged sequences in proximity to each other as opposed to a single extended sequence which could extend away from a conductive channel.

Figure 19A:
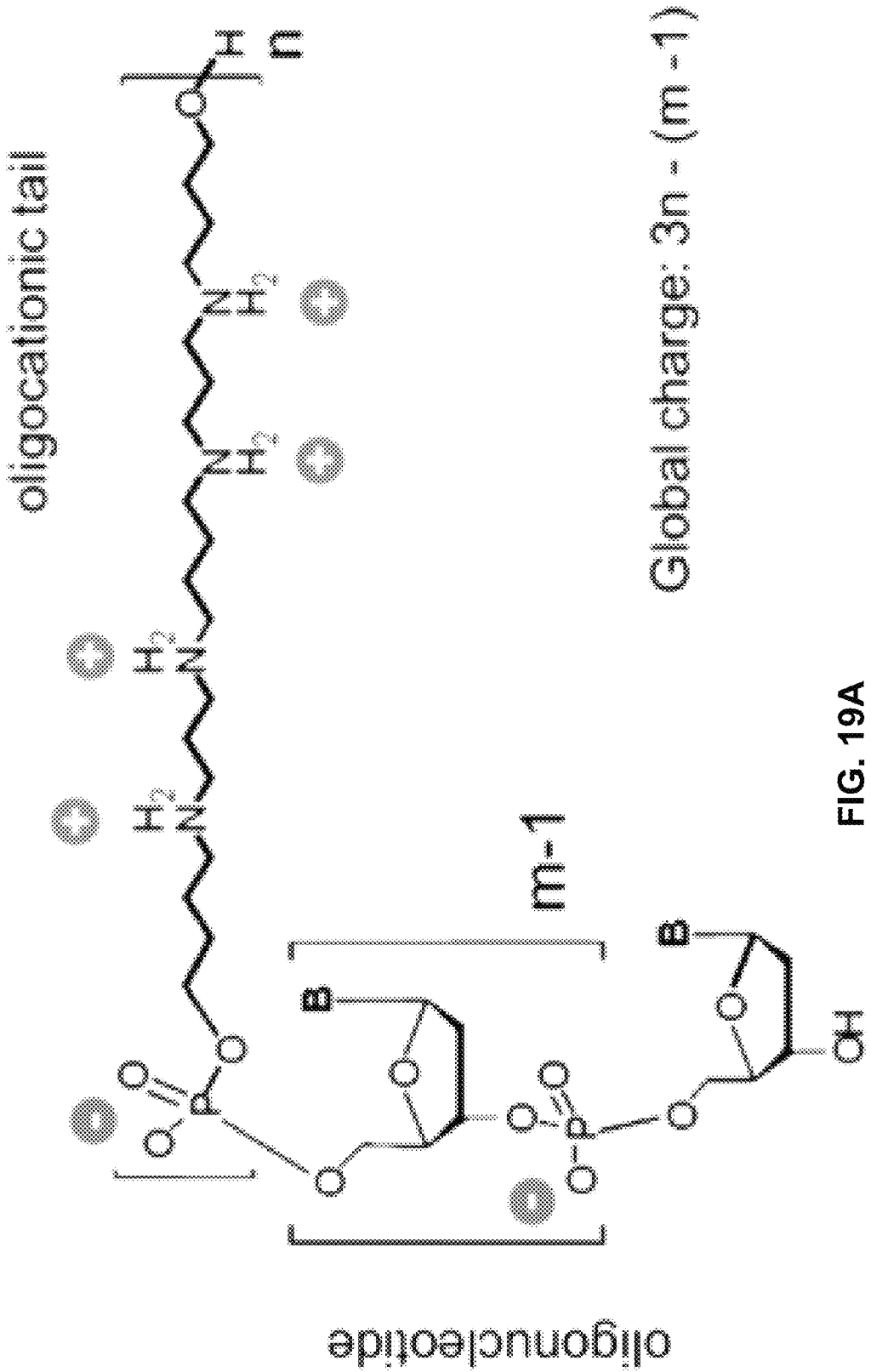
FIGS. 19A and 19B show examples of spermine-based charge tags in accordance with aspects of the present disclosure.
Figure 19B:
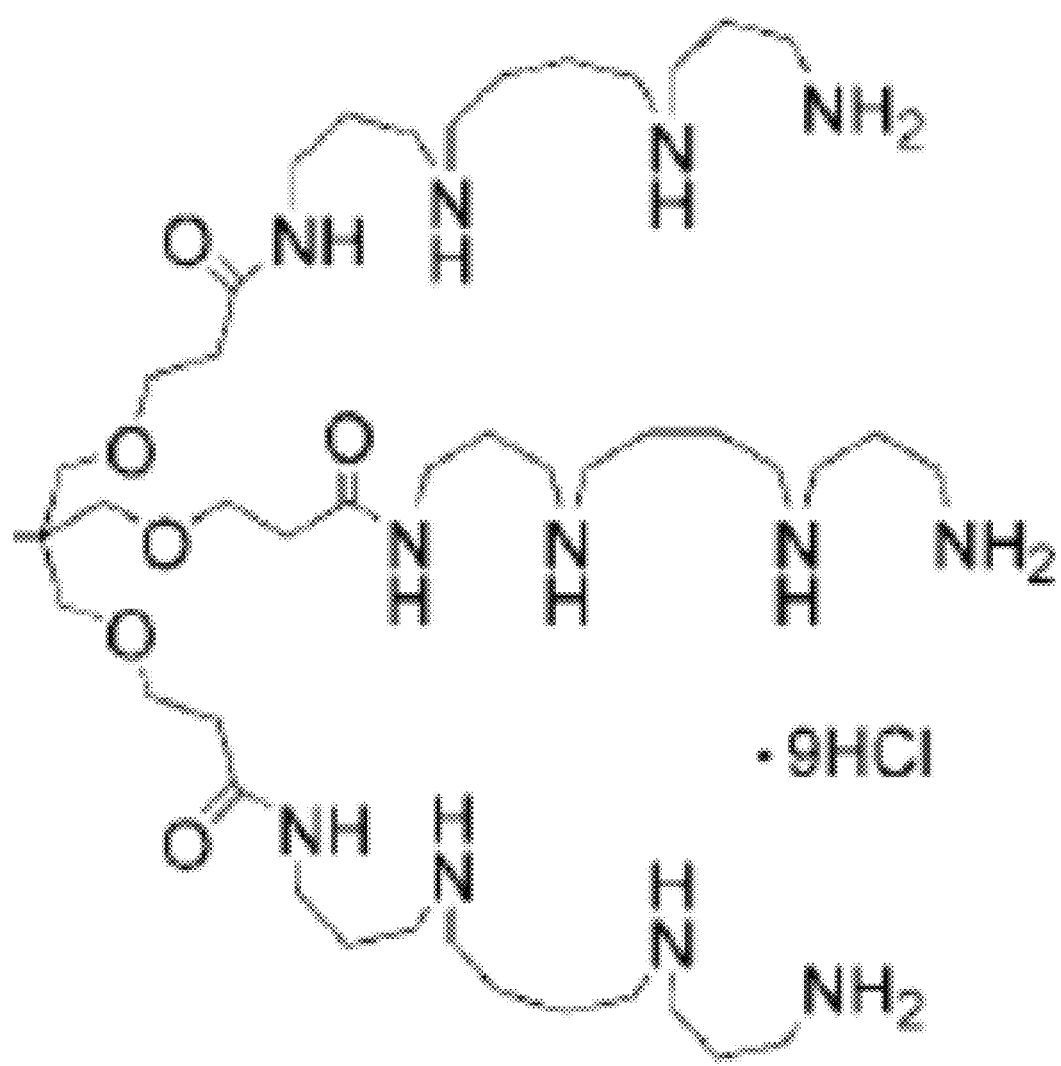

In another example, charge may be provided by a spermine-based component of a charge tag. For example, a spermine-based oligocationic charge may be added to a nucleotide and provide a positive charge as a charge tag in accordance with the present disclosure. An oligo-spermine conjugate has approximately 2.5 protonated amines at pH 7 An example of such a charge-tagged nucleotide is shown in FIGS. 19A and 19B. FIG. 19A shows an example of an oligo-spermine conjugate in accordance with an aspect of the present disclosure, and FIG. 19B shows a dendron-structured tag with spermine-derived end groups for magnifying the amount of charge that can be located at the end terminals of a charge tag. In both examples, chemistries disclosed herein for attaching charge tags to nucleotides could be adapted by skilled artisans for attaching such spermine-derived charge tags to nucleotides in accordance with aspects of the present disclosure.

The non-limiting examples below show the modification of a 5' amino nucleotide hexaphosphate with various linkers to allow for orthogonal attachment chemistry to dendron charge tags. A 5'-amine deoxy-thymine hexaphosphate (dT6P) (or other NPP) (1) may be functionalized with azido-butyric N-hydroxysuccinimide (NHS) ester (2a) or methyltetrazine NHS ester (2b) to form azide dT6P (3a) or methyltetrazine dT6P (3b) respectively (Scheme 6).
An azide dT6P (3a) may be conjugated to a linear strand of poly-T oligonucleotide (4) with a 5'-hexynyl group via copper(I)-assisted azide-alkyne cycloaddition (CuAAC) in
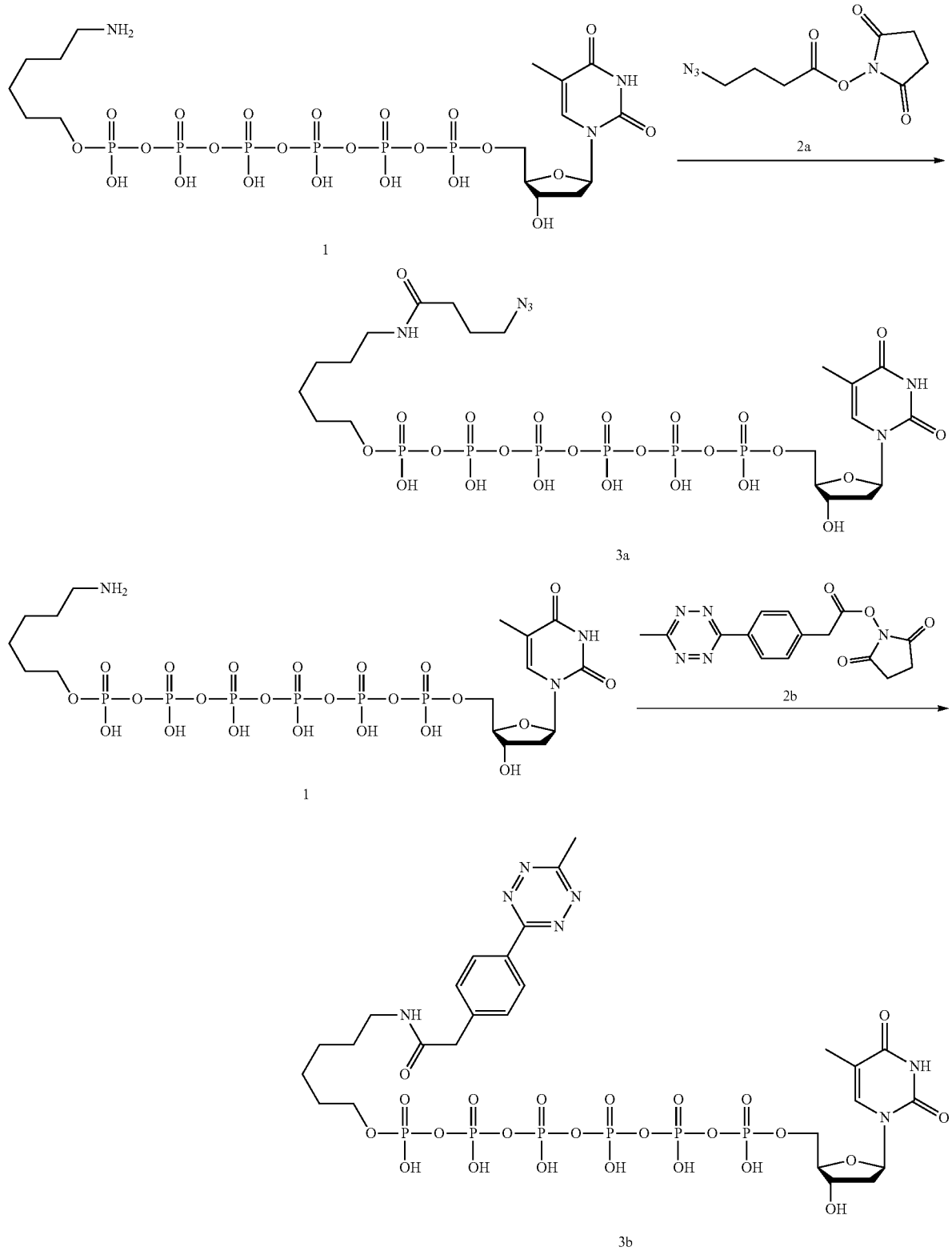
Scheme 6. Functionalization of 5'-amine dT6P.

the presence of CuSO₄, tris-hydroxypropyltriazolylmethyl-amine (THPTA) ligand and sodium ascorbate to form an oligonucleotide conjugate (5a). Purification was performed on C18 reverse-phase HPLC and eluted with 50 mM TEAA (pH 7.5) and acetonitrile. A methyltetrazine dT6P (3b) may then be conjugated to a dendron with a transcyclooctene (TCO) group in 50 mM phosphate buffer (pH 7.4) to form a nucleotide analog with a dendron charge tag.

Alternatively, an azide dT6P (3a) may also be conjugated to a dendron charge tag with a dibenzocyclooctyl (DBCO) group via copper-free strain promoted azide-alkyne cycloaddition (SPAAC) in 50 mM phosphate buffer (pH 7.4) to form a nucleotide analog with a dendron charge tag.

In the following scheme, an azide-alkyne click reaction may be made to link a nucleotide polyphosphate to a charge tag, such as a dendron charge tag with an alkyne group at its free valence end:

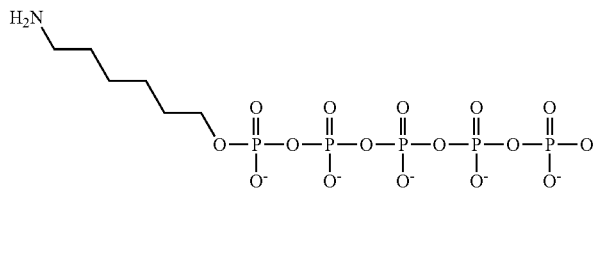
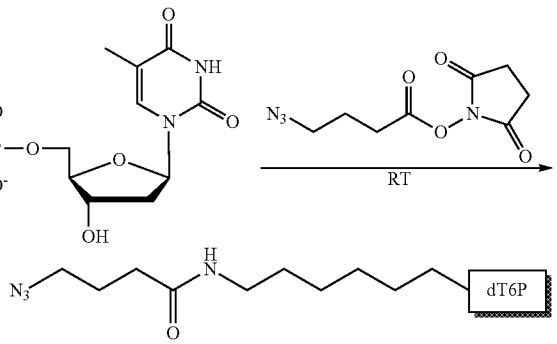

As would be appreciated by skilled artisans, the foregoing examples may be modified, such as by reversing the placement of each reactive group of a ligation reaction or click chemistry reaction, yielding the foregoing linkages but oriented in the opposite direction with regard to the 5' and 3' ends of the analog nucleotides.

Reactive groups and linker chemistries may be appended to nucleotides and charge tags according to various applicable chemistries in accordance with the present disclosure. In some non-limiting examples, an azide or methyltetrazine tail may be added to an aminated NPP by reaction with an appropriate NHS residue, which may include linker portions of various lengths such as PEG4 linker, or PEG linker of varying lengths. Non-limiting examples of such synthesis schemes include the following and variations thereof:

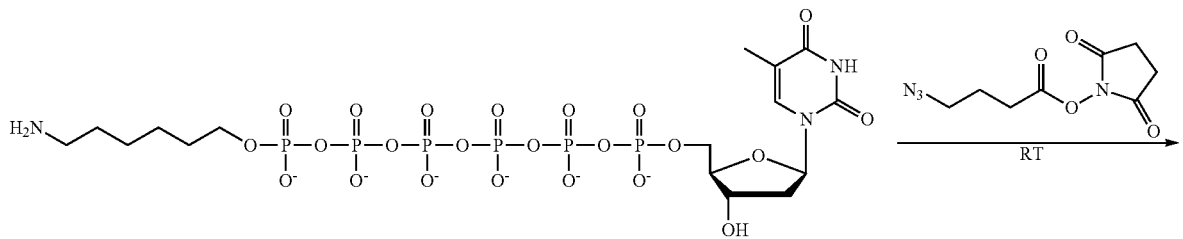
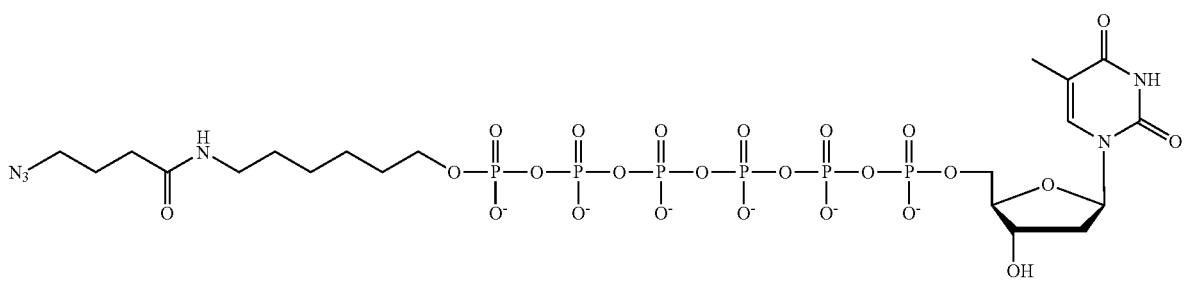

Different NHS-moieties may be used, to add an azide or methyltetrazine reactive group, and with various linker lengths. Non-limiting examples include:

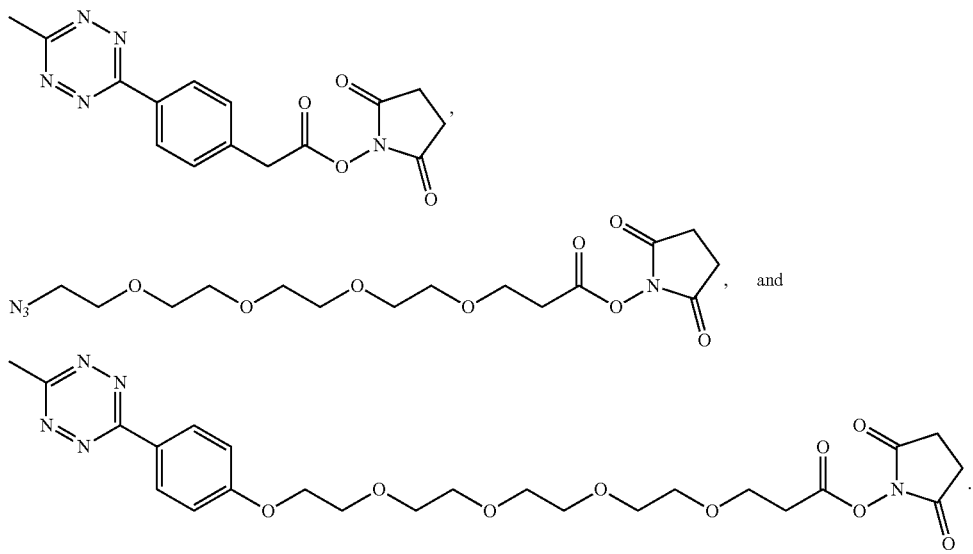

Various NPPs may be formed with different reactive groups for click or ligation chemistry reactions to connect them covalently with charge tags. Some non-limiting examples include:

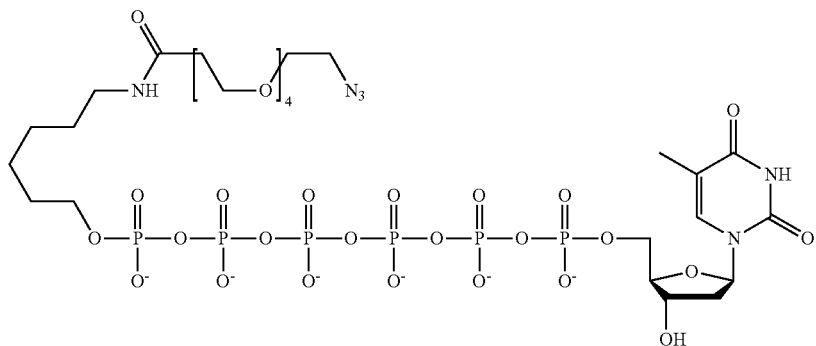

which could be reacted with an alkyne-containing charge tag, such as a dendron charge tag with an alkyne group at its free valence end.

Alternatively, a methyltetrazine containing NPP such as

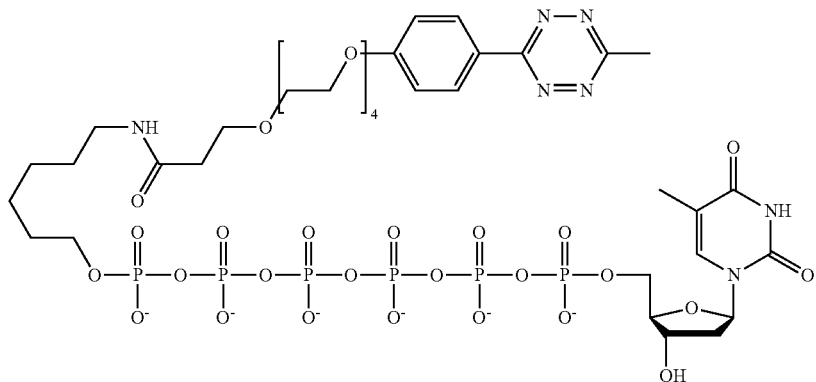

may be reacted with a TCO-containing charge tag, such as a dendron charge tag with a TCO group at its free valence end.

In other examples, DBCO-azide click chemistry between an NPP and a dendron charge tag may be used. In other examples, a maleimide group on a nucleotide or dendron charge tag may be reacted with a thiol group on a charge tag or nucleotide, respectively, to link the two via a maleimide-thiol reaction:

An NPP or charge tag containing a maleimide group

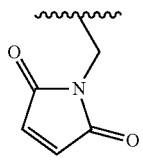

reacted with a charge tag or NPP containing a thiol-containing group, respectively, in the presence of a reducing agent such as (tris(2-carboxyethyl)phosphine) may result in covalent bonding between the two, for example

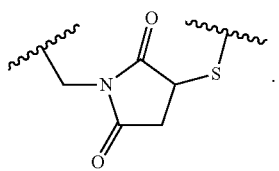 [SMILES: *CN1C(=O)CC(S*)C1=O]

Some non-limiting, illustrative examples of charge tags with three-dimensional conformations that may cause high charge density are shown in FIGS. 13A-C, 14A, 14B, 15, and 16. FIGS. 13-C show three examples of nucleotide analogs with oligonucleotide charge tags. For example, an oligonucleotide change tag may contain 5, 10, 15, 20, 25, 30, 35, 40, or more oligonucleotides. Also shown are a conductive channel, in this case a nanowire, and a functionalized attachment to the conductive channel, specifically an accepting region. The accepting region is indicated as "Glue." The oligonucleotide charge tags are shown as dashed lines extending from the 5' end of the modified nucleotide. Shown are three different conformations the charge tags may take. FIG. 13A, for example, illustrates a recognizable stem-and-loop structure. In such a structure, nucleotides along the stem portion base pair with each other, leaving a loop portion therebetween, in this example illustrated as orienting away from the acceptor region. Negative charges from the phosphodiester bonds between nucleotides of the oligonucleotide charge tag may thereby be maintained in close proximity with each other, maintaining a higher charge density than may be obtained if they adopted a linear, stretched-out conformation.

FIG. 13B, for example, shows another example, with not show a stem and loop structure but a bulge region of the charge tag. In this case, as in FIG. 13A, the charge tag includes a specificity region, shown boding to the acceptor region. Here, the specificity region includes segments of the oligonucleotide that are disparate from each other spatially under circumstances when the oligonucleotide is stretched linearly. But, when induced by electrostatic attraction to associate with the acceptor region, the portions of the specificity region draw closer together. This conformation is consistent with adoption of a stem and loop conformation (FIG. 13A) or bulge conformation (FIG. 13B), in both case causing an increase of charge density of the charge tag.

Figure 13C:
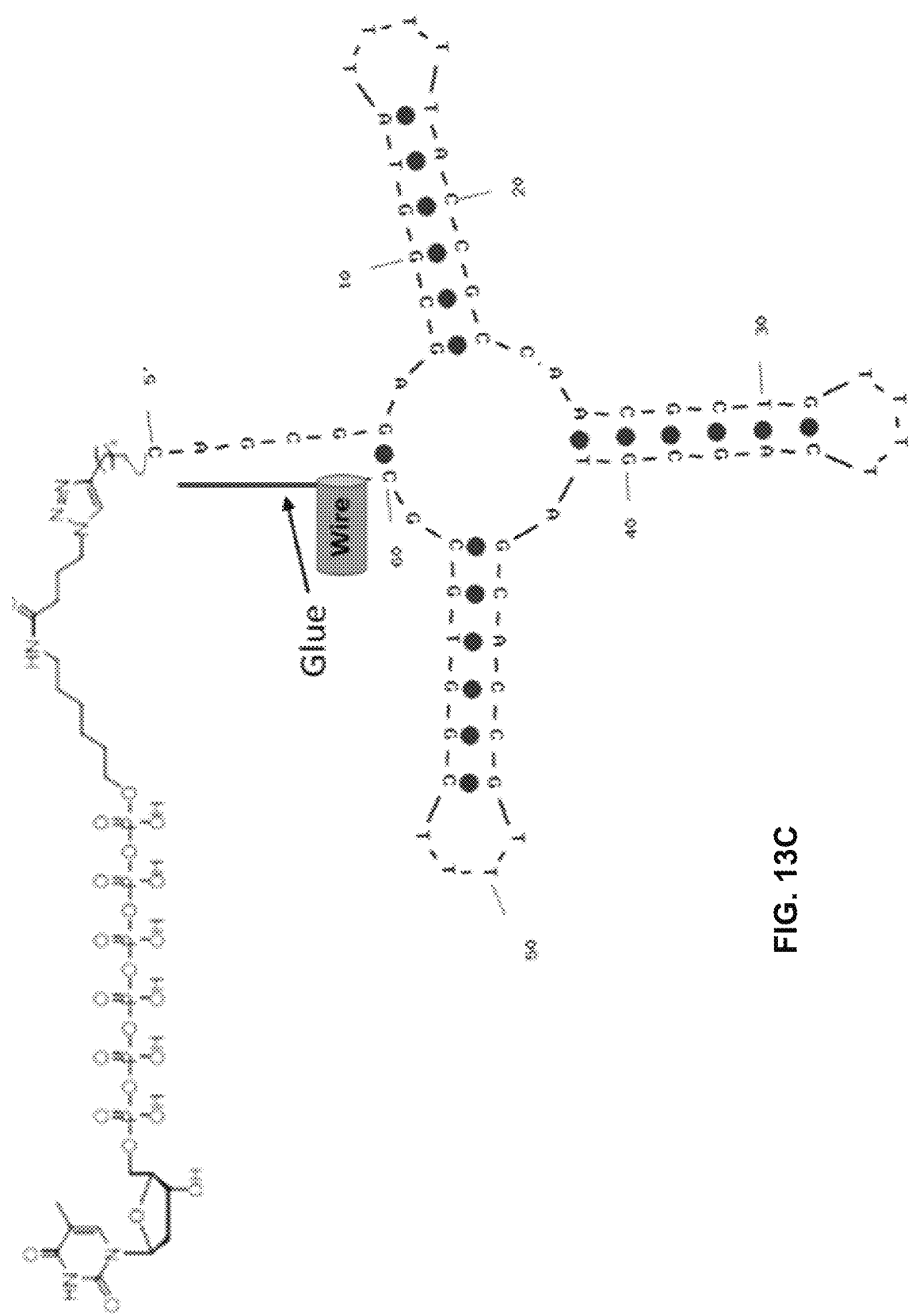
Figure 14B:
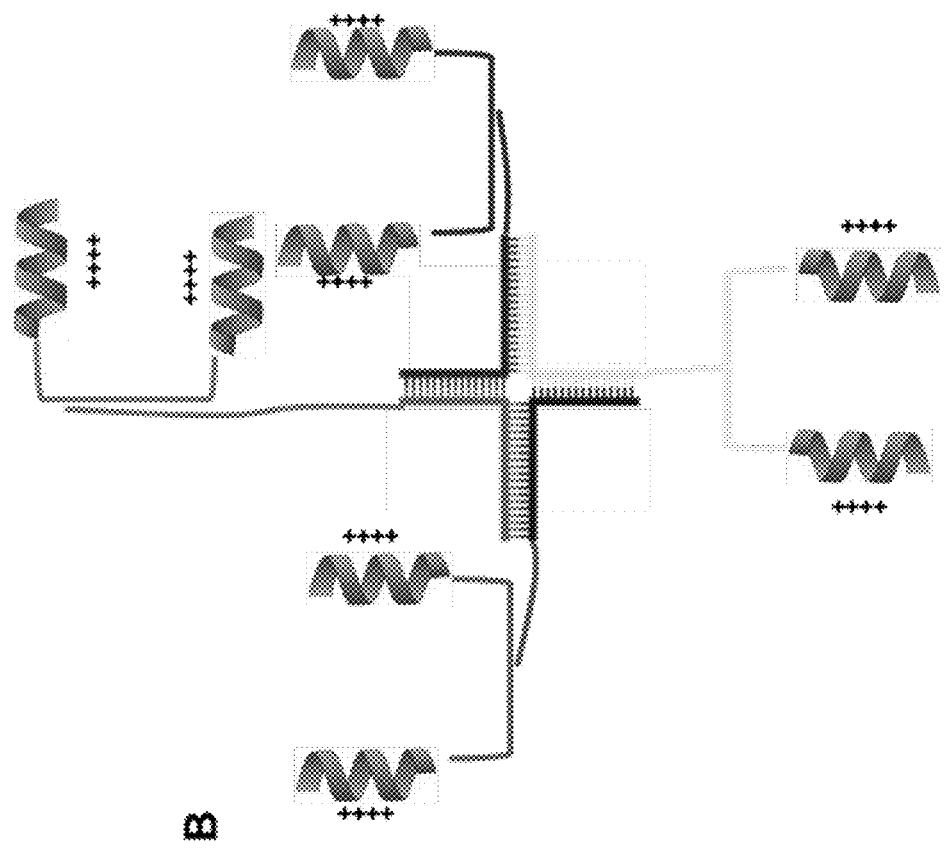
FIGS. 14A and 14B show an example of a cruciform charge tag.
Figure 14A:
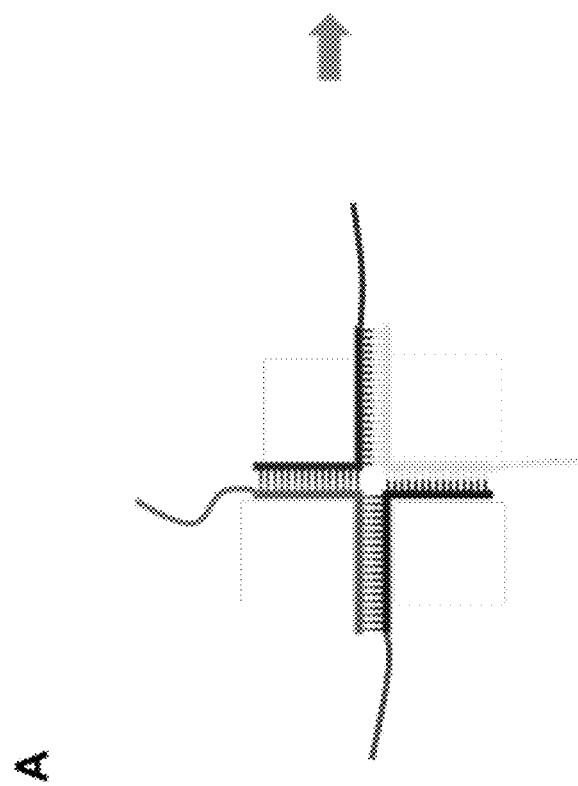

FIG. 13C shows charge tag adopting a cl overleaf architecture. Similar to the stem and loop conformation, stems extending from a central hub are formed by strands of nucleotides that are attracted to one another by Watson-Crick pair bonding rules, held together by a loop therebetween. Between stems radiating from the central hum are connecting strands of oligonucleotide. As with other examples, the pair-bonding of bases of the nucleotides in the charge tag induce the tag to adopt a conformation that causes the negative charges of the phosphodiester bonds between nucleotides to condense together resulting in an increase in charge density compared to what the density may be if the oligonucleotide were stretched out linearly.

Other three-dimensional conformations of oligonucleotide charge tags are possible. Negative charges of phosphodiester bonds between nucleotides can be induced to come together at a high charge density because of Watson-Crick base-pairing. Various three-dimensional shapes can be adopted, using, for example, DNA origami methodology, creating oligonucleotide charge tags in tubular, circular, cuboid, helical, condensed helical, spherical or spheroid, or other conformations yielding high charge density.

FIG. 14 shows an example of two charge tags, one including oligonucleotide sequences (14A, on the left) and the other including such sequences in addition to peptide nucleic acid sequences and polypeptides (14B, on the right). Not shown are connections between these charge tags and nucleotide analogs, but such attachment may be performed by chemical linking techniques such as those disclosed herein or otherwise known. The conformation of 14A on the left is a cruciform shape. Four oligonucleotide sequences are bound together in a conformation resembling a Holiday structure (as may occur during DNA recombination events). As shown in 14A, portions of the four polynucleotides bond to each other according to Watson-Crick base pairing. Each oligonucleotide also extends from the pair-bonded central portion into single-stranded overhangs. The pair bonding holds negative charges of the phosphodiester linkages within the oligonucleotides in proximity to each other, increasing charge density.

On the right, in 14B, peptide nucleic acid and polypeptide sequences are added to the charge tag shown in 14A, resulting in another non-limiting example of a charge tag. In this example, four sequences of peptide nucleic acids each connect, at their ends, polypeptide sequences. The polypeptide sequences form helical structures because of electrostatic attraction between some of the amino acids within the polypeptides. However, in these examples, the polypeptides have a net positive charge (notwithstanding the inclusion of some negatively charged amino acids therein which assist in adoption of a helical conformation). Portions of the peptide nucleic acid sequences connecting pairs of polypeptides are also hybridized to single-stranded portions of the polynucleotides that extend from the base-paired core. The strong bonds between the peptide nucleic acids and tightened coil conformation of the positively charged polypeptides allow for a net-positive charge of the charge tag and with a high charge density. Other examples of charge tags adopting similar architectures may have a net negative charge.

Figure 15:
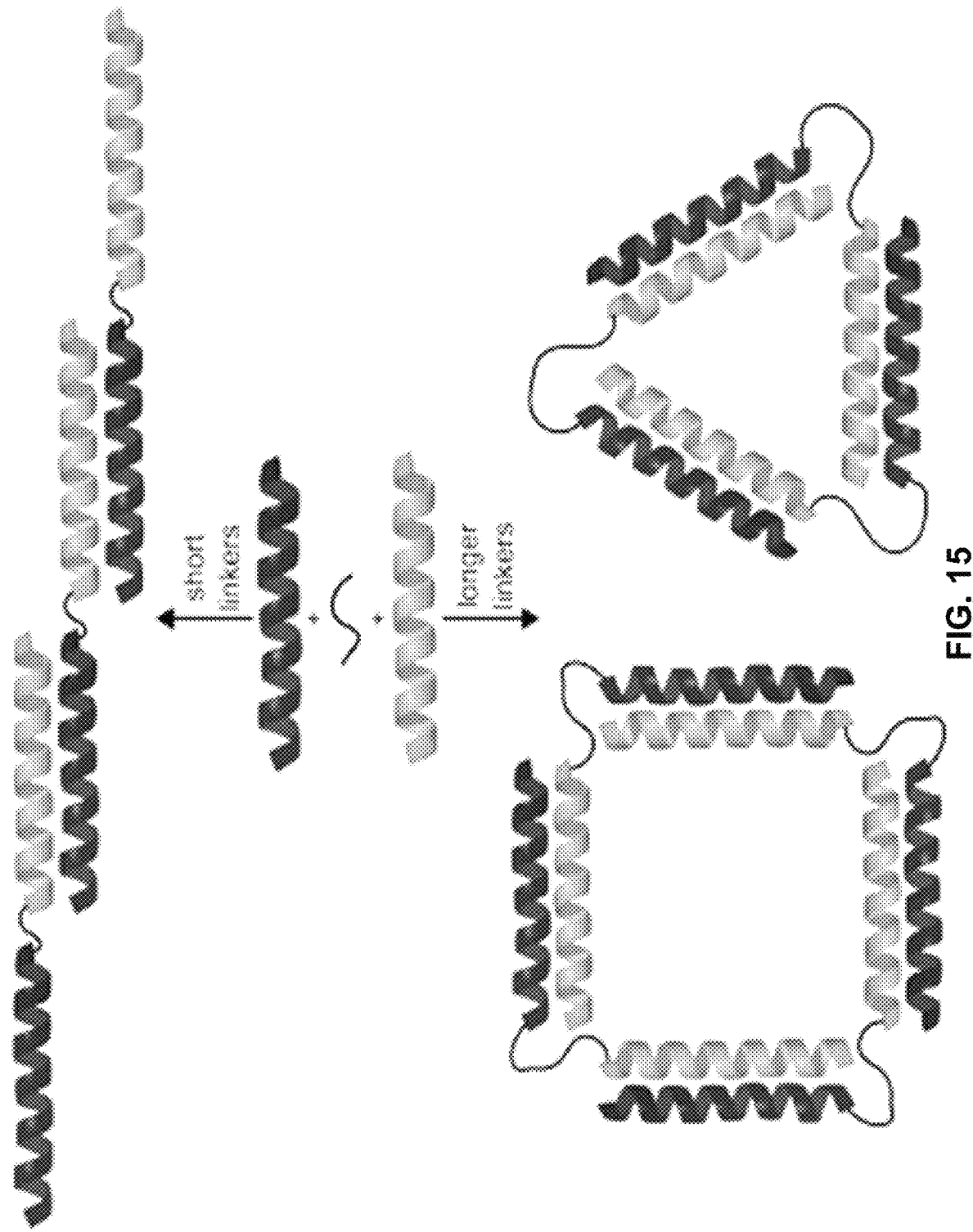
FIG. 15 shows several examples of polypeptide charge tags including coiled polypeptides and assembly thereof.

FIG. 15 shows some examples of polypeptide charge tags in which polypeptides adopt different three-dimensional architectures that result in high charge density. Coiled portions of polypeptide may be connected by linker sequences. When the linker sequences are fairly short, the coiled structures may be able to bind to one another in roughly overall linear arrays. Such conformation is possible because of electrostatic attraction between positively and negatively charged amino acids within the polypeptides. Overall, however, the polypeptide charge tags may have a net positive or net negative charge. With longer linkers between coiled portions of polypeptides of a charge tag, however, decreased stearic hindrance permits greater bending between adjacent coiled portions, permitting adoption of more complicated architectures such as shown in the lower portion of FIG. 15. These possibilities may result in even higher charge density. As with the examples shown in FIGS. 14A and 14B, these example charge tags could be attached to nucleotide analogs (not shown).

Figure 16:
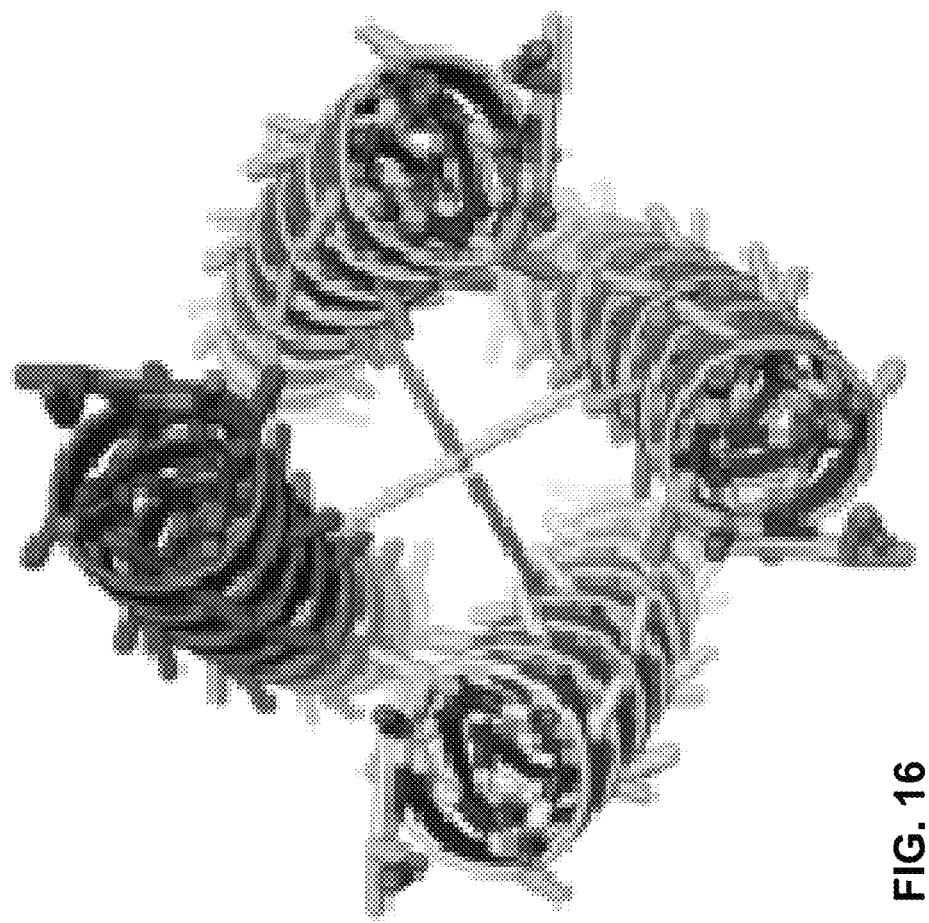
FIG. 16 shows an example of a charge tag including polypeptides arranged in a coiled-coil configuration.
Figure 16:
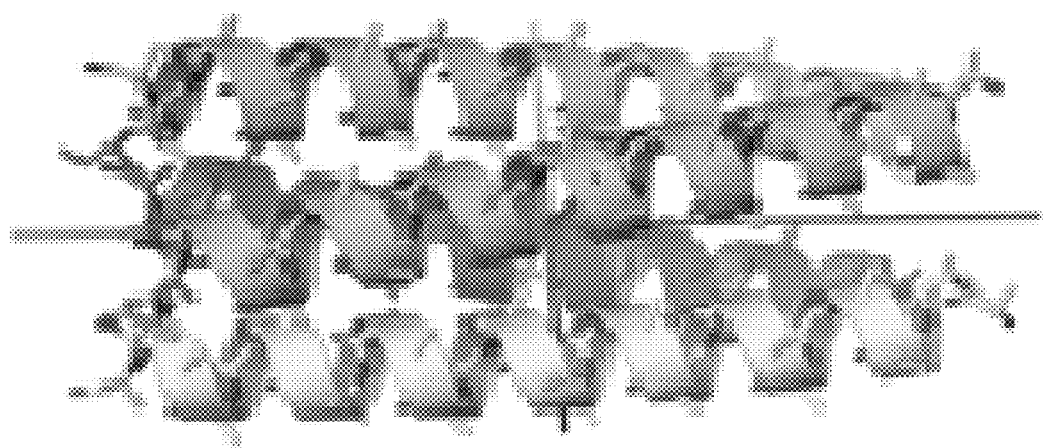

FIG. 16 shows examples of polypeptide charge tags adopting a coiled coil architecture, wherein electrostatic attraction between amino acids within a helix, and between amino acids of different helices, may induce the polypeptides to form a condensed structure. A result may be that a coiled coil may have a net negative or net positive charge, with the net charge held together at a high charge density (compared to what the charge density may be if the polypeptide sequences were stretched linearly).

Any of the click or ligation chemistries described above for attaching a nucleotide analog to a charge tag, or other chemistries for forming covalent bonds, may be used to attach any of the foregoing charge tags to a nucleotide analog.

Charge tags including oligonucleotides, polypeptides, or both, with or without peptide nucleic acids, may therefore be made to adopt different three-dimensional architectures with elevated charge density compared to linear charge tags stretched linearly. A charge tag may have a net negative charge, such as if it contains an excess of phosphodiester or negative amino acids relative to positive charges, or a net positive charge such as if it has more positively charged amino acids than negatively charged groups. Coiled coils can be computationally designed to adopt specific compact structures, based on well characterized molecular interactions between amino acid components. An example of coiled coils that can be used include leucine zippers, which may be in, for example, dimeric or trimeric forms, of controlled length and diameter. Furthermore, because interactions that govern coiled coil compact structure are localized in the interior, the surface can be independently engineered to carry a wide range of charges.

A charge tag as disclosed herein may have a charge from anywhere between −200e and +200e, or between −100e and +100e, or between −40e and +40e, or between −20e and +20e −40 and +40, or any range therein. In some examples, net charge or partial net charge of a charge tag may be packed into a density of from −200e to +200e per cubic nanometer, or from −100e to +100e per cubic nanometer, or from −40e to +40e per cubic nanometer, or from −20e to +20e per cubic nanometer, or any range therein.

In some examples of the technology disclosed herein, one or more computer readable storage devices or memory storing computer-readable instructions that when executed by a computer, cause the computer to perform at least any one of the methods disclosed herein. In some examples, a system is configured to perform at least a portion of any one of the methods disclosed herein. In some examples, a system is coupled to computer readable storage devices or memory storing computer-readable instructions that when executed, cause the system to perform at least any one of the methods disclosed herein.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting. Although some examples may have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

What is claimed is:

1. A method comprising:
   detecting an incorporation of a labelled nucleotide into a nascent polynucleotide strand complementary to a template polynucleotide strand by a polymerase, wherein the polymerase is tethered to a solid support conductive channel by a tether,
   the labelled nucleotide is a compound of Formula I

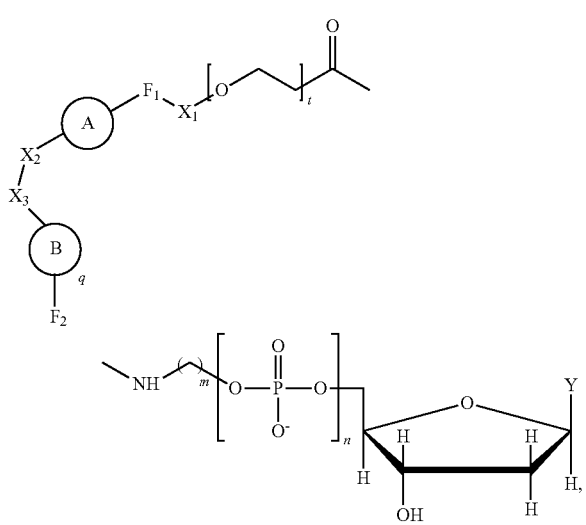

wherein n is an integer from 3 to 10, m is an integer from 1 to 10, t is an integer from 0 to 50, $X_1$ is a direct bond, a $C_1$-$C_{10}$ alkyl, a $C_1$-$C_{10}$ oxaalkyl, a $C_1$-$C_{10}$ thiaalkyl, or a $C_1$-$C_{10}$ azaalkyl, $X_2$ is $C_1$-$C_{20}$ alkyl wherein optionally one or more individual $CH_2$ residue is replaced with one or more of a peptide bond and (—O—$CH_2$—$CH_2$—)$_a$ wherein a is an integer from 1 to 24, $X_3$ is a an oligonucleotide wherein the oligonucleotide hybridizes to an acceptor region of the tether, $F_1$ is selected from a fluorophore and a direct bond and $F_2$ is absent or a fluorophore, A was formed by a reaction comprising a linking reaction and the linking reaction is selecting from an azide-alkyne copper-assisted click reaction, a tetrazine-trans-cyclooctene ligation, an azide-dibenzocyclooctyne group copper-free click reaction, a thiol-maleimide conjugation, and a N-hydroxysuccinimide ester-amine linkage reaction, and Y is selected from

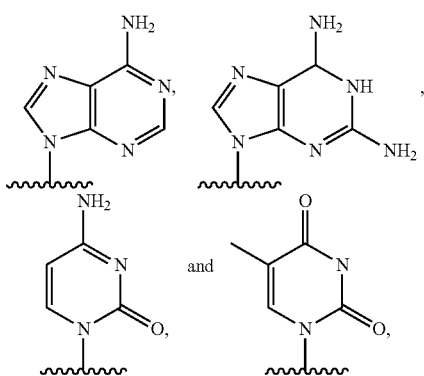

q is an integer from 1 to 100, and

B is selected from (i) an amino acid; (ii) a nucleotide;

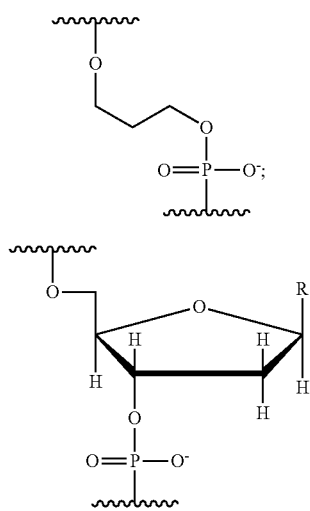

wherein each R is independently selected from Y and hydrogen;

and (v) a dendron; and wherein q is equal to 1 when B is a dendron, and the conductive channel is to detect the labelled nucleotide during the incorporation.

2. The method of claim 1, wherein the q number of B has a charge and the charge is between about −100e and about +100e.

3. The method of claim 2, wherein the q number of B has a charge density and the charge density is between about −100e per cubic nanometer and about +100e per cubic nanometer.

4. The method of claim 1, wherein the q number of B has a charge and the charge is between about −200e and about +200e.

5. The method of claim 4, wherein the q number of B has a charge density and the charge density is between about −200e per cubic nanometer and about +200e per cubic nanometer.

6. The method of claim 1, wherein the q number of B comprises a polynucleotide.

7. The method of claim 6, wherein the polynucleotide is selected from a branched polynucleotide and one or more hairpin loops.

8. The method of claim 7, wherein the polynucleotide comprises from two to five hairpin loops.

9. The method of claim 1, wherein the q number of B comprises a polypeptide.

10. The method of claim 9, wherein the polypeptide is selected from a branched polypeptide, coiled polypeptide, and coiled-coil polypeptide.

11. The method of claim 1, wherein B comprises an amino acid, and one or more of the q number of B comprise methyllysine, dimethyllysine, or trimethyllysine.

12. The method of claim 1, wherein B is a dendron and the dendron comprises z generations comprising one or more constitutional repeating unit and a plurality of end units, wherein z is an integer from 1 to 6, the constitutional end units are selected from:

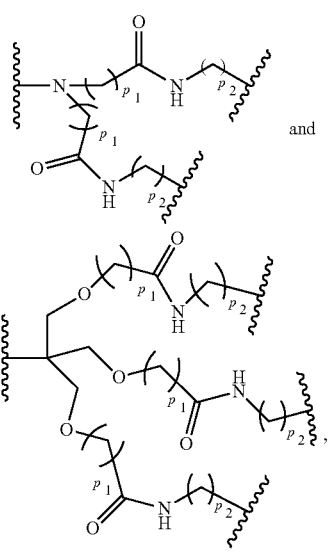

wherein $p_1$ is an integer from 1 to 3, wherein any one or more of the $p_1$ —$CH_2$— groups is optionally replaced with from 1 to 3 —O—$CH_2$—$CH_2$— groups, $p_2$ is an integer from 1 to 3, wherein any one or more of the $p_2$ —CH$_2$— groups is optionally replaced with from 1 to 3 —O—CH$_2$—CH$_2$— groups, and the end groups are selected from carboxylic acid, sulfonic acid, phosphonic acid, sperminyl group, amino group, and quaternary ammonium group.

13. The method of claim 1, further comprising successively incorporating a plurality of labelled nucleotides wherein the charge of each of the plurality of labelled nucleotides differs from the charge of any other of the plurality of labelled nucleotides when the Y of the each and the Y of the any other differ from each other.

14. The method of claim 13, further comprising identifying the Y of one or more labelled polynucleotide incorporated into the nascent polynucleotide strand based on the charge detected by the conductive channel.

15. The method of claim 1, wherein $X_2$ is (—O—CH$_2$—CH$_2$—)$_a$ wherein a is an integer from 1 to 24.

16. The method of claim 15, wherein a is 24.
17. The method of claim 15, wherein a is 16.
18. The method of claim 15, wherein a is 12.
19. The method of claim 15, wherein a is 8.
20. The method of claim 15, wherein a is 4.

\* \* \* \* \*

UNITED STATES PATENT AND TRADEMARK OFFICE
CERTIFICATE OF CORRECTION

PATENT NO. : 11,578,094 B2  
APPLICATION NO. : 17/106963  
DATED : February 14, 2023  
INVENTOR(S) : Mandell et al.

Page 1 of 1

It is certified that error appears in the above-identified patent and that said Letters Patent is hereby corrected as shown below:

In the Specification

Column 1, Cross-Reference to Related Applications Lines 8 to 10: Delete "§ 371 of International Application No. PCT/US2018/027961, filed on April 17, 2018, published as WO 2018195070 on October 25, 2018," and insert -- "§ 371 of International Application No. PCT/US2019/018565, filed on February 19, 2019, published as WO 2019/161381 on August 22, 2019, --

In the Claims

Column 113, Line 12: Claim 1, Delete "a an" and insert -- an --

Column 113, Line 47 to 54: Claim 1, Delete " 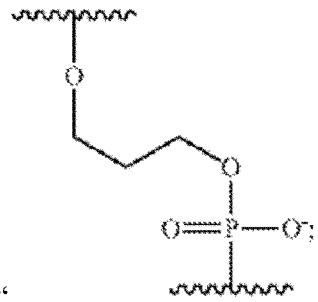 (iv)" and insert

-- 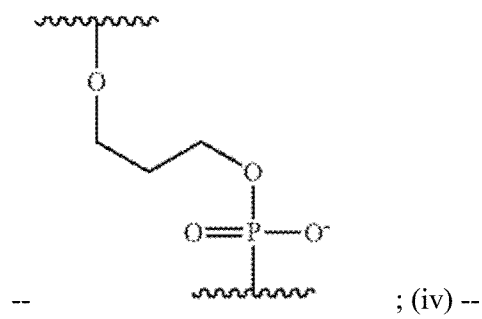 ; (iv) --

Signed and Sealed this  
Twenty-fifth Day of April, 2023

Katherine Kelly Vidal  
*Director of the United States Patent and Trademark Office*